United States Patent
Wilde

(10) Patent No.: US 6,399,609 B1
(45) Date of Patent: Jun. 4, 2002

(54) THERAPEUTIC USAGE OF TETRAHYDROPTERIDINES AND PYRIDYLPIPERAZINES FOR TREATMENT OF NEUROLOGICAL DISORDERS

(75) Inventor: Richard Gerald Wilde, Newark, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/570,775

(22) Filed: May 11, 2000

Related U.S. Application Data

(62) Division of application No. 08/857,349, filed on May 16, 1997, now Pat. No. 6,083,948.
(60) Provisional application No. 60/018,198, filed on May 23, 1996.
(51) Int. Cl.[7] .................... A61K 31/519; A61K 31/525; A61K 31/53; C07D 475/06
(52) U.S. Cl. ................. 514/249; 514/241; 514/245; 514/248; 514/250; 544/257; 544/258; 544/260; 544/180; 544/194; 544/250; 544/251; 544/346; 544/350
(58) Field of Search ................. 514/249, 241, 514/245, 248; 544/250, 251, 258, 346, 350

(56) References Cited

U.S. PATENT DOCUMENTS

| | | | |
|---|---|---|---|
| 4,091,219 A | 5/1978 | Denzel et al. | |
| 4,510,141 A | 4/1985 | Heckendorn | |
| 4,665,182 A | 5/1987 | Nichol et al. | |
| 4,701,455 A | 10/1987 | Nichol et al. | |
| 5,198,547 A | 3/1993 | Bailey et al. | |
| 5,283,244 A | 2/1994 | Sakamoto et al. | |
| 5,424,311 A | 6/1995 | Billhardt-Troughton et al. | |

FOREIGN PATENT DOCUMENTS

| | | |
|---|---|---|
| JP | 08092250 | 4/1996 |
| WO | 9533727 | 12/1995 |
| WO | 9533750 | 12/1995 |
| WO | 9534563 | 12/1995 |

OTHER PUBLICATIONS

J. Rivier et al., Proc. Nat. Acad. Sci., 80:4851 (1993).
W. Vale et al., Science, 213:1394 (1981).
W. Vale et al., Rec. Prog. Horm. Res., 39:245 (1983).
G.F. Koob, Persp. Behav. Med., 2:39 (1985).
E.B. DeSouza et al., J. Neurosci., 5:3189 (1985).
J.E. Blalock, Physiological Reviews, 69:1 (1989).
J.E. Morley, Life Science, 41:527 (1987).
E.B. DeSouza Hosp. Practice, 23:59 (1988).
C.B. Nemeroff et al., Science, 226:1342 (1984).
C.M. Banki et al., Am. J. Psychiatry, 144:873 (1987).
R.D. France et al., Biol. Psychiatry, 28:86 (1988).
M. Arato et al., Biol. Psychiatry 25:355 (1989).
C.B. Nemeroff et al., Arch. Gen. Psychiatry, 45:577 (1988).
P.W. Gold et al., Am. J. Psychiatry, 141:619 (1984).
F. Holsboer et al., Psychoneuroendocrinology, 9:147 (1984).
P.W. Gold et al., New Eng. J. Med., 314:1129 (1986).
R.M. Sapolsky, Arch. Gen. Psychiatry, 46:1047 (1989).
Grigoriadis et al., Neuropsychopharmacology, 2:53 (1989).
D.R. Britton et al., Life Sci., 31:363 (1982).
C.W. Berridge and A.J. Dunn, Regul. Peptides, 16:83 (1986).
C.W. Berridge and A.J. Dunn, Horm. Behav., 21:393 (1987).
Brain Research Reviews, 15:71 (1990).
K.T. Britton et al., Psychopharmacology, 86:170 (1985).
K.T. Britton et al., Psychopharmacology, 94:306 (1988).
N.R. Swerdlow et al., Psychopharmacology, 88:147 (1986).
G.F. Koob and K.T. Britton, Corticotropin–Releasing Factor: Basic and Clinical Studies of a Neuropeptide, E.B. DeSouza and C.B. Nemeroff eds., CRC Press, p. 221 (1990).

*Primary Examiner*—Theodore J. Criares
(74) *Attorney, Agent, or Firm*—Kenneth B. Rubin; Blair Q. Ferguson

(57) ABSTRACT

Corticotropin releasing factor (CRF) antagonists of formula I:

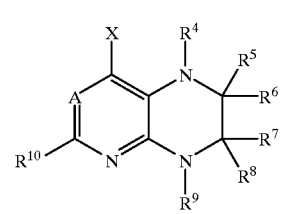

and their use in treating anxiety, depression, and other psychiatric and neurological disorders.

4 Claims, No Drawings

THERAPEUTIC USAGE OF TETRAHYDROPTERIDINES AND PYRIDYLPIPERAZINES FOR TREATMENT OF NEUROLOGICAL DISORDERS

This application is a division of U.S. Ser. No. 08/857,349, filed May 16, 1997, now U.S. Pat. No. 6,083,948; which claims the benefit of Provisional Application No. 60/018,198 filed May 23, 1996.

FIELD OF THE INVENTION

This invention relates to compounds and pharmaceutical compositions, and to methods of using same in the treatment of psychiatric disorders and neurological diseases including major depression, anxiety-related disorders, post-traumatic stress disorder, supranuclear palsy and feeding disorders.

BACKGROUND OF THE INVENTION

Corticotropin releasing factor (herein referred to as CRF), a 41 amino acid peptide, is the primary physiological regulator of proopiomelanocortin (POMC)-derived peptide secret.gland [J. Rivier et al., *Proc. Nat. Acad. Sci. (USA)* 80:4851 (1983); W. Vale et al., *Science* 213:1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in brain. [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence that CRF plays a significant role in integrating the response of the immune system to physiological, psychological, and immunological stressors [J. E. Blalock, *Physiological Reviews* 69:1 (1989); J. E. Morley, *Life Sci.* 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, *Hosp. Practice* 23:59 (1988)].

In affective disorder, or major depression, the concentration of CRF is significantly increased in the cerebral spinal fluid (CSF) of drug-free individuals [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol Psychiatry* 25:355 (1989)]. Furthermore, the density of CRF receptors is significantly decreased in the frontal cortex of suicide victims, consistent with a hypersecretion of CRF [C. B. Nemeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am J. Psychiatry* 141:619 (1984); F. Holsboer et al., *Psychoneuroendocrinology* 9:147 (1984); P. W. Gold et al., *New Eng. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is preliminary evidence that tricyclic antidepressants can alter CRF levels and thus modulate the numbers of CRF receptors in brain [Grigoriadis et al., *Neuropsychopharmacology* 2:53 (1989)].

There has also been a role postulated for CRF in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn *Regul. Peptides* 16:83 (1986)]. Preliminary studies using the putative CRF receptor antagonist a-helical ovine CRF (9-41) in a variety of behavioral paradigms demonstrate that the antagonist produces "anxiolytic-like" effects that are qualitatively similar to the benzodiazepines [C. W. Berridge and A. J. Dunn *Horm. Behav.* 21:393 (1987), *Brain Research Reviews* 15:71 (1990)]. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., *Psychopharmacology* 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (a-helical $CRF_{9\text{-}41}$) in a variety of behavioral paradigms have demonstrated that the CRF antagonist produces "anxiolytic-like" effects qualitatively similar to the benzodiazepines [for review see G. F. Koob and K. T. Britton, In: *Corticotropin-Releasing Factor: Basic and Clinical Studies of a Neuropeptide*, E. B. De Souza and C. B. Nemeroff eds., CRC Press p221 (1990)].

Several published patent applications disclose corticotropin releasing factor antagonist compounds. Among these are DuPont Merck PCT application U.S. Pat. No. 94/11050, Pfizer WO 95/33750, Pfizer WO 95/34563, and Pfizer WO 95/33727. U.S. Pat. No. 5,424,311 discloses antiviral use of azaquinoxalines of the formula:

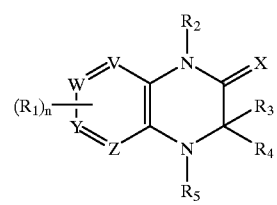

in which V, W, Y and Z are CH, CR1, or N; X can be oxygen, sulfur or $NR^2$; $R^1$ can be alkyl, alkoxy, alkylthio, alkylsulfinyl, alkylsulfonyl, or alkylamino; $R^2$, $R^3$, $R^4$ and $R^5$ can be hydrogen, alkyl, aryl or heteroaryl.

U.S. Pat. No. 5,283,244 discloses glutamate receptor antagonizing activity of fused pyrazine derivatives of the the formula:

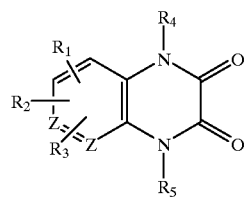

wherein Z represents C or N; R1 represents a diazole or triazole substituent; and the other R groups represent hydrogen or various substituents such as alkyl, phenyl, or heterocycle.

SUMMARY OF THE INVENTION

This invention is a method of treating an affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, or inflammatory disorder in a mammal comprising administering to the mammal a therapeutically effective amount of a CRF antagonist compound of formula I:

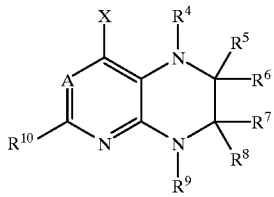

(I)

or a pharmaceutically accetable salt or prodrug thereof, wherein:

A is N or C—$R^{11}$;

X is H, $OR^1$, $S(O)_n R^1$, $NR^1 R^2$, $CR^1 R^2 R^3$, phenyl (optionally substituted with 1–4 groups independently chosen from halogen, $C_1$–$C_4$ haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl) or heteroaryl (optionally substituted at one to all valence-allowed positions with groups independently chosen from halogen, $C_1$–$C_4$ haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl);

n is 0, 1 or 2;

$R^1$ is $C_1$–$C_{12}$ alkyl, $C_2$–$C_{12}$ alkoxyalkyl, $C_3$–$C_{12}$ cycloalkyl, $C_4$–$C_{12}$ cycloalkylalkyl, $C_2$–$C_{12}$ alkenyl, $C_2$–$C_{12}$ alkynyl, aryl-($C_1$–$C_{12}$ alkyl), $C_3$–$C_{12}$ dialkylaminoalkyl, $C_2$–$C_{13}$ cyanoalkyl, $C_2$–$C_5$ carboalkoxy-($C_1$–$C_{12}$ alkyl), phenyl (optionally substituted with 1–4 groups independently chosen from halogen, $C_1$–$C_4$ haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl), or heteroaryl (optionally substituted at one to all valence-allowed positions with groups independently chosen from halogen, $C_1$–$C_4$ haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl);

$R^2$ and $R^3$ are independently chosen from H, $C_1$–$C_{12}$ alkyl, $C_2$–$C_{12}$ alkoxyalkyl, $C_3$–$C_{12}$ cycloalkyl, $C_4$–$C_{12}$ cycloalkylalkyl, $C_2$–$C_{12}$ alkenyl, $C_2$–$C_{12}$ alkynyl, aryl-($C_1$–$C_{12}$ alkyl), $C_3$–$C_{12}$ dialkylaminoalkyl, $C_2$–$C_{13}$ cyanoalkyl, $C_1$–$C_4$ carboalkoxy, $C_2$–$C_{12}$ carboalkoxyalkyl, C(=O)$CH_3$, phenyl (optionally substituted with 1–4 groups independently chosen from halogen, $C_1$–$C_4$ haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl), or heteroaryl (optionally substituted at one to all valence-allowed positions with groups independently chosen from halogen, $C_1$–$C_4$ haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl);

$R^4$ is H, $C_1$–$C_{12}$ alkyl, allyl, propargyl or benzyl (optionally substituted with 1–4 groups independently chosen from halogen, $C_1$–$C_4$ haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl);

$R^1$ and $R^4$ may also optionally be taken together, along with the other four interconnected atoms, to form a ring of 5–9 total atoms, the structural sequence between the X group and the ring nitrogen atom consisting of the group $(CH_2)_p W(CH_2)_q$;

p and q are independently 0, 1 or 2;

W is $CH_2$, $C(CH_3)_2$, C(=O), O, S or $NCH_3$;

$R^5$, $R^6$, $R^7$ and $R^8$ are independently chosen from H, $C_1$–$C_4$ alkyl, allyl, propargyl, phenyl (optionally substituted with 1–4 groups independently chosen from halogen, $C_1$–$C_4$ haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl) or benzyl (optionally substituted with 1–4 groups independently chosen from halogen, $C_1$–$C_4$ haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl); $R^4$, $R^5$ and $R^6$ may also be taken together, along with the two interconnecting atoms, to constitute either an imidazole or tetrazole ring, the imidazole ring being optionally substituted with 1-2 groups chosen independently from $C_1$–$C_4$ alkyl or phenyl;

$R^5$ and $R^6$ may also be taken together to be O, S or $NR^{12}$;

$R^9$ is phenyl (optionally substituted with 1–4 groups chosen from halogen, $C_1$–$C_4$ haloalkyl, $C_1$–$C_4$ alkyl, $C_2$–$C_6$ alkenyl, $C_1$–$C_4$ alkoxy, $C_1$–$C_4$ alkylthio, $C_1$–$C_4$ alkylsulfonyl, $C_2$–$C_6$ dialkylamino, nitro, $C_2$–$C_5$ carboalkoxy or cyano), pyridyl (optionally substituted with 1–4 groups chosen from halogen, $C_1$–$C_4$ haloalkyl, $C_1$–$C_4$ alkyl, $C_2$–$C_6$ alkenyl, $C_1$–$C_4$ alkoxy, $C_1$–$C_4$ alkylthio, $C_1$–$C_4$ alkylsulfonyl, $C_2$–$C_6$ dialkylamino, nitro, $C_2$–$C_5$ carboalkoxy or cyano), or pyrimidyl (optionally substituted with 1–4 groups chosen from halogen, $C_1$–$C_4$ haloalkyl, $C_1$–$C_4$ alkyl, $C_2$–$C_6$ alkenyl, $C_1$–$C_4$ alkoxy, $C_1$–$C_4$ alkylthio, $C_1$–$C_4$ alkylsulfonyl, $C_2$–$C_6$ dialkylamino, nitro, $C_2$–$C_5$ carboalkoxy or cyano)

$R^{10}$ is H, $C_1$–$C_4$ alkyl or cyano;

$R^{11}$ is H, $C_1$–$C_4$ alkyl or halogen;

$R^{12}$ is H, $C_1$–$C_4$ alkyl or phenyl;

aryl is phenyl, biphenyl or naphthyl; and heteroaryl is pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl or pyrazolyl.

Compounds of formula I, other than those in which R5 and R6 are taken together and are O, S or NR12, are novel. This invention includes the novel compounds of formula I and pharmaceutical compositions containing them.

Preferred compounds for use in the method of this invention are compounds of formula (I) wherein:

X is $OR^1$, $NR^1R^2$, $CR^1R^2R^3$, or phenyl (optionally substituted at the 2-position with $CF_3$, nitro, halogen or cyano);

$R^1$ is $C_1$–$C_{12}$ alkyl, $C_2$–$C_{12}$ alkoxyalkyl, $C_3$–$C_{12}$ cycloalkyl, $C_4$–$C_{12}$ cycloalkylalkyl, aryl-($C_1$–$C_{12}$ alkyl), $C_3$–$C_{12}$ dialkylaminoalkyl, or phenyl (optionally substituted with 1–4 groups independently chosen from halogen, haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl);

$R^4$ is H or $C_1$–$C_4$ alkyl;

$R^5$ and $R^6$ are either H or $C_1$–$C_4$ alkyl;

$R^4$, $R^5$ and $R^6$ may also be taken together, along with the two interconnecting atoms, to constitute a tetrazole ring;

$R^9$ is phenyl (optionally substituted with 1–4 groups chosen from halogen, $C_1$–$C_4$ haloalkyl, $C_1$–$C_4$ alkyl, $C_2$–$C_6$ alkenyl, $C_1$–$C_4$ alkoxy, $C_1$–$C_4$ alkylthio, $C_1$–$C_4$ alkylsulfonyl, $C_2$–$C_6$ dialkylamino, nitro, $C_2$–$C_5$ carboalkoxy or cyano), 3-pyridyl (optionally substituted with 1–4 groups chosen from halogen, $C_1$–$C_4$ haloalkyl, $C_1$–$C_4$ alkyl, $C_2$–$C_6$ alkenyl, $C_1$–$C_4$ alkoxy, $C_1$–$C_4$ alkylthio, $C_1$–$C_4$ alkylsulfonyl, $C_2$–$C_6$ dialkylamino, nitro, $C_2$–$C_5$ carboalkoxy or cyano), or 5-pyrimidyl (optionally substituted with 1–4 groups chosen from halogen, $C_1$–$C_4$ haloalkyl, $C_1$–$C_4$ alkyl, $C_2$–$C_6$ alkenyl, $C_1$–$C_4$ alkoxy, $C_1$–$C_4$ alkylthio, $C_1$–$C_4$ alkylsulfonyl, $C_2$–$C_6$ dialkylamino, nitro, $C_2$–$C_5$ carboalkoxy or cyano);

$R^{10}$ is $CH_3$;

and $R^{11}$ is H.

More preferred compounds in this invention are of the formula (I) wherein:

A is N;

X is $NR^1R^2$ or $CR^1R^2R^3$;

$R^1$ is $C_1$–$C_6$ alkyl or $C_2$–$C_8$ alkoxyalkyl;

$R^2$ and $R^3$ are independently H, $C_1$–$C_6$ alkyl or $C_2$–$C_8$ alkoxyalkyl;

$R^4$ is H;

$R^5$ and $R^6$ are H;

$R^7$ and $R^8$ are independently H or $CH_3$;

and $R^9$ is phenyl (optionally substituted with 1–4 groups chosen from halogen, $C_1$–$C_4$ haloalkyl, $C_1$–$C_4$ alkyl, $C_2$–$C_6$ alkenyl, $C_1$–$C_4$ alkoxy, $C_1$–$C_4$ alkylthio, $C_1$–$C_4$ alkylsulfonyl, $C_2$–$C_6$ dialkylamino, nitro, $C_2$–$C_5$ carboalkoxy or cyano).

Specifically preferred because of their biological activity are the following compounds:

8-(2-bromo-4-isopropylphenyl)-4-(ethylbutylamino)-2-methyl-5,6,7,8-tetrahydropteridine;

8-(2-chloro-4,6-dimethoxyphenyl)-4-(ethylbutylamino)-2-methyl-5,6,7,8-tetrahydropteridine;

4-(ethylbutylamino)-2-methyl-8-(2,4,6-trimethylphenyl)-5,6,7,8-tetrahydropteridine;

and 4-(1-methoxy-2-butyl)amino-2-methyl-8-(2,4,6-trimethylphenyl)-5,6,7,8-tetrahydropteridine.

DETAILED DESCRIPTION OF THE INVENTION

Many compounds of this invention have one or more asymmetric centers or planes. Unless otherwise indicated, all chiral (enantiomeric and diastereomeric) and racemic forms are included in the present invention. Many geometric isomers of olefins, C=N double bonds, and the like can also be present in the compounds, and all such stable isomers are contemplated in the present invention. The compounds may be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "alkyl" includes both branched and straight-chain alkyl having the specified number of carbon atoms. "Alkenyl" includes hydrocarbon chains of either a straight or branched configuration and one or more unsaturated carbon-carbon bonds which may occur in any stable point along the chain, such as ethenyl, propenyl, and the like. "Alkynyl" includes hydrocarbon chains of either a straight or branched configuration and one or more triple carbon-carbon bonds which may occur in any stable point along the chain, such as ethynyl, propynyl and the like. "Haloalkyl" is intended to include both branched and straight-chain alkyl having the specified number of carbon atoms, substituted with 1 or more halogen; "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, and so forth. "Halo" or "halogen" includes fluoro, chloro, bromo, and iodo.

The term "substituted", as used herein, means that one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "appropriate amino acid protecting group" means any group known in the art of organic synthesis for the protection of amine or carboxylic acid groups. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1- methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

The term "amino acid" as used herein means an organic compound containing both a basic amino group and an acidic carboxyl group. Included within this term are natural amino acids, modified and unusual amino acids, as well as amino acids which are known to occur biologically in free or combined form but usually do not occur in proteins. Included within this term are modified and unusual amino acids, such as those disclosed in, for example, Roberts and Vellaccio (1983) *The Peptides*, 5: 342–429, the teaching of which is hereby incorporated by reference. Modified or unusual amino acids which can be used to practice the invention include, but are not limited to, D-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

The term "pharmaceutically acceptable salts" includes acid or base salts of the compounds of formulas (I) and (II). Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference. "Prodrugs" are considered to be any covalently bonded carriers which release the active parent drug of formula (I) or (II) in vivo when such prodrug is administered to a mammalian subject. Prodrugs of the compounds of formula (I) and (II) are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of formulas (I) and (II); and the like.

The term "therapeutically effective amount" of a compound of this invention means an amount effective to antagonize abnormal level of CRF or treat the symptoms of affective disorder, anxiety or depression in a host.

Synthesis

Synthesis of compounds of Formula (I) wherein A=N may begin with amidine compounds of Formula (II) (Scheme I), which are available commercially or synthetically from heating a nitrile compound and an ammonium salt. Compound (II) may then be condensed with a malonate ester (using conditions such as sodium in ethanol) to give a dihydroxy-pyrimidine compound of Formula (III). Nitration at the 5-position may be accomplished through the use of such conditions as concentrated nitric acid with or without the presence of another acid such as concentrated sulfuric or glacial acetic. The hydroxy groups of the nitrated compound of Formula (IV) may then be converted into leaving groups (Y), which include chloro, bromo, toluenesulfonate, or methanesulfonate. The dichloro compound (Formula (V), Y=Cl) may be prepared from the dihydroxy by a reagent such as phosphorus oxychloride, with or without the assistance of a catalyst such as diethylaniline. The bis (toluenesulfonate) compound (Formula (V), Y=OSO$_2$C$_6$H$_4$CH$_3$), may be prepared from the dihydroxy compound by treatment with a reagent such as toluenesulfonic anhydride. Careful addition one equivalent of a suitable form of a compound X—H to the compound of Formula (V) results in replacement of one of the Y groups with X. This is of particular utility when the X group represents a nucleophilic atom, such as nitrogen, sulfur or oxygen. Conditions which will facilitate this transformation include the optional presence of bases such as sodium hydride, triethylamine, diisopropylethylamine or Scheme I

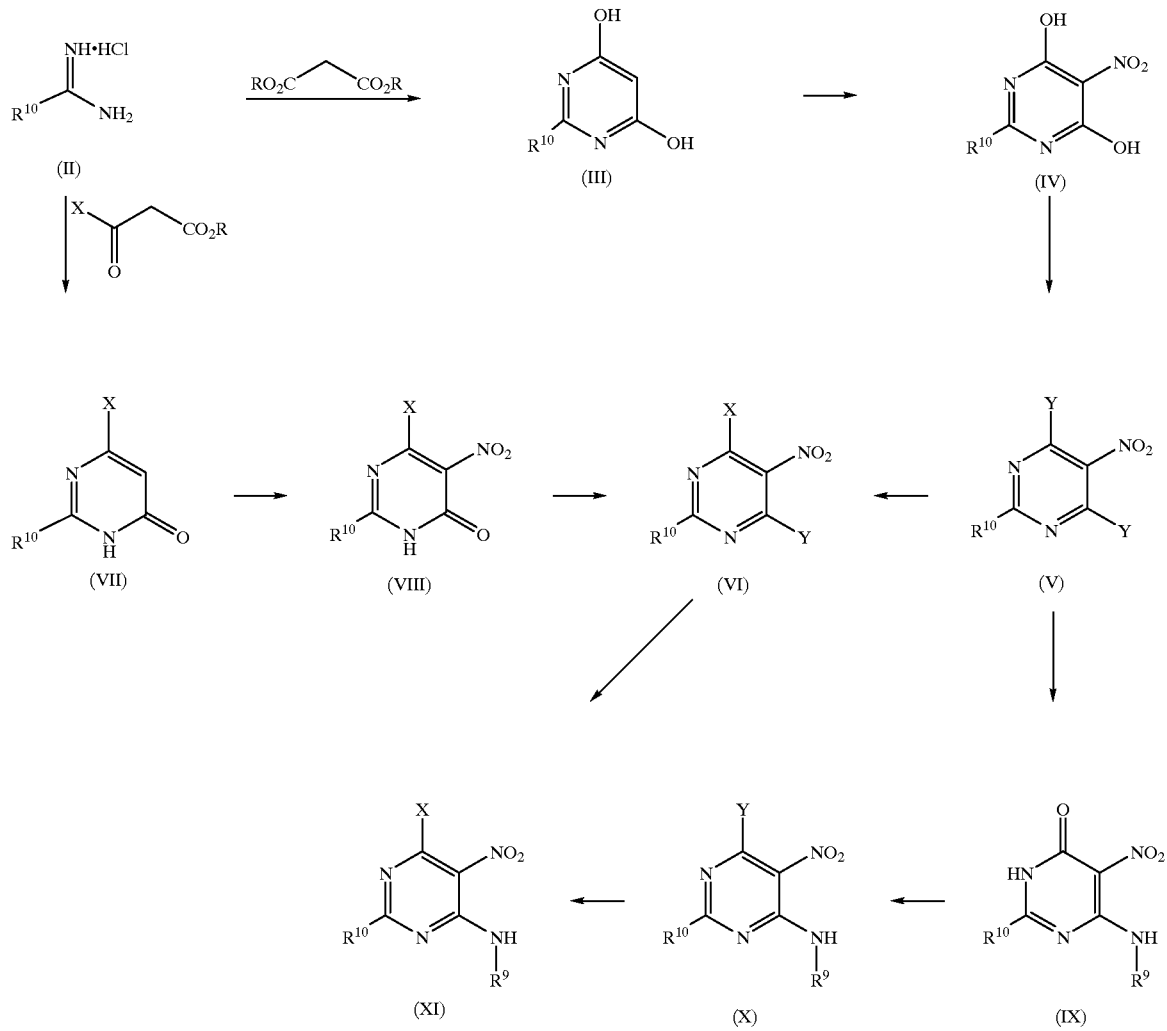

potassium carbonate, in solvents such as tetrahydrofuran, dimethylformamide, dimethylsulfoxide, methylene chloride, acetonitrile or ethanol, at appropriate temperatures.

Alternatively, in the case where X represents a group without a corresponding nucleophilic compound X—H being available, one may condense a compound of Formula (II) with an appropriately-substituted ketoester (using conditions similar to those for the malonate condensation) to obtain a compound of Formula (VII). Nitration conditions similar to those described above may then be used to prepare the nitro compound (VIII). Conversion of the pyrimidone group to the desired Y group may then be accomplished using the same conditions as described above for the transformation of (IV) to (V).

A third alternative involves treatment of the compound of Formula (V) with a compound $R^9$—$NH_2$. Conditions may be found for each Y group so that one Y group is replaced by $R^9$—NH, and the other is hydrolyzed to the pyrimidone (compound Formula (IX)). For example, for Y=Cl, this conversion may be effected by slow addition of a dimethylsulfoxide solution of one equivalent of $R^9$—$NH_2$ to a dimethylsulfoxide solution of compound (V), followed by aqueous workup. The pyrimidione of Formula (IX) may be converted to Y-bearing compound (Formula (X)) using the conditions described above for (IV) to (V). The Y group can then be replaced with X analogously to the transformation of (V) to (VI) to give a compound of Formula (XI).

Alternatively, the compound of Formula (VI) may be converted to the compound of Formula (XI) by treatment with the compound $R^9$—$NH_2$. Suitable conditions for this reaction include treatment with excess sodium hydride in refluxing toluene or heating the two compounds together in an alcoholic solvent (ethanol, propanol, butanol, ethylene glycol, ethoxyethoxyethanol) or other polar, aprotic solvents (such as dimethylformamide, 1,4-dioxane, dimethoxyethane or diglyme) without a base to effect the coupling.

Scheme II shows the appending of the second ring onto the pyrimidine ring. The nitro group in the compound of Formula (XI) can be reduced to an amino group using conditions such as sodium dithionite, catalytic hydrogenation, iron or zinc. The compound of Formula (XII) may be treated with a base such as sodium hydride (in solvents such as dimethylformamide, dimethyl sulfoxide, 1,4-dioxane, tetrahydrofuran, etc.), followed by a reagent of the general formula Y—$CR^7R^8$—$CO_2R$, where Y is halogen or psuedohalogen, and the structure of R is only important if Scheme II

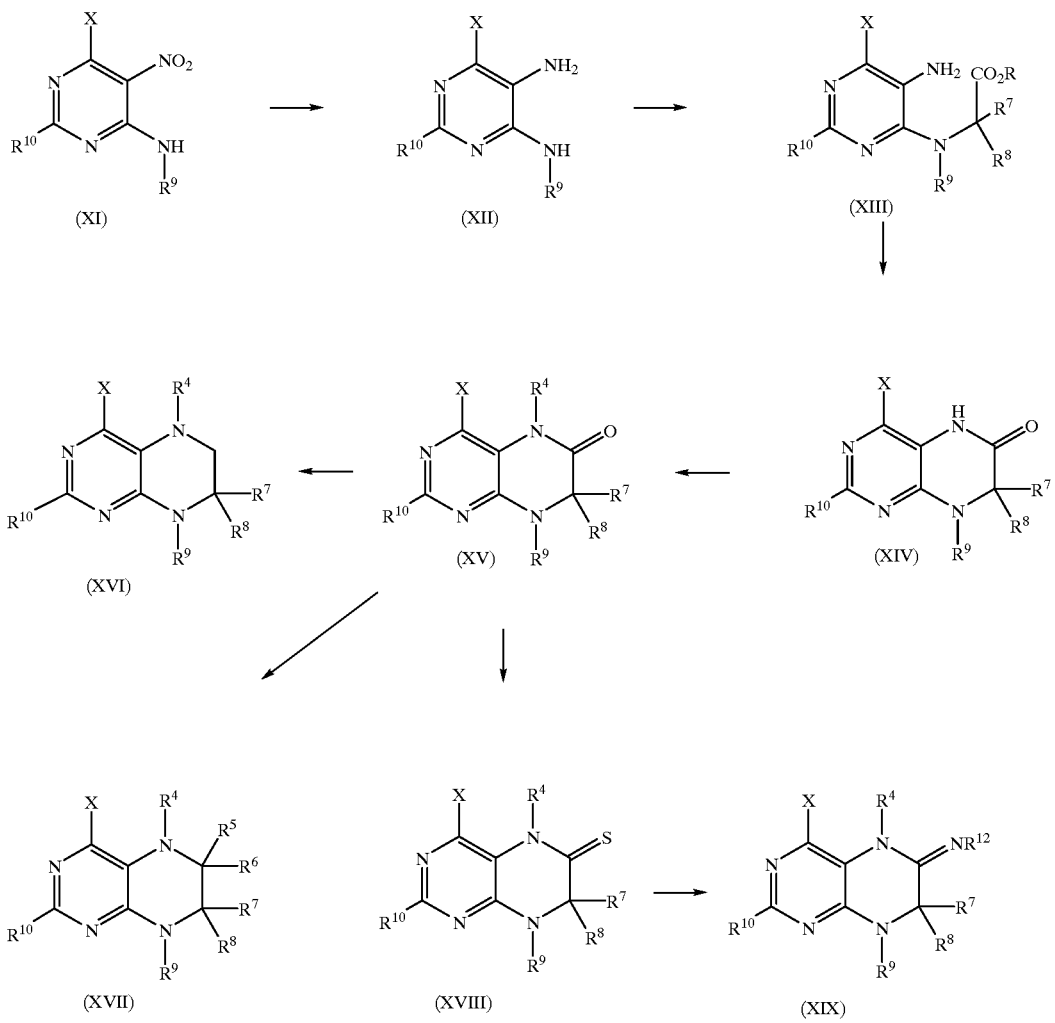

removal of the group prior to cyclization is desired. Cyclization of the compound of Formula (XIV) may be accomplished by heating in a solvent such as ethanol, dimethylformamide, etc. at temperatures ranging anywhere from ambient to the boiling point of the solvent. An additive such as an acid source (such as toluenesulfonic acid, aqueous hydrochloric, etc.), a base (triethylamine, sodium hydroxide, etc.) or a physical catalyst (such as molecular sieves) may be added, in quantities ranging from catalytic to stoichiometric to excess. In practice, the cyclization of (XIII) often is very facile, particularly in the case where R is lower alkyl, and will occur spontaneously in the reaction medium of the alkylation of compound (XII). Cyclized compound (XIV) may be alkylated with the $R^4$ group by first treatment with a base such as sodium hydride in a solvent such as dimethylformamide or dimethylsulfoxide, then an alkylating reagent (such as a halogen- or psuedohalogen-bearing compound) which provides the $R^4$ group, to provide the compound of Formula (XV). At this point, compounds derived from bromoacetate alkylation of compound (XII) can be alkylated with appropriate $R^7$ and $R^8$ by treatment with a strong base such as sodium hydride, lithium diisopropylamide or sodium hexamethyldisilazide, and then alkylating agents bearing the $R^7$ or $R^8$ groups, thus resulting in the compound of Formula (XV).

Compound (XV) is a key intermediate which may be used to generate variations of Formula (I). For example, the carbonyl group of compound (XV) may be reduced with reagents such as lithium aluminum hydride, borane (complexed with tetrahydrofuran or other suitable ligands) or diisobutylaluminum hydride, which will generate a compound of Formula (XVI). The carbonyl group may be substituted with $R^5$ and $R^6$ groups using appropriately-substituted organolithium or organomagnesium reagents, to prepare compounds of Formula (XVII). The carbonyl group of compound (XV) may be converted to thiocarbonyl by treatment with reagents such as Lawesson's Reagent or phosphorus pentasulfide in appropriate solvents (toluene, benzene, etc.). The thioamide group of compound (XVIII) may be converted to amidine using the method of Robba et al. (*Tetrahedron Letters* 1992, 33, 2803–2804), which involves treatment with an amine of formula $R^{11}$—$NH_2$ and a catalyst such as a mercury (II) salt. This will result in the synthesis of a compound of Formula (XIX).

Compounds of Formula (I) composed of a fused pyridine ring (A=CH) may be prepared using very similar technology to that presented in Scheme II. In this case, however, the starting material is not of the structure (XI), but rather

Scheme III

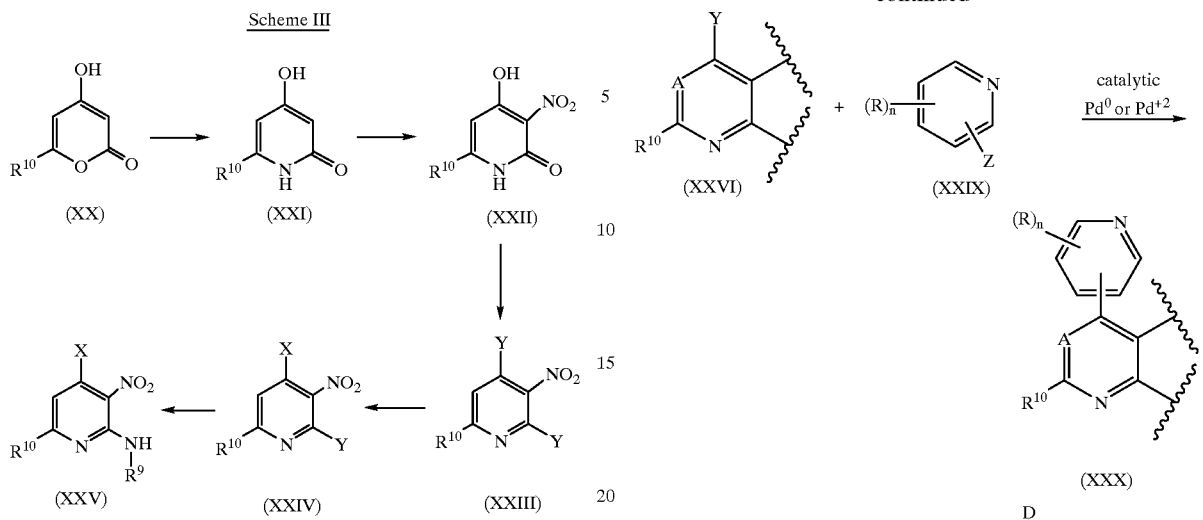

of structural formula (XXV) (Scheme III). This compound may be prepared starting with a lactone compound of Formula (XX), which are available by dimerization of a ketoester $R^{10}C(=O)CH_2CO_2Et$ according to the method of Arndt (*Org. Syn., Coll. Vol. III*, p. 231), followed by deacylation according to the method of Collie et al. (*J. Chem. Soc.* 1907, 91, p. 787 and references therein). The ring oxygen atom may be replaced with nitrogen by treatment with conc. aq. ammonium hydroxide, according to the method of Wang (*J. Heterocylic Chem.* 1970, 1, 389–392). Compound (XXI) may be nitrated similarly to the transformation of compound (III) to give compound (XXII). The hydroxy groups of compound (XXII) may be converted to leaving groups Y using the techniques discussed above for the conversion of compound (IV) to (V). The $C^4$ Y group may be selectively replaced with a nucleophilic X group, and the other Y group in compound (XXIV) may be replaced with $NHR^9$ by treatment with a compound $R^9NH_2$, either with no solvent or an appropriate solvent (such as a high-boiling alcohol) at temperatures sufficiently elevated to effect coupling. Compound (XXV)

Scheme IV

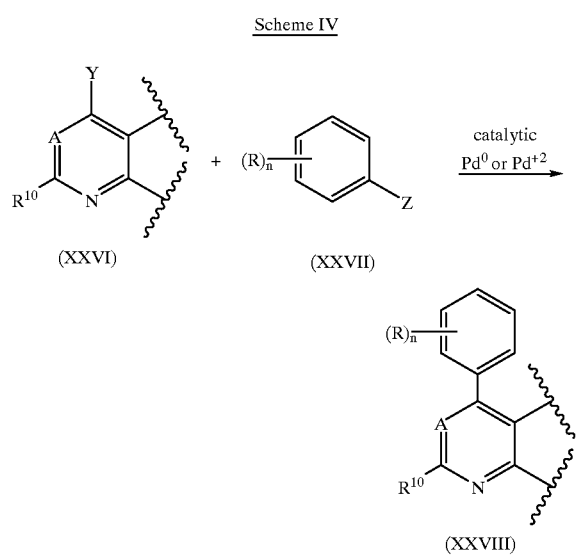

may then be employed in the same general way as for compound (XI) to generate compounds of Formula (I).

Further functionalization of this class of compounds may be achieved using a compound of Formula (XXVI) (Scheme IV), which represents some pyridine or pyridine compound (either uncyclized, like compounds (XI) or (XXV), or a cyclized compound) bearing a leaving group Y. The Y group may be replaced with phenyl or pyridyl using coupling reactions employing a phenyl (or pyridyl) compound of Formula (XXVII) (or (XXIX)) and an appropriate palladium catalyst. For example, arylboronic acids ($Z=B(OH)_2$) may be coupled to a heterocyclic halide using catalytic amounts of tetrakis(triphenylphosphine)palladium, which is the method of Suzuki, et al. (*Synthetic Communications* 1981, 11, p. 513–519). Other appropriate reagents for this coupling reaction includes organomagnesium ($Z=MgBr$ or $MgCl$) reagents (with nickel (II) chloride catalysis according to the method of Sugimori et al., *Synthetic Communications* 1991, 21, p. 481–487) or organozinc ($Z=ZnCl$) reagents (according to the method of Negishi et al., *J. Org. Chem.* 1977, 42, p. 1821–1823).

Other carbon substituents may be introduced into compound (XXVI) by treatment with a sodium salt (generated by the use of a base such as sodium ethoxide or sodium hydride) of an active methylene or methine reagent (i.e. where B and D are groups which stabilize adjacent anions, such as keto, carboalkoxy, cyano, alkyl- or aryl-sulfonyl, etc.). The resulting compounds of Formula (XXXI) may be further modified by conversion of the B and D groups into $R^2$ and $R^3$ groups. Those skilled in the art of organic synthesis should readily understand possible variations of these conversions to prepare a number of different $R^1$, $R^2$ and $R^3$ group substituents.

Preparation of compounds of Formula (I) wherein the $R^1$ and $R^4$ groups are taken together to form a ring may be accomplished beginning from a compound of Formula (XXXIII) (Scheme V), where X' is meant to designate a group $NHR^2$, OH, SH or $CHR^2R^3$. This compound may be treated with a base (such as sodium hydride) in an appropriate solvent, followed by a reagent bearing reactive terminii on both ends (for example, a dihaloalkane, a haloester, etc.). The X' and amide NH groups will couple with such a reagent under these conditions to form the third ring of compound (XXXIV). The amide group may then be modified as described above to give then final product of Formula (XXXV).

Compounds of Formula (I) wherein the $R^4$, $R^5$ and $R^6$ groups are taken together to form a heteroaromatic ring may be prepared using the strategy displayed in Scheme VI. Compound (XIV) may be converted to amidine (XXXVI), using the conditions described above for the preparation of compound (XIX). The amidine is treated with an α-halo- or α-hydroxyketone, under conditions such as refluxing alcohol, to afford the imidazole compound (XXXVII). Compound (XIV) may be converted to fused tetrazole compound (XXXVIII) using the conditions of Duncia et al. (*J. Org. Chem.* 1991, 56, p. 2395).

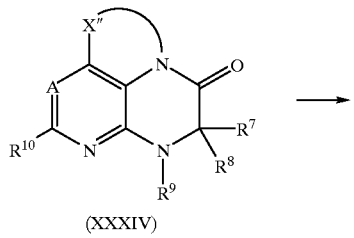

(XXXIV)

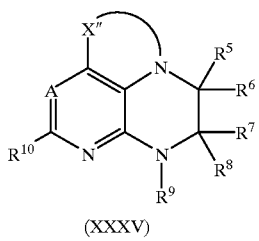

(XXXV)

Scheme V

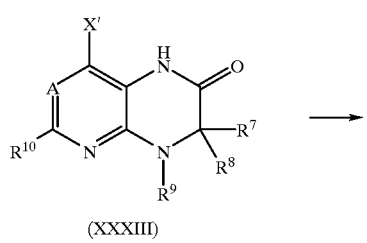

(XXXIII)

Scheme VI

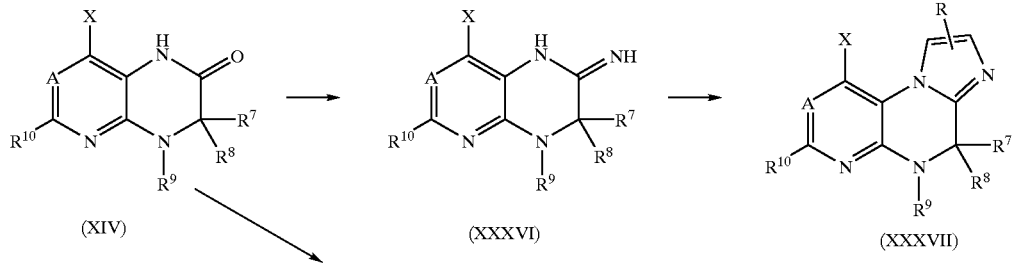

(XIV)   (XXXVI)   (XXXVII)

-continued

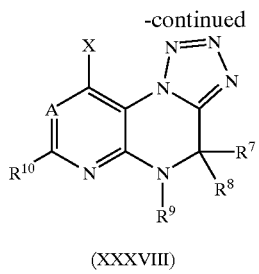

(XXXVIII)

The experimental methods listed below for Examples 1, 17, 24, 42, 131, 143, 155, and 248 may be used in the preparation of all the compounds shown in Tables I (pyrimidines) and II (pyridines).

EXAMPLE 1

Preparation of 8-(2-bromo-4-isopropylphenyl)-4-(ethylbutylamino)-2-methyl-5,6,7,8-tetrahydropteridin-6-one Part A. A solution of 4,6-dichloro-2-methyl-5-nitropyrimidine (prepared using the methods of Albert, et al., *J. Chem. Soc.* 1954, p. 3832) (2.77 g, 13.3 mmol) in absolute ethanol (25 mL) was cooled to 0° C., and treated with triethylamine (2.00 mL, 14.3 mmol). Then, a solution of ethylbutylamine (1.80 mL, 13.2 mmol) in ethanol (3 mL) was added dropwise with stirring. The mixture was allowed to stir and warm to ambient temperature overnight, then was partitioned between water and ethyl acetate (100 mL each). The organic phase was seperated, washed with satd. aq. brine (100 mL), dried over anhydrous sodium sulfate, filtered and evaporated. The residue was separated by column chromatography (silica gel, dichloromethane) to afford 4-chloro-6-(ethylbutylamino)-2-methyl-5-nitropyrimidine as an oil (3.34 g, 12.2 mmol, 92%). Spectral data: TLC $R_F$ 0. 59 (dichloromethane). $^1$H NMR (300 MHz, CDCl$_3$): δ 3.45 (2H, q, J=7.0 Hz), 3.38 (2H, t, J=7.7 Hz), 2.50 (3H, s), 1.62–1.52 (2H, m), 1.38–1.26 (2H, m), 1.20 (3H, t, J=7.0 Hz), 0.94 (3H, t, J=7.3 Hz). MS (NH$_3$—CI): m/e 276 (4), 275 (40), 274 (16), 273 (100).

Part B. The product of Part A above (2.97 g, 10.9 mol) was dissolved in ethoxyethoxyethanol solution (11 mL), and treated with 2-bromo-4-isopropylaniline (2.34 g, 10.9 mmol). The mixture was heated to 120° C. for 4 h, then cooled and partitioned between water and ethyl acetate (100 mL each). The organic layer was separated and washed with two additional portions of water (100 mL each) and brine (100 mL). The aqueous phases were all back-extracted in sequence with more ethyl acetate (100 mL). The extracts were combined, dried over sodium sulfate, filtered and evaporated. The residue was separated by column chromatography (silica gel, 5:95 ethyl acetate-hexane) to afford 6-(2-bromo-4-isopropylphenylamino)-4-(ethylbutylamino)-2-methyl-5-nitropyrimidine as an oil (3.05 g, 6.77 mmol, 62%). Spectral data: TLC $R_F$ 0.56 (20:80 ethyl acetate-hexane).

$^1$H NMR (300 MHz, CDCl$_3$): δ 10.30 (1H, br s), 8.32 (1H, d, J=8.4 Hz), 7.45 (1H, d, J=1.8 Hz), 7.19 (1H, dd, J=8.4, 1.8 Hz), 3.52–3.42 (4H, m), 2.88 (1H, heptet, J=7.0 Hz), 2.40 (3H, s), 1.70–1.58 (2H, m), 1.39–1.29 (2H, m), 1.26 (3H, t, obscurred), 1.25 (6H, d, J=7.0 Hz), 0.94 (3H, t, J=7.1 Hz). MS (NH$_3$—CI): m/e 454 (4), 453 (24), 452 (100), 451 (26), 450 (99).

Part C. The product of Part B above (256 mg, 568 μmol) was dissolved in 1:1 dioxane-water (3 mL), and treated with conc. aq. ammonium hydroxide (0.5 mL). To this was added, with stirring, solid sodium dithionite (440 mg, 2.53 μmol) in 3 portions over 1 h. The resulting solution was allowed to stir for an additional 8 h, then partitioned between water and ethyl acetate (100 mL). The organic layer was washed with brine, dried over sodium sulfate, filtered and evaporated. The residual material was purified by elution through a short plug of silica gel (20:80 ethyl acetate-hexane), and evaporation gave pure 5-amino-6-(2-bromo-4-isopropylphenylamino)-4-(ethylbutylamino)-2-methylpyrimidine as an oil (198 mg, 472 μmol, 83%). Spectral data: TLC $R_F$ 0.26 (10:90 ethyl acetate-hexane). $^1$H NMR (300 MHz, CDCl$_3$): δ 8.15 (1H, d, J=8.4 Hz), 7.38 (1H, d, J=2.2 Hz), 7.15 (1H, dd, J=8.4, 2.2 Hz), 7.04 (1H, br s), 3.30–3.19 (4H, m), 3.08 (2H, br s), 2.85 (1H, heptet, J=7.0 Hz), 2.47 (3H, s), 1.57–1.44 (2H, m), 1.39–1.26 (2H, m), 1.23 (6H, d, J=7.0 Hz), 1.11 (3H, t, J=7.0 Hz), 0.91 (3H, t, J=7.1 Hz). MS (NH$_3$—CI): m/e 424 (3), 423 (24), 422 (100), 421 (26), 420 (100).

Part D. Sodium hydride dispersion in mineral oil (0.26 g w/w, 5.42 mmol) was washed with hexane, and the hexane was decanted off. The remaining solid was dried under vacuum and suspended in anhydrous dimethylformamide (5 mL). The resulting suspension was cooled in an ice bath, while the product of Part C above (1.78 g, 4.23 mmol) in dimethylfomamide solution (5 mL) was added slowly by syringe. After hydrogen evolution was complete, the mixture was treated slowly with ethyl bromoacetate (0.47 mL, 4.24 mmol) by syringe, and the mixture was allowed to stir for 10 h. It was partitioned between water and ethyl acetate (100 ML each), and the organic phase was washed with two additional portions of water (100 mL each) and brine (100 ML). The aqueous phases were back-extracted in sequence with ethyl acetate (100 mL), and the extracts were combined, dried over sodium sulfate, filtered and evaporated. The residue was separated by column chromatography (silica gel, 10:90 ethyl acetate-hexane) to afford the title product as a solid (1.35 g, 2.93 mmol, 69%). Spectral data: m.p. 146–147° C. TLC $R_F$ 0.49 (50:50 ethyl acetate-hexane). $^1$H NMR (300 MHz, CDCl$_3$): δ 7.53 (1H, s), 7.36 (1H, br s), 7.25 (2H, s), 4.44 (1H, d, J=15 Hz), 4.25 (1H, d, J=15 Hz), 3.29–3.15 (4H, m), 2.94 (1H, heptet, J=7.0 Hz), 2.29 (3H, s), 1.54–1.45 (2H, m), 1.39–1.29 (2H, m), 1.28 (6H, d, J=7.0 Hz), 1.11 (3H, t, J=7.1 Hz), 0.92 (3H, t, J=7.1 Hz). MS (NH$_3$—CI): m/e 464 (3), 463 (24), 462 (100), 461 (26), 460 (99). Analysis calc'd for $C_{22}H_{30}BrN_5O$: C, 57.39; H, 6.58; N, 15.21; found: C, 56.74; H, 6.02; N, 14.41.

EXAMPLES 143 and 155

Preparation of 8-(2-bromo-4-isopropylphenyl)-2,5-dimethyl-4-(ethylbutylamino)-5,6,7,8-tetrahydropteridin-6-one and 8-(2-bromo-4-isopropylphenyl)-4-(ethylbutylamino)-2,5,7-trimethyl-5,6,7,8-tetrahydropteridin-6-one Part A. Sodium hydride suspension in mineral oil (200 mg of 50% w/w, 4.17 mmol) was washed with hexane, dried under vacuum and suspended in anhydrous dimethylformamide (5 mL). This suspension was cooled to 0° C., while a solution of the compound of Example 1 (1.58 g, 3.43 mmol) in dimethylformamide (5 mL) was added slowly by syringe. The resulting mixture was allowed to stir for 1 h, then was treated with methyl iodide (0.30 mL, 4.82 mmol) by syringe. The mixture was allowed to stir overnight, then was partitioned between water and ethyl acetate (100 mL each). The organic phase was washed with two additional portions of water and one of brine solution. The aqueous fractions were back-extracted in sequence with more ethyl acetate, and the organic layers were combined, dried over sodium sulfate, filtered and evaporated. The residual oil was separated by column chromatography (silica gel, 10:90 ethyl acetate-hexane) to afford two fractions. The first compound off the column was the title compound of Example 155 (150 mg, 0.31 mmol, 9%): TLC $R_F$ 0.29 (20:80 ethyl acetate-hexane). $^1$H NMR (300 MHz, CDCl$_3$): δ 7.50 (1H, d, J=1.8 Hz), 7.33 (1H, d, J=8.0 Hz), 7.21 (1H, dd, J=8.0, 1.8 Hz), 4.23 (1H, q, J=7.3 Hz), 3.22 (3H, s), 3.19 (4H, br), 2.92 (1H, heptet, J=7.0 Hz), 2.30 (3H, s), 1.55 (2H, br), 1.43–1.00 (8H, br), 1.27 (6H, d, J=7.0 Hz), 0.91 (3H, br t, J=7 Hz). MS (NH$_3$—CI): m/e 492 (3), 491 (28), 490 (96), 489 (30), 488 (100). The second compound off the column was the title compound of Example 143 (1.30 g, 2.74 mmol, 80%): TLC $R_F$ 0.22 (20:80 ethyl acetate-hexane). $^1$H NMR (300 MHz, CDCl$_3$): δ 7.48 (1H, s), 7.21 (2H, s), 4.19 (2H, br), 3.21 (3H, s), 3.18 (4H, v br), 2.91 (1H, heptet, J=6.6 Hz), 2.30 (3H, s), 1.55–1.46 (2H, m), 1.35–1.25 (2H, m), 1.27 (6H, d, J=6.6 Hz), 1.11 (3H, br t, J=7.0 Hz), 0.90 (3H, t, J=7.0 Hz). MS (NH$_3$—CI): m/e 478 (3), 477 (28), 476 (98), 475 (30), 474 (100).

EXAMPLE 24

Preparation of 8-(2-bromo-4-isopropylphenyl)-4-(ethylbutylamino)-2-methyl-5,6,7,8-tetrahydropteridine A solution of the compound of Example 1 (650 mg, 1.41 mmol) in anhydrous tetrahydrofuran (5 mL) was treated with a tetrahydrofuran solution of borane (3 mL, 1 M, 3 mmol). The resulting solution was allowed to stir for 20 h, then was delivered slowly to stirring aq. 1 N sodium bicarbonate (10 mL). The mixture was stirred until gas evolution was complete, then was extracted with dichloromethane (twice 30 mL). The organic extracts were combined, dried over sodium sulfate, filtered and evaporated. The residual material was purified by elution through a short plug of silica gel (30:70 ethyl acetate-hexane), and evaporation gave the pure title product as an oil (429 mg, 1.04 mmol, 74%). Spectral data: TLC $R_F$ 0.50 (30:70 ethyl acetate-hexane). $^1$H NMR (300 MHz, CDCl$_3$): δ 7.50 (1H, d, J=1.8 Hz), 7.24 (1H, d, J=8.4 Hz), 7.18 (1H, dd, J=8.4, 1.8 Hz), 3.88–3.39 (5H, br m), 3.22–3.09 (4H, m), 2.91 (1H, heptet, J=7.0 Hz), 2.25 (3H, s), 1.52–1.41 (2H, m), 1.38–1.24 (2H, m), 1.27 (6H, d, J=7.0 Hz), 1.08 (3H, t, J=7.1 Hz), 0.91 (3H, t, J=7.0 Hz). MS (ESI): m/e 450 (3), 449 (23), 448 (98), 447 (25), 446 (100). A solid derivative was obtained by precipitation of the hydrochloride salt from ether, melting point 79–81° C.

EXAMPLE 17

Preparation of 8-(2-bromo-4-isopropylphenyl)-2-methyl-4-(2-trifluoromethylphenyl)-5,6,7,8-tetrahydropteridin-6-one Part A. A solution of 2-trifluoromethylphenylboronic acid (prepared according to the methods described in the review by N. Miyaura and A. Suzuki, *Chem. Rev.* 1995, 95, p. 2457) (1.00 g, 5.27 mmol), 4,6-dichloro-2-methyl-5-nitropyrimidine (0.91 g, 4.39 mmol) and tetrakis(triphenylphosphine) palladium (147 mg) in benzene (15 mL) was treated with aq. sodium carbonate solution (6 mL, 1 M). This mixture was heated to reflux for 6 h, then cooled and partitioned between water and ethyl acetate (60 mL each). The organic layer was washed with brine, and the aqueous layers were back-extracted in sequence with more ethyl acetate. The organic extracts were combined, dried over sodium sulfate, filtered and evaporated. The residue was separated by column chromatography (silica gel, 15:85 ethyl acetate-hexane) to afford 4-chloro-2-methyl-5-nitro-6-(2-trifluoromethylphenyl)pyrimidine (0.64 g, 2.01 mmol, 38%) as a waxy solid. Spectral data: $R_F$ 0.40 (20:80 ethyl acetate-hexane). $^1$H NMR (300 MHz, CDCl$_3$) δ 7.84–7.81 (1H, m), 7.69–7.63 (2H, m), 7.38–7.35 (1H, m), 2.84 (3H, s). MS (NH$_3$—CI) m/e 320 (24), 319 (26), 318 (100).

Part B. A solution of the compound prepared in Part A above (1.07 g, 3.37 mmol) and 2-bromo-4-isopropylaniline (0.87 g, 4.04 mmol) in tetrahydrofuran (20 mL) was heated to reflux for 5 h, then cooled and poured into 100 mL ethyl acetate. This was washed with aq. sodium bicarbonate solution (100 mL, 1 N) and brine, then dried over sodium sulfate, filtered and evaporated. The resulting solid was triturated with 1:1 petroleum ether-diethyl ether, filtered and dried under vacuum to afford pure 4-(2-bromo-4-isopropylphenylamino)-2-methyl-5-nitro-6-(2-trifluoromethylphenyl)pyrimidine (1.51 g, 3.05 mmol, 90%). Spectral data: m.p. 152–154° C. $R_F$ 0.37 (20:80 ethyl acetate-hexane). $^1$H NMR (300 MHz, CDCl$_3$) δ 10.20 (1H, br s), 8.26 (1H, d, J=8.4 Hz), 7.78 (1H, d, J=7.7 Hz), 7.65–7.57 (2H, m), 7.52 (1H, d, J=1.8 Hz), 7.35 (1H, d, J=7.0 Hz), 7.28 (1H, br s), 2.93 (1H, m), 2.66 (3H, s), 1.29 (6H, d, J=7.0 Hz). MS (NH$_3$—CI) m/e 498 (24), 497 (100), 496 (28), 495 (100).

Part C. The same procedure used for the reduction of a nitro group in Example 1, Part C was employed here. Thus, the compound of Part B above was converted to 5-amino-4-(2-bromo-4-isopropylphenylamino)-2-methyl-6-(2-trifluoromethylphenyl) pyrimidine in 32% yield. Spectral data: $R_F$ 0.11 (20:80 ethyl acetate-hexane). $^1$H NMR (300 MHz, CDCl$_3$) δ 8.58 (1H, d, J=8.4 Hz), 7.83 (1H, d, J=7.7 Hz), 7.67–7.58 (3H, m), 7.43 (1H, d, J=1.8 Hz), 7.41 (1H, s), 7.25 (1H, dd, J=8.4, 1.8 Hz), 2.89 (1H, m), 2.83 (2H, br s), 2.59 (3H, s), 1.26 (6H, d, J=7.0 Hz). MS (NH$_3$—CI) m/e 468 (24), 467 (100), 466 (30), 465 (99).

Part D. The same procedure used for the cyclization reaction of Example 1, Part D was employed here. Thus, the compound of Part C above was converted to the title compound in 60% yield. Spectral data: m.p. 238–239° C. $R_F$ 0.20 (50:50 ethyl acetate-hexane). $^1$H NMR (300 MHz, CDCl$_3$) d 7.85 (1H, d, J=8.4 Hz), 7.73–7.59 (3H, m), 7.48–7.41 (1H, m), 7.33 (1H, s), 7.30 (1H, s), 7.00 (1H, br s), 4.46 (1H, d, J=16.8 Hz), 4.42 (1H, d, J=16.8 Hz), 2.97 (1H, m), 2.40 (3H, s), 1.31 (6H, d, J=6.6 Hz). MS (NH$_3$—CI) m/e 508 (26), 507 (100), 506 (30), 505 (99).

EXAMPLE 42

Preparation of Diethyl 2-[8-(2-bromo-4-isopropylphenyl)-2-methyl-6-oxo-5,6,7,8-tetrahydropteridin-4-yl]malonate Sodium hydride suspension in mineral oil was washed with hexane and dried under vacuum, then taken up in tetrahydrofuran. This mixture is cooled to 0° C., and treated with diethyl malonate (1.1 eq.). After the evolution of hydrogen gas is complete, the resulting solution is treated with 8-(2-bromo-4-isopropylphenyl)-4-chloro-2-methyl-5,6,7,8-tetrahydropteridin-6-one (see Example SF445, Part A, below; 1.0 eq.). The solution is heated to reflux until thin-layer chromatography shows the consumption of the starting material is nearly complete. The mixture is allowed to cool, and poured into saturated aqueous ammonium chloride solution. This is extracted twice with ethyl acetate, and the extracts are washed with brine, combined, dried over sodium sulfate, filtered and evaporated. The residue is separated by column chromatography to afford the title product.

EXAMPLE 131

Preparation of 8-(2-bromo-4-isopropylphenyl)-4-(ethylbutylamino)-2-methyl-5,6,7,8-tetrahydropteridin-6-thione A solution of the compound of Example 1 (323 mg, 0.70 mmol) in toluene (10 mL) was treated with Lawesson's Reagent (170 mg, 0.42 mmol). The resulting mixture was heated to reflux for 6 h, then cooled and evaporated. The residue was separated by column chromatography (silica gel, 10:90 ethyl acetate-hexane) to afford the title product, which was purified by recrystallization from ethyl acetate-hexane (280 mg, 0.59 mmol, 84%). Spectral data: m.p. 148–149° C. (ether-hexane). TLC $R_F$ 0.31 (20:80 ethyl acetate-hexane). $^1$H NMR (300 MHz, CDCl$_3$): δ 9.01 (1H, br s), 7.51 (1H, s), 7.22 (2H, s), 4.77 (1H, br d, J=15.7 Hz), 4.56 (1H, br d, J=15.7 Hz), 3.40–3.22 (4H, m), 2.92 (1H, heptet, J=7.0 Hz), 2.29 (3H, s), 1.62–1.52 (2H, m), 1.40–1.30 (2H, m), 1.28 (6H, d, J=7.0 Hz), 1.18 (3H, t, J=7.0 Hz), 0.95 (3H, t, J=7.3 Hz). MS (NH$_3$—CI): m/e 479 (26), 478 (100), 477 (30), 476 (95). Analysis calc'd for C$_{22}$H$_{30}$BrN$_5$S: C, 55.46; H, 6.36; N, 14.70; found: C, 55.54; H, 6.38; N, 14.37.

EXAMPLE 248

Preparation of 8-(2-bromo-4-isopropyl-phenyl)-4-(ethylbutylamino)-2-methyl-5,6,7,8-tetrahydropteridin-6-imine The method of Robba et al., *Tetrahedron Letters* 1992, 33, p. 2803–2804 may be used here. Thus, a solution of the compound of Example 131 in tetrahydrofuran (0.5 M) is warmed to 55° C., and treated with 1.5 equivalents of mercuric chloride. Then, ammonia gas is bubbled in, and addition is continued until five minutes after the appearance of precipitating mercuric sulfide. The reaction mixture is allowed to stir for an additional hour, then is cooled, filtered through celite and evaporated. The residue is triturated with a small amount of water, filtered and dried to afford the title compound.

Modifications of the procedures presented below for Examples 501, 698 and 704 may be used to prepare many of the compounds listed in Table III.

EXAMPLE 501

Preparation of 10-[2-bromo-4-(1-methylethyl) phenyl]-4-butyl-9,10-dihydro-2-methyl-4H,8H-pyrazino[3,2,1-de]pteridine-5,8(6H)-dione Part A. Sodium hydride (mineral oil dispersion, 48 mg, 1.00 mmol) was washed with hexane, dried under vacuum, and taken up in dimethylformamide (5 mL). To this was added with stirring a solution of 5-amino-4-(2-bromo-4-isopropylphenylamino)-6-chloro-2-methylpyrimidine (311 mg, 0.87 mmol) in dimethylformamide (5 mL). After stirring for 30 min., the mixture was treated with ethyl bromoacetate (0.10 mL, 0.90 mmol) in one portion. The mixture was allowed to stir for 18 h, then poured into water (100 mL). This was extracted twice with ethyl acetate (100 mL each), and the organic extracts were washed in sequence with two portions of water (100 mL each) and brine (100 mL), then combined, dried over sodium sulfate, filtered, and evaporated. The residual material was separated by column chromatography (silica gel, 20:80 ethyl acetate-hexane) to afford two fractions, the first being ethyl (8-(2-bromo-4-isopropylphenyl)-4-chloro-2-methyl-6-oxo-5,6,7,8-tetrahydropteridin-5-yl)acetate (89 mg, 0.18 mmol, 21%), the second being 8-(2-bromo-4-isopropylphenyl)-4-chloro-2-methyl-5,6,7,8-tetrahydropteridin-6-one (89 mg, 0.22 mmol, 26%). Spectral data for the first fraction: TLC $R_F$ 0.25 (30:70 ethyl acetate-hexane). $^1$H NMR (300 MHz, CDCl$_3$): δ 7.53 (1H, d, J=1.8 Hz), 7.26 (1H, dd, J=8.4, 1.8 Hz), 7.22 (1H, d, J=8.4 Hz), 4.88 (1H, d, J=15 Hz), 4.84 (1H, d, J=15 Hz), 4.47 (1H, d, J=15.4 Hz), 4.27 (1H, d, J=15.4 Hz), 4.25 (2H, q, J=7.3 Hz), 2.95 (1H, heptet, J=7.0 Hz), 2.38 (3H, s), 1.29 (3H, t, J=7.3 Hz), 1.28 (6H, d, J=7.0 Hz). MS (NH$_3$—CI): m/e 486 (6), 485 (26), 484 (23), 483 (100), 482 (18), 481 (76).

Part B. A solution of the first fraction from Part A above (89 mg, 0.18 mmol) in butylamine (1.0 mL, 10.1 mmol) was treated with glacial acetic acid (0.011 mL, 0.19 mmol), and the resulting solution was heated to reflux for 20 h. The mixture was cooled and evaporated, and the residue was separated by column chromatography (silica gel, 15:85 ethyl acetate-hexane) to afford the title compound as a solid (50 mg, 0.10 mmol, 57%). Spectral data: m.p. 207–208° C. TLC $R_F$ 0.29 (30:70 ethyl acetate-hexane). $^1$H NMR (300 MHz, CDCl$_3$): δ 7.54 (1H, d, J=1.8 Hz), 7.27 (1H, dd, J=8.4, 1.8 Hz), 7.23 (1H, d, J 8.4 Hz), 4.66 (1H, d, J=18.6 Hz), 4.55 (2H, br d, J=17 Hz), 4.32 (1H, d, J=16.5 Hz), 4.12 (2H, t, J=7.5 Hz), 2.95 (1H, heptet, J=7.0 Hz), 2.33 (3H, s), 1.70–1.59 (2H, m), 1.45–1.35 (2H, m), 1.29 (6H, d, J=7.0 Hz), 0.96 (3H, t, J=7.1 Hz). MS (NH$_3$—CI): m/e 476 (4), 475 (25), 474 (100), 473 (27), 472 (99). Analysis calc'd for C$_{22}$H$_{26}$BrN$_5$O$_2$: C, 55.94; H, 5.56; N, 14.83; found: C, 54.13; H, 5.34; N, 13.98.

EXAMPLE 698

Preparation of Diethyl 4-[2-bromo-4-(1-methylethyl)phenyl]-5,6,9,10-tetrahydro-2-methyl-6-oxo-4H,8H-pyrido[3,2,1-de]pteridine-10,10-dicarboxylate Sodium hydride dispersion is washed free of oil with hexane and dried under vacuum. Dimethylformamide is added, and the mixture is cooled to 0° C. A solution of the compound of Example 42 (0.45 eq. based on the sodium hydride) in dimethylformamide is added, and the mixture is stirred for one hour. Then, a solution of 1,2-dibromoethane (1.0 eq. based on the substrate) in dimethylformamide is added dropwise slowly. The mixture is allowed to stir overnight, then is poured into water. The resulting mixture is extracted twice with ethyl acetate, and the extracts are twice more washed with water in sequence, then brine, then combined, dried over sodium sulfate, filtered and evaporated. The residue is separated by column chromatography to give the title product.

EXAMPLE 704

Preparation of 4-[2-bromo-4-(1-methylethyl) phenyl]-5.6,9,10-tetrahydro-10,10-bis(methoxymethyl)-2-methyl-4H,8H-pyrido[3,2,1-de] pteridine Part A. A solution of the compound of Example 698 in methylene chloride is cooled to 0° C., and a solution of diisobutylaluminum hydride (7 eq.) in methylene chloride is slowly added by syringe. The mixture is allowed to stir and warm to ambient temperature until the substrate is consumed, then the reaction mixture is slowly delivered to stirring ice-cold 1 N HCl solution. The mixture is then neutralized to pH 7 with solid sodium bicarbonate, and extracted twice with methylene chloride. The extracts are combined, dried over sodium sulfate, filtered and evaporated. The residue is separated by column chromatography to afford 4-[2-bromo-4-(1-methylethyl)phenyl]-5,6,9,10-tetrahydro-10,10-bis(hydroxymethyl)-2-methyl-4H,8H-pyrido[3,2,1-de]pteridine.

Part B. Sodium hydride dispersion is washed free of oil with hexane, and dried under vacuum. Dimethylformamide is added, the suspension is cooled to 0° C., and a solution of the compound of Part A above in dimethylformamide is slowly added. After stirring for 1 h, the mixture is treated with 2 eq. methyl iodide. The mixture is allowed to stir for at least 6 h, then poured into water. This is extracted twice with ethyl acetate, and the extracts are washed in sequence twice with water and once with brine, then combined, dried over sodium sulfate, filtered and evaporated. Chromatography is then used to isolate the title product.

Modifications of the procedures presented below for Examples 719 and 759 may be used to prepare many of the compounds listed in Table IV.

EXAMPLE 719

Preparation of 5-[2-bromo-4-(1-methylethyl) phenyl]-N-butyl-N-ethyl-4,5-dihydro-7-methyltetrazolo[1,5-f]pteridin-9-amine A solution of the compound of Example 1 (358 mg, 0.78 mmol) in tetrahydrofuran (10 mL) was treated with trimethylsilylazide (0.21 mL, 1.58 mmol), diethyl azodicarboxylate (0.25 mL, 1.59 mmol) and triphenylphosphine (408 mg, 1.56 mmol). The resulting solution was stirred for 20 h, then evaporated. The residual material was separated by column chromatography (silica gel, 20:80 ethyl acetate-hexane) to afford the title product as a low-melting solid (147 mg, 0.30 mmol, 39%). Spectral data: TLC $R_F$ 0.37 (30:70 ethyl acetate-hexane). $^1$H NMR (300 MHz, CDCl$_3$): δ 7.52 (1H, d, J=1.8 Hz), 7.26 (1H, dd, J=8.0, 1.8 Hz), 7.21 (1H, d, J=8.0 Hz), 5.23 (1H, d, J=15.0 Hz), 4.98 (1H, d, J=15.0 Hz), 3.56–3.48 (4H, m), 2.94 (1H, heptet, J=7.0 Hz), 2.28 (3H, s), 1.69–1.59 (2H, m), 1.35–1.25 (2H, m), 1.29 (6H, d, J=7.0 Hz), 1.21 (3H, t, J=7.1 Hz), 0.90 (3H, t, J=7.3 Hz). MS (NH$_3$—CI): m/e 488 (17), 487 (64), 486 (18), 485 (63), 459 (100), 457 (97).

EXAMPLE 759

Preparation of 5-[2-bromo-4-(1-methylethyl) phenyl]-N-butyl-N-ethyl-5,6-dihydro-3-methylimidazo(1,2-f)pteridin-1-amine A solution of the compound of Example 248 and a slight excess of bromoacetaldehyde diethyl acetal in ethanol is heated to reflux until the starting material is consumed. The reaction mixture is evaporated, and the residual material is purified by chromatography or recrystallization to afford the title product.

TABLE I

| Ex No | X | $R^4$ | $R^5$ | $R^6$ | $R^7$ | $R^8$ | $R^{9a}$ | $R^{10}$ | mp, ° C. |
|---|---|---|---|---|---|---|---|---|---|
| 1 | C$_4$H$_9$(CH$_2$H$_5$)N | H | =O | H | H |  | A | CH$_3$ | 146–147 |
| 2 | (CH$_3$)$_2$N | H | =O | — | H | H | A | CH$_3$ | — |
| 3 | (CH$_2$H$_5$)$_2$N | H | =O | — | H | H | A | CH$_3$ | — |
| 4 | (C$_4$H$_9$)$_2$N | H | =O | — | H | H | A | CH$_3$ | — |
| 5 | CH$_3$OCH$_2$CH)C$_2$H$_5$)NH | H | =O | — | H | H | A | CH$_3$ | 197–198 |
| 6 | (CH$_3$O(CH$_2$)$_2$)$_2$N | H | =O | — | H | H | A | CH$_3$ | v. oil$^b$ |
| 7 | (CH$_3$)$_2$NCH$_2$CH(C$_3$H$_7$)NH | H | =O | — | H | H | A | CH$_3$ | 188–189 |
| 8 | C$_6$H$_5$CH$_2$(C$_2$H$_5$)NH | H | =O | — | H | H | A | CH$_3$ | — |
| 9 | (c-C$_3$H$_7$)CH$_2$(C$_2$H$_5$)NH | H | =O | — | H | H | A | CH$_3$ | — |
| 10 | (C$_3$H$_5$)$_2$CHNH | H | =O | — | H | H | A | CH$_3$ | — |
| 11 | C$_4$H$_9$ | H | =O | — | H | H | A | CH$_3$ | — |
| 12 | CH$_3$ | H | =O | — | H | H | A | CH$_3$ | — |
| 13 | (C$_2$H$_5$)$_2$CH | H | =O | — | H | H | A | CH$_3$ | — |
| 14 | C$_6$H$_5$ | H | =O | — | H | H | A | CH$_3$ | — |
| 15 | o-ClC$_6$H$_4$ | H | =O | — | H | H | A | CH$_3$ | — |
| 16 | o-NO$_2$—C$_6$H$_4$ | H | =O | — | H | H | A | CH$_3$ | — |
| 17 | o-CF$_3$—C$_6$H$_4$ | H | =O | — | H | H | A | CH$_3$ | 238–239 |
| 18 | 2-C$_5$H$_4$H | H | =O | — | H | H | A | CH$_3$ | — |
| 19 | (C$_2$H$_5$OC(=O))$_2$CH | H | =O | — | H | H | A | CH$_3$ | — |
| 20 | (CN)$_2$CH | H | =O | — | H | H | A | CH$_3$ | — |
| 21 | (CH$_3$OCH$_2$)$_2$CH | H | =O | — | H | H | A | CH$_3$ | — |
| 22 | CH$_3$S | H | =O | — | H | H | A | CH$_3$ | — |

TABLE I-continued

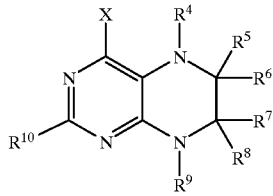

| Ex No | X | R⁴ | R⁵ | R⁶ | R⁷ | R⁸ | R⁹ᵃ | R¹⁰ | mp, ° C. |
|---|---|---|---|---|---|---|---|---|---|
| 23 | (C₃H₅)₂CHO | H | =O | — | H | H | A | CH₃ | — |
| 24 | C₄H₉(C₂H₅)N | H | H | H | H | H | A | CH₃ | 79–81 |
| 25 | (CH₃)₂N | H | H | H | H | H | A | CH₃ | — |
| 26 | (C₂H₅)₂N | H | H | H | H | H | A | CH₃ | — |
| 27 | (C₄H₉)₂N | H | H | H | H | H | A | CH₃ | — |
| 28 | CH₃OCH₂CH(C₂H₅)NH | H | H | H | H | H | A | CH₃ | 140–145 |
| 29 | (CH₃O(CH₂)₂)₂N | H | H | H | H | H | A | CH₃ | v. oilᵈ |
| 30 | (CH₃)₂NCH₂CH(C₃H₇)NH | H | H | H | H | H | A | CH₃ | 83–85 |
| 31 | C₆H₅CH₂(C₂H₅)NH | H | H | H | H | H | A | CH₃ | — |
| 32 | (c-C₃H₇)CH₂(C₂H₅)NH | H | H | H | H | H | A | CH₃ | — |
| 33 | (C₂H₅)₂CHNH | H | H | H | H | H | A | CH₃ | — |
| 34 | C₄H₉NH | H | H | H | H | H | A | CH₃ | 160–162 |
| 35 | CH₃ | H | H | H | H | H | A | CH₃ | — |
| 36 | (C₂H₅)₂CH | H | H | H | H | H | A | CH₃ | — |
| 37 | C₆H₅ | H | H | H | H | H | A | CH₃ | — |
| 38 | o-ClC₆H₄ | H | H | H | H | H | A | CH₃ | — |
| 39 | o-NO₂—C₆H₄ | H | H | H | H | H | A | CH₃ | — |
| 40 | o-CF₃—C₆H₄ | H | H | H | H | H | A | CH₃ | 108–110 |
| 41 | 2-C₅H₄H | H | H | H | H | H | A | CH₃ | — |
| 42 | (C₂H₅OC(=O))₂CH | H | H | H | H | H | A | CH₃ | — |
| 43 | (CN)₂CH | H | H | H | H | H | A | CH₃ | — |
| 44 | (CH₃OCH₂)₂CH | H | H | H | H | H | A | CH₃ | — |
| 45 | CH₃S | H | H | H | H | H | A | CH₃ | — |
| 46 | (CH₂H₅)₂CHO | H | H | H | H | H | A | CH₃ | — |
| 47 | C₄H₉(C₂H₅)N | H | =O | — | H | H | B | CH₃ | 171–173 |
| 48 | CH₃OCH₂CH(CH₂H₅)NH | H | =O | — | H | H | B | CH₃ | — |
| 49 | (CH₃O(CH₂)₂)₂N | H | =O | — | H | H | B | CH₃ | — |
| 50 | (CH₃)₂NCH₂CH(C₃H₇)NH | H | =O | — | H | H | B | CH₃ | — |
| 51 | o-CF₃—C₆H₄ | H | =O | — | H | H | B | CH₃ | — |
| 52 | (CH₂H₅)₂CHNH | H | =O | — | H | H | B | CH₃ | — |
| 53 | C₄H₉(C₂H₅)N | H | H | H | H | H | B | CH₃ | 99–100 |
| 54 | CH₃OCH₂CH(C₂H₅)NH | H | H | H | H | H | B | CH₃ | — |
| 55 | (CH₃O(CH₂)₂)₂N | H | H | H | H | H | B | CH₃ | — |
| 56 | (CH₃)₂NCH₂CH(C₃H₇)NH | H | H | H | H | H | B | CH₃ | — |
| 57 | o-CF₃—C₆H₄ | H | H | H | H | H | B | CH₃ | — |
| 58 | (CH₂H₅)₂CHNH | H | H | H | H | H | B | CH₃ | — |
| 59 | C₄H₉(C₂H₅)N | H | =O | — | H | H | C | CH₃ | 157–159 |
| 60 | CH₃OCH₂CH(C₂H₅)NH | H | =O | — | H | H | C | CH₃ | — |
| 61 | (CH₃O(CH₂)₂)₂N | H | =O | — | H | H | C | CH₃ | v. oilᵉ |
| 62 | (CH₃)₂NCH₂CH(C₃H₇)NH | H | =O | — | H | H | C | CH₃ | — |
| 63 | o-CF₃—C₆H₄ | H | =O | — | H | H | C | CH₃ | — |
| 64 | (C₂H₅)₂CHNH | H | =O | — | H | H | C | CH₃ | — |
| 65 | C₄H₉(C₂H₅)N | H | H | H | H | H | C | CH₃ | v. oilᶠ |
| 66 | CH₃OCH₂CH(C₂H₅)NH | H | H | H | H | H | C | CH₃ | — |
| 67 | (CH₃O(CH₂)₂)₂N | H | H | H | H | H | C | CH₃ | v. oilᵍ |
| 68 | (CH₃)₂NCH₂CH(C₃H₇)NH | H | H | H | H | H | C | CH₃ | — |
| 69 | o-CF₃—C₆H₄ | H | H | H | H | H | C | CH₃ | — |
| 70 | (C₂H₅)₂CHNH | H | H | H | H | H | C | CH₃ | — |
| 71 | C₄H₉(C₂H₅)N | H | =O | — | H | H | D | CH₃ | v. oilʰ |
| 72 | CH₃OCH₂CH(C₂H₅)NH | H | =O | — | H | H | D | CH₃ | 209–210 |
| 73 | (CH₃O(CH₂)₂)₂N | H | =O | — | H | H | D | CH₃ | — |
| 74 | (CH₃)₂NCH₂CH(C₃H₇)NH | H | =O | — | H | H | D | CH₃ | — |
| 75 | o-CF₃—C₆H₄ | H | =O | — | H | H | D | CH₃ | — |
| 76 | (C₂H₅)₂CHNH | H | =O | — | H | H | D | CH₃ | — |
| 77 | C₄H₉(C₂H₅)N | H | H | H | H | H | D | CH₃ | — |
| 78 | CH₃OCH₂CH(C₂H₅)NH | H | H | H | H | H | D | CH₃ | — |
| 79 | (CH₃O(CH₂)₂)₂N | H | H | H | H | H | D | CH₃ | — |
| 80 | (CH₃)₂NCH₂CH(C₃H₇)NH | H | H | H | H | H | D | CH₃ | — |
| 81 | o-CF₃—C₆H₄ | H | H | H | H | H | D | CH₃ | — |
| 82 | (C₂H₅)₂CHNH | H | H | H | H | H | D | CH₃ | — |
| 83 | C₄H₉(C₂H₅)N | H | =O | — | H | H | E | CH₃ | — |
| 84 | CH₃OCH₂CH(C₂H₅)NH | H | =O | — | H | H | E | CH₃ | 107–109 |
| 85 | (CH₃O(CH₂)₂)₂N | H | =O | — | H | H | E | CH₃ | — |
| 86 | (CH₃)₂NCH₂CH(C₃H₇)NH | H | =O | — | H | H | E | CH₃ | — |
| 87 | o-CF₃—C₆H₄ | H | =O | — | H | H | E | CH₃ | — |
| 88 | (C₂H₅)₂CHNH | H | =O | — | H | H | E | CH₃ | — |

TABLE I-continued

| Ex No | X | R⁴ | R⁵ | R⁶ | R⁷ | R⁸ | R⁹ᵃ | R¹⁰ | mp, °C. |
|---|---|---|---|---|---|---|---|---|---|
| 89 | $C_4H_9(C_2H_5)N$ | H | H | H | H | H | E | $CH_3$ | — |
| 90 | $CH_3OCH_2CH(C_2H_5)NH$ | H | H | H | H | H | E | $CH_3$ | — |
| 91 | $(CH_3O(CH_2)_2)_2N$ | H | H | H | H | H | E | $CH_3$ | — |
| 92 | $(CH_3)_2NCH_2CH(C_3H_7)NH$ | H | H | H | H | H | E | $CH_3$ | — |
| 93 | o-$CF_3$—$C_6H_4$ | H | H | H | H | H | E | $CH_3$ | — |
| 94 | $(C_2H_5)_2CHNH$ | H | H | H | H | H | E | $CH_3$ | — |
| 95 | $C_4H_9(C_2H_5)N$ | H | =O | — | H | H | F | $CH_3$ | — |
| 96 | $CH_3OCH_2CH(C_2H_5)NH$ | H | =O | — | H | H | F | $CH_3$ | 227–229 |
| 97 | $(CH_3O(CH_2)_2)_2N$ | H | =O | — | H | H | F | $CH_3$ | — |
| 98 | $(CH_3)_2NCH_2CH(C_3H_7)NH$ | H | =O | — | H | H | F | $CH_3$ | — |
| 99 | o-$CF_3$—$C_6H_4$ | H | =O | — | H | H | F | $CH_3$ | — |
| 100 | $(C_2H_5)_2CHNH$ | H | =O | — | H | H | F | $CH_3$ | — |
| 101 | $C_4H_9(C_2H_5)N$ | H | H | H | H | H | F | $CH_3$ | — |
| 102 | $CH_3OCH_2CH(C_2H_5)NH$ | H | H | H | H | H | F | $CH_3$ | 102–103 |
| 103 | $(CH_3O(CH_2)_2)_2N$ | H | H | H | H | H | F | $CH_3$ | — |
| 104 | $(CH_3)_2NCH_2CH(C_3H_7)NH$ | H | H | H | H | H | F | $CH_3$ | — |
| 105 | o-$CF_3$—$C_6H_4$ | H | H | H | H | H | F | $CH_3$ | — |
| 106 | $(C_2H_5)_2CHNH$ | H | H | H | H | H | F | $CH_3$ | — |
| 107 | $C_4H_9(C_2H_5)N$ | H | =O | — | H | H | G | $CH_3$ | — |
| 108 | $CH_3OCH_2CH(C_2H_5)NH$ | H | =O | — | H | H | G | $CH_3$ | — |
| 109 | $(CH_3O(CH_2)_2)_2N$ | H | =O | — | H | H | G | $CH_3$ | — |
| 110 | $(CH_3)_2NCH_2CH(C_3H_7)NH$ | H | =O | — | H | H | G | $CH_3$ | — |
| 111 | o-$CF_3$—$C_6H_4$ | H | =O | — | H | H | G | $CH_3$ | — |
| 112 | $(C_2H_5)_2CHNH$ | H | =O | — | H | H | G | $CH_3$ | — |
| 113 | $C_4H_9(C_2H_5)N$ | H | H | H | H | H | G | $CH_3$ | — |
| 114 | $CH_3OCH_2CH(C_2H_5)NH$ | H | H | H | H | H | G | $CH_3$ | — |
| 115 | $(CH_3O(CH_2)_2)_2N$ | H | H | H | H | H | G | $CH_3$ | — |
| 116 | $(CH_3)_2NCH_2CH(C_3H_7)NH$ | H | H | H | H | H | G | $CH_3$ | — |
| 117 | o-$CF_3$—$C_6H_4$ | H | H | H | H | H | G | $CH_3$ | — |
| 118 | $(C_2H_5)_2CHNH$ | H | H | H | H | H | G | $CH_3$ | — |
| 119 | $C_4H_9(C_2H_5)N$ | H | =O | — | H | H | J | $CH_3$ | — |
| 120 | $CH_3OCH_2CH(C_2H_5)NH$ | H | =O | — | H | H | J | $CH_3$ | — |
| 121 | $(CH_3O(CH_2)_2)_2N$ | H | =O | — | H | H | J | $CH_3$ | — |
| 122 | $(CH_3)_2NCH_2CH(C_3H_7)NH$ | H | =O | — | H | H | J | $CH_3$ | — |
| 123 | o-$CF_3$—$C_6H_4$ | H | =O | — | H | H | J | $CH_3$ | — |
| 124 | $(C_2H_5)_2CHNH$ | H | =O | — | H | H | J | $CH_3$ | — |
| 125 | $C_4H_9(C_2H_5)N$ | H | H | H | H | H | J | $CH_3$ | — |
| 126 | $CH_3OCH_2CH(C_2H_5)NH$ | H | H | H | H | H | J | $CH_3$ | — |
| 127 | $(CH_3O(CH_2)_2)_2N$ | H | H | H | H | H | J | $CH_3$ | — |
| 128 | $(CH_3)_2NCH_2CH(C_3H_7)NH$ | H | H | H | H | H | J | $CH_3$ | — |
| 129 | o-$CF_3$—$C_6H_4$ | H | H | H | H | H | J | $CH_3$ | — |
| 130 | $(C_2H_5)_2CHNH$ | H | H | H | H | H | J | $CH_3$ | — |
| 131 | $C_4H_9(C_2H_5)N$ | H | =S | — | H | H | A | $CH_3$ | 148–149 |
| 132 | $CH_3OCH_2CH(C_2H_5)NH$ | H | =S | — | H | H | A | $CH_3$ | — |
| 133 | $(CH_3O(CH_2)_2)_2N$ | H | =S | — | H | H | A | $CH_3$ | — |
| 134 | $(CH_3)_2NCH_2CH(C_3H_7)NH$ | H | =S | — | H | H | A | $CH_3$ | — |
| 135 | o-$CF_3$—$C_6H_4$ | H | =S | — | H | H | A | $CH_3$ | — |
| 136 | $(C_2H_5)_2CHNH$ | H | =S | — | H | H | A | $CH_3$ | — |
| 137 | $C_4H_9(C_2H_5)N$ | $CH_3$ | =S | — | H | H | A | $CH_3$ | v. oil[i] |
| 138 | $CH_3OCH_2CH(C_2H_5)NH$ | $CH_3$ | =S | — | H | H | A | $CH_3$ | — |
| 139 | $(CH_3O(CH_2)_2)_2N$ | $CH_3$ | =S | — | H | H | A | $CH_3$ | — |
| 140 | $(CH_3)_2NCH_2CH(C_3H_7)NH$ | $CH_3$ | =S | — | H | H | A | $CH_3$ | — |
| 141 | o-$CF_3$—$C_6H_4$ | $CH_3$ | =S | — | H | H | A | $CH_3$ | — |
| 142 | $(C_2H_5)_2CHNH$ | $CH_3$ | =S | — | H | H | A | $CH_3$ | — |
| 143 | $C_4H_9(C_2H_5)N$ | $CH_3$ | =O | — | H | H | A | $CH_3$ | v. oil[j] |
| 144 | $CH_3OCH_2CH(C_2H_5)NH$ | $CH_3$ | =O | — | H | H | A | $CH_3$ | — |
| 145 | $(CH_3O(CH_2)_2)_2N$ | $CH_3$ | =O | — | H | H | A | $CH_3$ | — |
| 146 | $(CH_3)_2NCH_2CH(C_3H_7)NH$ | $CH_3$ | =O | — | H | H | A | $CH_3$ | — |
| 147 | o-$CF_3$—$C_6H_4$ | $CH_3$ | =O | — | H | H | A | $CH_3$ | v. oil[k] |
| 148 | $(C_2H_5)_2CHNH$ | $CH_3$ | =O | — | H | H | A | $CH_3$ | — |
| 149 | $C_4H_9(C_2H_5)N$ | $CH_3$ | H | H | H | H | A | $CH_3$ | v. oil[l] |
| 150 | $CH_3OCH_2CH(C_2H_5)NH$ | $CH_3$ | H | H | H | H | A | $CH_3$ | — |
| 151 | $(CH_3O(CH_2)_2)_2N$ | $CH_3$ | H | H | H | H | A | $CH_3$ | — |
| 152 | $(CH_3)_2NCH_2CH(C_3H_7)NH$ | $CH_3$ | H | H | H | H | A | $CH_3$ | — |
| 153 | o-$CF_3$—$C_6H_4$ | $CH_3$ | H | H | H | H | A | $CH_3$ | 108–110 |
| 154 | $(C_2H_5)_2CHNH$ | $CH_3$ | H | H | H | H | A | $CH_3$ | — |

TABLE I-continued

| Ex No | X | R4 | R5 | R6 | R7 | R8 | R9a | R10 | mp, °C. |
|---|---|---|---|---|---|---|---|---|---|
| 155 | $C_4H_9(C_2H_5)N$ | $CH_3$ | =O | — | H | H | A | $CH_3$ | v. oil$^m$ |
| 156 | $CH_3OCH_2CH(C_2H_5)NH$ | $CH_3$ | =O | — | H | H | A | $CH_3$ | — |
| 157 | $(CH_3O(CH_2)_2)_2N$ | $CH_3$ | =O | — | H | H | A | $CH_3$ | — |
| 158 | $(CH_3)_2NCH_2CH(C_3H_7)NH$ | $CH_3$ | =O | — | H | H | A | $CH_3$ | — |
| 159 | o-$CF_3$—$C_6H_4$ | $CH_3$ | =O | — | H | H | A | $CH_3$ | v. oil$^n$ |
| 160 | $(C_2H_5)_2CHNH$ | $CH_3$ | =O | — | H | H | A | $CH_3$ | — |
| 161 | $C_4H_9(C_2H_5)N$ | $CH_3$ | H | H | H | H | A | $CH_3$ | — |
| 162 | $CH_3OCH_2CH(C_2H_5)NH$ | $CH_3$ | H | H | H | H | A | $CH_3$ | — |
| 163 | $(CH_3O(CH_2)_2)_2N$ | $CH_3$ | H | H | H | H | A | $CH_3$ | — |
| 164 | $(CH_3)_2NCH_2CH(C_3H_7)NH$ | $CH_3$ | H | H | H | H | A | $CH_3$ | — |
| 165 | o-$CF_3$—$C_6H_4$ | $CH_3$ | H | H | H | H | A | $CH_3$ | — |
| 166 | $(C_2H_5)_2CHNH$ | $CH_3$ | H | H | H | H | A | $CH_3$ | — |
| 167 | $C_4H_9(C_2H_5)N$ | $CH_2CH=CH_2$ | =O | — | H | H | A | $CH_3$ | — |
| 168 | $CH_3OCH_2CH(C_2H_5)NH$ | $CH_2CH=CH_2$ | =O | — | H | H | A | $CH_3$ | — |
| 169 | $(CH_3O(CH_2)_2)_2N$ | $CH_2CH=CH_2$ | =O | — | H | H | A | $CH_3$ | — |
| 170 | $(CH_3)_2NCH_2CH(C_3H_7)NH$ | $CH_2CH=CH_2$ | =O | — | H | H | A | $CH_3$ | — |
| 171 | o-$CF_3$—$C_6H_4$ | $CH_2CH=CH_2$ | =O | — | H | H | A | $CH_3$ | 167–168 |
| 172 | $(C_2H_5)_2CHNH$ | $CH_2CH=CH_2$ | =O | — | H | H | A | $CH_3$ | — |
| 173 | $C_4H_9(C_2H_5)N$ | $CH_2CH=CH_2$ | H | H | H | H | A | $CH_3$ | — |
| 174 | $CH_3OCH_2CH(C_2H_5)NH$ | $CH_2CH=CH_2$ | H | H | H | H | A | $CH_3$ | — |
| 175 | $(CH_3O(CH_2)_2)_2N$ | $CH_2CH=CH_2$ | H | H | H | H | A | $CH_3$ | — |
| 176 | $(CH_3)_2NCH_2CH(C_3H_7)NH$ | $CH_2CH=CH_2$ | H | H | H | H | A | $CH_3$ | — |
| 177 | o-$CF_3$—$C_6H_4$ | $CH_2CH=CH_2$ | H | H | H | H | A | $CH_3$ | — |
| 178 | $(C_2H_5)_2CHNH$ | $CH_2CH=CH_2$ | H | H | H | H | A | $CH_3$ | — |
| 179 | $C_4H_9(C_2H_5)N$ | $CH_2CH=CH_2$ | =O | — | $CH_2CH=CH_2$ | H | A | $CH_3$ | — |
| 180 | $CH_3OCH_2CH(C_2H_5)NH$ | $CH_2CH=CH_2$ | =O | — | $CH_2CH=CH_2$ | H | A | $CH_3$ | — |
| 181 | $(CH_3O(CH_2)_2)_2N$ | $CH_2CH=CH_2$ | =O | — | $CH_2CH=CH_2$ | H | A | $CH_3$ | — |
| 182 | $(CH_3)_2NCH_2CH(C_3H_7)NH$ | $CH_2CH=CH_2$ | =O | — | $CH_2CH=CH_2$ | H | A | $CH_3$ | — |
| 183 | o-$CF_3$—$C_6H_4$ | $CH_3$ | =O | — | $CH_2CH=CH_2$ | H | A | $CH_3$ | — |
| 184 | $(C_2H_5)_2CHNH$ | $CH_2CH=CH_2$ | =O | — | $CH_2CH=CH_2$ | H | A | $CH_3$ | — |
| 185 | $C_4H_9(C_2H_5)N$ | $CH_2CH=CH_2$ | H | H | $CH_2CH=CH_2$ | H | A | $CH_3$ | — |
| 186 | $CH_3OCH_2CH(C_2H_5)NH$ | $CH_2CH=CH_2$ | H | H | $CH_2CH=CH_2$ | H | A | $CH_3$ | — |
| 187 | $(CH_3O(CH_2)_2)_2N$ | $CH_2CH=CH_2$ | H | H | $CH_2CH=CH_2$ | H | A | $CH_3$ | — |
| 188 | $(CH_3)_2NCH_2CH(C_3H_7)NH$ | $CH_2CH=CH_2$ | H | H | $CH_2CH=CH_2$ | H | A | $CH_3$ | — |
| 189 | o-$CF_3$—$C_6H_4$ | $CH_2CH=CH_2$ | H | H | $CH_2CH=CH_2$ | H | A | $CH_3$ | — |
| 190 | $(C_2H_5)_2CHNH$ | $CH_2CH=CH_2$ | H | H | $CH_2CH=CH_2$ | H | A | $CH_3$ | — |
| 191 | $C_4H_9(C_2H_5)N$ | H | $CH_3$ | $CH_3$ | H | H | A | $CH_3$ | — |
| 192 | $CH_3OCH_2CH(C_2H_5)NH$ | H | $CH_3$ | $CH_3$ | H | H | A | $CH_3$ | — |
| 193 | $(CH_3O(CH_2)_2)_2N$ | H | $CH_3$ | $CH_3$ | H | H | A | $CH_3$ | — |
| 194 | $(CH_3)_2NCH_2CH(C_3H_7)NH$ | H | $CH_3$ | $CH_3$ | H | H | A | $CH_3$ | — |
| 195 | o-$CF_3$—$C_6H_4$ | H | $CH_3$ | $CH_3$ | H | H | A | $CH_3$ | — |
| 196 | $(C_2H_5)_2CHNH$ | H | $CH_3$ | $CH_3$ | H | H | A | $CH_3$ | — |
| 197 | $C_4H_9(C_2H_5)N$ | H | =O | — | $CH_3$ | $CH_3$ | A | $CH_3$ | — |
| 198 | $CH_3OCH_2CH(C_2H_5)NH$ | H | =O | — | $CH_3$ | $CH_3$ | A | $CH_3$ | — |
| 199 | $(CH_3O(CH_2)_2)_2N$ | H | =O | — | $CH_3$ | $CH_3$ | A | $CH_3$ | — |
| 200 | $(CH_3)_2NCH_2CH(C_3H_7)NH$ | H | =O | — | $CH_3$ | $CH_3$ | A | $CH_3$ | — |
| 201 | o-$CF_3$—$C_6H_4$ | H | =O | — | $CH_3$ | $CH_3$ | A | $CH_3$ | — |
| 202 | $(C_2H_5)_2CHNH$ | H | =O | — | $CH_3$ | $CH_3$ | A | $CH_3$ | — |
| 203 | $C_4H_9(C_2H_5)N$ | H | H | H | $CH_3$ | $CH_3$ | A | $CH_3$ | — |
| 204 | $CH_3OCH_2CH(C_2H_5)NH$ | H | H | H | $CH_3$ | $CH_3$ | A | $CH_3$ | — |
| 205 | $(CH_3O(CH_2)_2)_2N$ | H | H | H | $CH_3$ | $CH_3$ | A | $CH_3$ | — |
| 206 | $(CH_3)_2NCH_2CH(C_3H_7)NH$ | H | H | H | $CH_3$ | $CH_3$ | A | $CH_3$ | — |
| 207 | o-$CF_3$—$C_6H_4$ | H | H | H | $CH_3$ | $CH_3$ | A | $CH_3$ | — |
| 208 | $(C_2H_5)_2CHNH$ | H | H | H | $CH_3$ | $CH_3$ | A | $CH_3$ | — |
| 209 | $C_4H_9(C_2H_5)N$ | H | =O | — | H | H | A | H | — |
| 210 | $CH_3OCH_2CH(C_2H_5)NH$ | H | =O | — | H | H | A | H | — |
| 211 | $(CH_3O(CH_2)_2)_2N$ | H | =O | — | H | H | A | H | — |
| 212 | $(CH_3)_2NCH_2CH(C_3H_7)NH$ | H | =O | — | H | H | A | H | — |
| 213 | o-$CF_3$—$C_6H_4$ | H | =O | — | H | H | A | H | — |
| 214 | $(C_2H_5)_2CHNH$ | H | =O | — | H | H | A | H | — |
| 215 | $C_4H_9(C_2H_5)N$ | H | H | H | H | H | A | H | — |
| 216 | $CH_3OCH_2CH(C_2H_5)NH$ | H | H | H | H | H | A | H | — |
| 217 | $(CH_3O(CH_2)_2)_2N$ | H | H | H | H | H | A | H | — |
| 218 | $(CH_3)_2NCH_2CH(C_3H_7)NH$ | H | H | H | H | H | A | H | — |
| 219 | o-$CF_3$—$C_6H_4$ | H | H | H | H | H | A | H | — |
| 220 | $(C_2H_5)_2CHNH$ | H | H | H | H | H | A | H | — |

TABLE I-continued

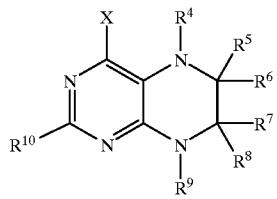

| Ex No | X | R4 | R5 | R6 | R7 | R8 | R9a | R10 | mp, °C. |
|---|---|---|---|---|---|---|---|---|---|
| 221 | $C_4H_9(C_2H_5)N$ | H | =O | — | H | H | A | CN | — |
| 222 | $CH_3OCH_2CH(C_2H_5)NH$ | H | =O | — | H | H | A | CN | — |
| 223 | $(CH_3O(CH_2)_2)_2N$ | H | =O | — | H | H | A | CN | — |
| 224 | $(CH_3)_2NCH_2CH(C_3H_7)NH$ | H | =O | — | H | H | A | CN | — |
| 225 | o-$CF_3$—$C_6H_4$ | H | =O | — | H | H | A | CN | — |
| 226 | $(C_2H_5)_2CHNH$ | H | =O | — | H | H | A | CN | — |
| 227 | $C_4H_9(C_2H_5)N$ | H | H | H | H | H | A | CN | — |
| 228 | $CH_3OCH_2CH(C_2H_5)NH$ | H | H | H | H | H | A | CN | — |
| 229 | $(CH_3O(CH_2)_2)_2N$ | H | H | H | H | H | A | CN | — |
| 230 | $(CH_3)_2NCH_2CH(C_3H_7)NH$ | H | H | H | H | H | A | CN | — |
| 231 | o-$CF_3$—$C_6H_4$ | H | H | H | H | H | A | CN | — |
| 232 | $(C_2H_5)_2CHNH$ | H | H | H | H | H | A | CN | — |
| 233 | 2-morpholinyl | H | H | H | H | H | A | $CH_3$ | 60–62 |
| 234 | 2-morpholinyl | H | =O | — | H | H | B | $CH_3$ | — |
| 235 | 2-morpholinyl | H | =O | — | H | H | C | $CH_3$ | — |
| 236 | 2-morpholinyl | H | =O | — | H | H | D | $CH_3$ | — |
| 237 | 2-morpholinyl | H | =O | — | H | H | E | $CH_3$ | — |
| 238 | 2-morpholinyl | H | =O | — | H | H | F | $CH_3$ | — |
| 239 | 2-morpholinyl | H | =O | — | H | H | G | $CH_3$ | — |
| 240 | 2-morpholinyl | H | =O | — | H | H | J | $CH_3$ | — |
| 241 | 2-morpholinyl | H | H | H | H | H | B | $CH_3$ | — |
| 242 | 2-morpholinyl | H | H | H | H | H | C | $CH_3$ | — |
| 243 | 2-morpholinyl | H | H | H | H | H | D | $CH_3$ | — |
| 244 | 2-morpholinyl | H | H | H | H | H | E | $CH_3$ | — |
| 245 | 2-morpholinyl | H | H | H | H | H | F | $CH_3$ | — |
| 246 | 2-morpholinyl | H | H | H | H | H | G | $CH_3$ | — |
| 247 | 2-morpholinyl | H | H | H | H | H | J | $CH_3$ | — |
| 248 | $C_4H_9(C_2H_5)N$ | H | =NH | — | H | H | A | $CH_3$ | — |
| 249 | $C_4H_9(C_2H_5)N$ | H | =NH | — | H | H | C | $CH_3$ | — |
| 250 | $C_4H_9(C_2H_5)N$ | H | =$NC_4H_9$ | — | H | H | A | $CH_3$ | — |

TABLE II

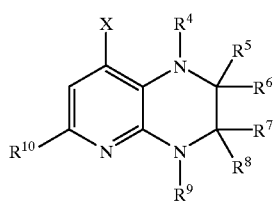

| Ex No | X | R4 | R5 | R6 | R7 | R8 | R9a | R10 | mp, °C. |
|---|---|---|---|---|---|---|---|---|---|
| 251 | $C_4H_9(C_2H_5)N$ | H | =O | — | H | H | A | $CH_3$ | — |
| 252 | $(CH_3)_2N$ | H | =O | — | H | H | A | $CH_3$ | — |
| 253 | $(C_2H_5)_2N$ | H | =O | — | H | H | A | $CH_3$ | — |
| 254 | $(C_4H_9)_2N$ | H | =O | — | H | H | A | $CH_3$ | — |
| 255 | $CH_3OCH_2CH(C_2H_5)NH$ | H | =O | — | H | H | A | $CH_3$ | — |
| 256 | $(CH_3O)CH_2)_2)_2N$ | H | =O | — | H | H | A | $CH_3$ | — |
| 257 | $(CH_3)_2NCH_2CH)C_3H_7)NH$ | H | =O | — | H | H | A | $CH_3$ | — |
| 258 | $C_6H_5CH_2)C_2H_5)NH$ | H | =O | — | H | H | A | $CH_3$ | — |
| 259 | (c-$C_3H_7)CH_2(C_2H_5)NH$ | H | =O | — | H | H | A | $CH_3$ | — |
| 260 | $(C_2H_5)_2CHNH$ | H | =O | — | H | H | A | $CH_3$ | — |
| 261 | $C_4H_9$ | H | =O | — | H | H | A | $CH_3$ | — |
| 262 | $CH_3$ | H | =O | — | H | H | A | $CH_3$ | — |
| 263 | $(C_2H_5)_2CH$ | H | =O | — | H | H | A | $CH_3$ | — |
| 264 | $C_6H_5$ | H | =O | — | H | H | A | $CH_3$ | — |
| 265 | o-$ClC_6H_4$ | H | =O | — | H | H | A | $CH_3$ | — |
| 266 | o-$NO_2$—$C_6H_4$ | H | =O | — | H | H | A | $CH_3$ | — |
| 267 | o-$CF_3$—$C_6H_4$ | H | =O | — | H | H | A | $CH_3$ | — |
| 268 | 2-$C_5H_4N$ | H | =O | — | H | H | A | $CH_3$ | — |

TABLE II-continued

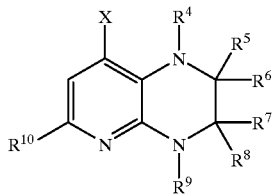

| Ex No | X | $R^4$ | $R^5$ | $R^6$ | $R^7$ | $R^8$ | $R^{9\,a}$ | $R^{10}$ | mp, °C. |
|---|---|---|---|---|---|---|---|---|---|
| 269 | $(C_2H_5OC(=O))_2CH$ | H | =O | — | H | H | A | $CH_3$ | — |
| 270 | $(CN)_2CH$ | H | =O | — | H | H | A | $CH_3$ | — |
| 271 | $(CH_2OCH_2)_2CH$ | H | =O | — | H | H | A | $CH_3$ | — |
| 272 | $CH_3S$ | H | =O | — | H | H | A | $CH_3$ | — |
| 273 | $(C_2H_5)_2CHO$ | H | =O | — | H | H | A | $CH_3$ | — |
| 274 | $C_4H_9(C_2H_5)N$ | H | H | H | H | H | A | $CH_3$ | — |
| 275 | $(CH_3)_2N$ | H | H | H | H | H | A | $CH_3$ | — |
| 276 | $(C_2H_5)_2N$ | H | H | H | H | H | A | $CH_3$ | — |
| 277 | $(C_4H_9)_2N$ | H | H | H | H | H | A | $CH_3$ | — |
| 278 | $CH_3OCH_2CH(C_2H_5)NH$ | H | H | H | H | H | A | $CH_3$ | — |
| 279 | $(CH_3O(CH_2)_2)_2N$ | H | H | H | H | H | A | $CH_3$ | — |
| 280 | $(CH_3)_2NCH_2CH(C_3H_7)NH$ | H | H | H | H | H | A | $CH_3$ | — |
| 281 | $C_6H_5CH_2(C_2H_5)NH$ | H | H | H | H | H | A | $CH_3$ | — |
| 282 | $(c\text{-}C_3H_7)CH_2(C_2H_5)NH$ | H | H | H | H | H | A | $CH_3$ | — |
| 283 | $(C_2H_5)_2CHNH$ | H | H | H | H | H | A | $CH_3$ | — |
| 284 | $C_4H_9NH$ | H | H | H | H | H | A | $CH_3$ | — |
| 285 | $CH_3$ | H | H | H | H | H | A | $CH_3$ | — |
| 286 | $(C_2H_5)_2CH$ | H | H | H | H | H | A | $CH_3$ | — |
| 287 | $C_6H_5$ | H | H | H | H | H | A | $CH_3$ | — |
| 288 | $o\text{-}ClC_6H_4$ | H | H | H | H | H | A | $CH_3$ | — |
| 289 | $o\text{-}NO_2\text{—}C_6H_4$ | H | H | H | H | H | A | $CH_3$ | — |
| 290 | $o\text{-}CF_3\text{—}C_6H_4$ | H | H | H | H | H | A | $CH_3$ | — |
| 291 | $2\text{-}C_5H_4N$ | H | H | H | H | H | A | $CH_3$ | — |
| 292 | $(C_2H_5OC(=O))_2CH$ | H | H | H | H | H | A | $CH_3$ | — |
| 293 | $(CN)_2CH$ | H | H | H | H | H | A | $CH_3$ | — |
| 294 | $(CH_3OCH_2)_2CH$ | H | H | H | H | H | A | $CH_3$ | — |
| 295 | $CH_3S$ | H | H | H | H | H | A | $CH_3$ | — |
| 296 | $(C_2H_5)_2CHO$ | H | H | H | H | H | A | $CH_3$ | — |
| 297 | $C_4H_9(C_2H_5)N$ | H | =O | — | H | H | B | $CH_3$ | — |
| 298 | $CH_3OCH_2CH(C_2H_5)NH$ | H | =O | — | H | H | B | $CH_3$ | — |
| 299 | $(CH_3O(CH_2)_2)_2N$ | H | =O | — | H | H | B | $CH_3$ | — |
| 300 | $(CH_3)_2NCH_2CH(C_3H_7)NH$ | H | =O | — | H | H | B | $CH_3$ | — |
| 301 | $o\text{-}CF_3\text{—}C_6H_4$ | H | =O | — | H | H | B | $CH_3$ | — |
| 302 | $(C_2H_5)_2CHNH$ | H | =O | — | H | H | B | $CH_3$ | — |
| 303 | $C_4H_9(C_2H_5)N$ | H | H | H | H | H | B | $CH_3$ | — |
| 304 | $CH_3OCH_2CH(C_2H_5)NH$ | H | H | H | H | H | B | $CH_3$ | — |
| 305 | $(CH_3O(CH_2)_2)_2N$ | H | H | H | H | H | B | $CH_3$ | — |
| 306 | $(CH_2)_2NCH_2CH(C_3H_7)NH$ | H | H | H | H | H | B | $CH_3$ | — |
| 307 | $o\text{-}CF_3\text{—}C_6H_4$ | H | H | H | H | H | B | $CH_3$ | — |
| 308 | $(C_2H_5)_2CHNH$ | H | H | H | H | H | B | $CH_3$ | — |
| 309 | $C_4H_9(C_2H_5)N$ | H | =O | — | H | H | C | $CH_3$ | — |
| 310 | $CH_3OCH_2CH(C_2H_5)NH$ | H | =O | — | H | H | C | $CH_3$ | — |
| 311 | $(CH_3O(CH_2)_2)_2N$ | H | =O | — | H | H | C | $CH_3$ | — |
| 312 | $(CH_3)_2NCH_2CH(C_3H_7)NH$ | H | =O | — | H | H | C | $CH_3$ | — |
| 313 | $o\text{-}CF_3\text{—}C_6H_4$ | H | =O | — | H | H | C | $CH_3$ | — |
| 314 | $(C_2H_5)_2CHNH$ | H | =O | — | H | H | C | $CH_3$ | — |
| 315 | $C_4H_9(C_2H_5)N$ | H | H | H | H | H | C | $CH_3$ | — |
| 316 | $CH_3OCH_2CH(C_2H_5)NH$ | H | H | H | H | H | C | $CH_3$ | — |
| 317 | $(CH_3O(CH_2)_2)_2N$ | H | H | H | H | H | C | $CH_3$ | — |
| 318 | $(CH_3)_2NCH_2CH(C_3H_7)NH$ | H | H | H | H | H | C | $CH_3$ | — |
| 319 | $o\text{-}CF_3\text{—}C_6H_4$ | H | H | H | H | H | C | $CH_3$ | — |
| 320 | $(C_2H_5)_2CHNH$ | H | H | H | H | H | C | $CH_3$ | — |
| 321 | $C_4H_9(C_2H_5)N$ | H | =O | — | H | H | D | $CH_3$ | — |
| 322 | $CH_3OCH_2CH(C_2H_5)NH$ | H | =O | — | H | H | D | $CH_3$ | — |
| 323 | $(CH_3O(CH_2)_2)_2N$ | H | =O | — | H | H | D | $CH_3$ | — |
| 324 | $(CH_3)_2NCH_2CH(C_3H_7)NH$ | H | =O | — | H | H | D | $CH_3$ | — |
| 325 | $o\text{-}CF_3\text{—}C_6H_4$ | H | =O | — | H | H | D | $CH_3$ | — |
| 326 | $(C_2H_5)_2CHNH$ | H | =O | — | H | H | D | $CH_3$ | — |
| 327 | $C_4H_9(C_2H_5)N$ | H | H | H | H | H | D | $CH_3$ | — |
| 328 | $CH_3OCH_2CH(C_2H_5)NH$ | H | H | H | H | H | D | $CH_3$ | — |
| 329 | $(CH_3O(CH_2)_2)_2N$ | H | H | H | H | H | D | $CH_3$ | — |
| 330 | $(CH_3)_2NCH_2CH(C_3H_7)NH$ | H | H | H | H | H | D | $CH_3$ | — |
| 331 | $o\text{-}CF_3\text{—}C_6H_4$ | H | H | H | H | H | D | $CH_3$ | — |
| 332 | $(C_2H_5)_2CHNH$ | H | H | H | H | H | D | $CH_3$ | — |
| 333 | $C_4H_9(C_2H_5)N$ | H | =O | — | H | H | E | $CH_3$ | — |
| 334 | $CH_3OCH_2CH(C_2H_5)NH$ | H | =O | — | H | H | E | $CH_3$ | — |

TABLE II-continued

| Ex No | X | R⁴ | R⁵ | R⁶ | R⁷ | R⁸ | R⁹ ᵃ | R¹⁰ | mp, °C. |
|---|---|---|---|---|---|---|---|---|---|
| 335 | (CH₃O(CH₂)₂)₂N | H | =O | — | H | H | E | CH₃ | — |
| 336 | (CH₃)₂NCH₂CH(C₃H₇)NH | H | =O | — | H | H | E | CH₃ | — |
| 337 | o-CF₃—C₆H₄ | H | =O | — | H | H | E | CH₃ | — |
| 338 | (C₂H₅)₂CHNH | H | =O | — | H | H | E | CH₃ | — |
| 339 | C₄H₉(C₂H₅)N | H | H | H | H | H | E | CH₃ | — |
| 340 | CH₃OCH₂CH(C₂H₅)NH | H | H | H | H | H | E | CH₃ | — |
| 341 | (CH₃O(CH₂)₂)₂N | H | H | H | H | H | E | CH₃ | — |
| 342 | (CH₃)₂NCH₂CH(C₃H₇)NH | H | H | H | H | H | E | CH₃ | — |
| 343 | o-CF₃—C₆H₄ | H | H | H | H | H | E | CH₃ | — |
| 344 | (C₂H₅)₂CHNH | H | H | H | H | H | E | CH₃ | — |
| 345 | C₄H₉(C₂H₅)N | H | =O | — | H | H | F | CH₃ | — |
| 346 | CH₃OCH₂CH(C₂H₅)NH | H | =O | — | H | H | F | CH₃ | — |
| 347 | (CH₃O)(CH₂)₂)₂N | H | =O | — | H | H | F | CH₃ | — |
| 348 | (CH₃)₂NCH₂CH(C₃H₇)NH | H | =O | — | H | H | F | CH₃ | — |
| 349 | o-CF₃—C₆H₄ | H | =O | — | H | H | F | CH₃ | — |
| 350 | (C₂H₅)₂CHNH | H | =O | — | H | H | F | CH₃ | — |
| 351 | C₄H₉(C₂H₅)N | H | =O | — | H | H | F | CH₃ | — |
| 352 | CH₃OCH₂CH(C₂H₅)NH | H | =O | — | H | H | F | CH₃ | — |
| 353 | (CH₃O(CH₂)₂)₂N | H | =O | — | H | H | F | CH₃ | — |
| 354 | (CH₃)₂NCH₂CH(C₃H₇)NH | H | =O | — | H | H | F | CH₃ | — |
| 355 | o-CF₃—C₆H₄ | H | =O | — | H | H | F | CH₃ | — |
| 356 | (C₂H₅)₂CHNH | H | H | H | H | H | F | CH₃ | — |
| 357 | C₄H₉(C₂H₅)N | H | =O | — | H | H | G | CH₃ | — |
| 358 | CH₃OCH₂CH(C₂H₅)NH | H | =O | — | H | H | G | CH₃ | — |
| 359 | (CH₃O(CH₂)₂)₂N | H | =O | — | H | H | G | CH₃ | — |
| 360 | (CH₃)₂NCH₂CH(C₃H₇)NH | H | =O | — | H | H | G | CH₃ | — |
| 361 | o-CF₃—C₆H₄ | H | =O | — | H | H | G | CH₃ | — |
| 362 | (C₂H₅)₂CHNH | H | =O | — | H | H | G | CH₃ | — |
| 363 | C₄H₉(C₂H₅)N | H | H | H | H | H | G | CH₃ | — |
| 364 | CH₃OCH₂CH(C₂H₅)NH | H | H | H | H | H | G | CH₃ | — |
| 365 | (CH₃O(CH₂)₂)₂N | H | H | H | H | H | G | CH₃ | — |
| 366 | (CH₃)₂NCH₂CH(C₃H₇)NH | H | H | H | H | H | G | CH₃ | — |
| 367 | o-CF₃—C₆H₄ | H | H | H | H | H | G | CH₃ | — |
| 368 | (C₂H₅)₂CHNH | H | H | H | H | H | G | CH₃ | — |
| 369 | C₄H₉(C₂H₅)N | H | =O | — | H | H | J | CH₃ | — |
| 370 | CH₃OCH₂CH(C₂H₅)NH | H | =O | — | H | H | J | CH₃ | — |
| 371 | (CH₃O(CH₂)₂)₂N | H | =O | — | H | H | J | CH₃ | — |
| 372 | (CH₃)₂NCH₂CH(C₃H₇)NH | H | =O | — | H | H | J | CH₃ | — |
| 373 | o-CF₃—C₆H₄ | H | =O | — | H | H | J | CH₃ | — |
| 374 | (C₂H₅)₂CHNH | H | =O | — | H | H | J | CH₃ | — |
| 375 | C₄H₉(C₂H₅)N | H | H | H | H | H | J | CH₃ | — |
| 376 | CH₃OCH₂CH(C₂H₅)NH | H | H | H | H | H | J | CH₃ | — |
| 377 | (CH₃O(CH₂)₂)₂N | H | H | H | H | H | J | CH₃ | — |
| 378 | (CH₃)₂NCH₂CH(C₃H₇)NH | H | H | H | H | H | J | CH₃ | — |
| 379 | o-CF₃—C₆H₄ | H | H | H | H | H | J | CH₃ | — |
| 380 | (C₂H₅)₂CHNH | H | H | H | H | H | J | CH₃ | — |
| 381 | C₄H₉(C₂H₅)N | H | =S | — | H | H | A | CH₃ | — |
| 382 | CH₃OCH₂CH(C₂H₅)NH | H | =S | — | H | H | A | CH₃ | — |
| 383 | (CH₃O(CH₂)₂)₂N | H | =S | — | H | H | A | CH₃ | — |
| 384 | (CH₃)₂NCH₂CH(C₃H₇)NH | H | =S | — | H | H | A | CH₃ | — |
| 385 | o-CF₃—C₆H₄ | H | =S | — | H | H | A | CH₃ | — |
| 386 | (C₂H₅)₂CHNH | H | =S | — | H | H | A | CH₃ | — |
| 387 | C₄H₉(C₂H₅)N | CH₃ | =S | — | H | H | A | CH₃ | — |
| 388 | CH₃OCH₂CH(C₂H₅)NH | CH₃ | =S | — | H | H | A | CH₃ | — |
| 389 | (CH₃O(CH₂)₂)₂N | CH₃ | =S | — | H | H | A | CH₃ | — |
| 390 | (CH₃)₂NCH₂CH(C₃H₇)NH | CH₃ | =S | — | H | H | A | CH₃ | — |
| 391 | o-CF₃—C₆H₄ | CH₃ | =S | — | H | H | A | CH₃ | — |
| 392 | (C₂H₅)₂CHNH | CH₃ | =S | — | H | H | A | CH₃ | — |
| 393 | C₄H₉(C₂H₅)N | CH₃ | =O | — | H | H | A | CH₃ | — |
| 394 | CH₃OCH₂CH(C₂H₅)NH | CH₃ | =O | — | H | H | A | CH₃ | — |
| 395 | (CH₃O(CH₂)₂)₂N | CH₃ | =O | — | H | H | A | CH₃ | — |
| 396 | (CH₃)₂NCH₂CH(C₃H₇)NH | CH₃ | =O | — | H | H | A | CH₃ | — |
| 397 | o-CF₃—C₆H₄ | CH₃ | =O | — | H | H | A | CH₃ | — |
| 398 | (C₂H₅)₂CHHH | CH₃ | =O | — | H | H | A | CH₃ | — |
| 399 | C₄H₉(C₂H₅)N | CH₃ | H | H | H | H | A | CH₃ | — |
| 400 | CH₃OCH₂CH(C₂H₅)NH | CH₃ | H | H | H | H | A | CH₃ | — |

TABLE II-continued

| Ex No | X | R⁴ | R⁵ | R⁶ | R⁷ | R⁸ | R⁹ ᵃ | R¹⁰ | mp, ° C. |
|---|---|---|---|---|---|---|---|---|---|
| 401 | (CH₃O(CH₂)₂)₂N | CH₃ | H | H | H | H | A | CH₃ | — |
| 402 | (CH₃)₂NCH₂CH(C₃H₇)NH | CH₃ | H | H | H | H | A | CH₃ | — |
| 403 | o-CF₃—C₆H₄ | CH₃ | H | H | H | H | A | CH₃ | — |
| 404 | (C₂H₅)₂CHNH | CH₃ | H | H | H | H | A | CH₃ | — |
| 405 | C₄H₉(C₂H₅)N | CH₃ | =O | — | CH₃ | H | A | CH₃ | — |
| 406 | CH₃OCH₂CH(C₂H₅)NH | CH₃ | =O | — | CH₃ | H | A | CH₃ | — |
| 407 | (CH₃O(CH₂)₂)₂N | CH₃ | =O | — | CH₃ | H | A | CH₃ | — |
| 408 | (CH₃)₂NCH₂CH)C₃H₇)NH | CH₃ | =O | — | CH₃ | H | A | CH₃ | — |
| 409 | o-CF₃—C₆H₄ | CH₃ | =O | — | CH₃ | H | A | CH₃ | — |
| 410 | (C₂H₅)₂CHNH | CH₃ | =O | — | CH₃ | H | A | CH₃ | — |
| 411 | C₄H₉(C₂H₅)N | CH₃ | H | H | CH₃ | H | A | CH₃ | — |
| 412 | CH₃OCH₂CH(C₂H₅)NH | CH₃ | H | H | CH₃ | H | A | CH₃ | — |
| 413 | (CH₃O(CH₂)₂)₂N | CH₃ | H | H | CH₃ | H | A | CH₃ | — |
| 414 | (CH₃)₂NCH₂CH(C₃H₇)NH | CH₃ | H | H | CH₃ | H | A | CH₃ | — |
| 415 | o-CF₃—C₆H₄ | CH₃ | H | H | CH₃ | H | A | CH₃ | — |
| 416 | (C₂H₅)₂CHNH | CH₃ | H | H | CH₃ | H | A | CH₃ | — |
| 417 | C₄H₉(C₂H₅)N | CH₂CH=CH₂ | =O | — | H | H | A | CH₃ | — |
| 418 | CH₃OCH₂CH(C₂H₅)NH | CH₂CH=CH₂ | =O | — | H | H | A | CH₃ | — |
| 419 | (CH₃O(CH₂)₂)₂N | CH₂CH=CH₂ | =O | — | H | H | A | CH₃ | — |
| 420 | (CH₃)₂NCH₂CH(C₃H₇)NH | CH₂CH=CH₂ | =O | — | H | H | A | CH₃ | — |
| 421 | o-CF₃—C₆H₄ | CH₂CH=CH₂ | =O | — | H | H | A | CH₃ | — |
| 422 | (C₂H₅)₂CHNH | CH₂CH=CH₂ | =O | — | H | H | A | CH₃ | — |
| 423 | C₄H₉(C₂H₅)N | CH₂CH=CH₂ | H | H | H | H | A | CH₃ | — |
| 424 | CH₃OCH₂CH(C₂H₅)NH | CH₂CH=CH₂ | H | H | H | H | A | CH₃ | — |
| 425 | (CH₃O(CH₂)₂)₂N | CH₂CH=CH₂ | H | H | H | H | A | CH₃ | — |
| 426 | (CH₃)₂NCH₂CH(C₃H₇)NH | CH₂CH=CH₂ | H | H | H | H | A | CH₃ | — |
| 427 | o-CF₃—C₆H₄ | CH₂CH=CH₂ | H | H | H | H | A | CH₃ | — |
| 428 | (C₂H₅)₂CHNH | CH₂CH=CH₂ | H | H | H | H | A | CH₃ | — |
| 429 | C₄H₉(C₂H₅)N | CH₂CH=CH₂ | =O | — | CH₂CH=CH₂ | H | A | CH₃ | — |
| 430 | CH₃OCH₂CH(C₂H₅)NH | CH₂CH=CH₂ | =O | — | CH₂CH=CH7 | H | A | CH₃ | — |
| 431 | (CH₃O(CH₂)₂)₂N | CH₂CH=CH₂ | =O | — | CH₂CH=CH₂ | H | A | CH₃ | — |
| 432 | (CH₃)₂NCH₂CH(C₃H₇)NH | CH₂CH=CH₂ | =O | — | CH₂CH=CH₂ | H | A | CH₃ | — |
| 433 | o-CF₃—C₆H₄ | CH₃ | =O | — | CH₂CH=CH₂ | H | A | CH₃ | — |
| 434 | (C₂H₅)₂CHNH | CH₂CH=CH₂ | =O | — | CH₂CH=CH₂ | H | A | CH₃ | — |
| 435 | C₄H₉(C₂H₅)N | CH₂CH=CH₂ | H | H | CH₂CH=CH₂ | H | A | CH₃ | — |
| 436 | CH₃OCH₂CH(C₂H₅)NH | CH₂CH=CH₂ | H | H | CH₂CH=CH₂ | H | A | CH₃ | — |
| 437 | (CH₃O(CH₂)₂)₂N | CH₂CH=CH₂ | H | H | CH₂CH=CH₂ | H | A | CH₃ | — |
| 438 | (CH₃)₂NCH₂CH(C₃H₇)NH | CH₂CH=CH₂ | H | H | CH₂CH-CH₂ | H | A | CH₃ | — |
| 439 | o-CF₃—C₆H₄ | CH₂CH=CH₂ | H | H | CH₂CH=CH₂ | H | A | CH₃ | — |
| 440 | (C₂H₅)₂CHNH | CH₂CH=CH₂ | H | H | CH₂CH=CH₂ | H | A | CH₃ | — |
| 441 | C₄H₉(C₂H₅)N | H | CH₃ | CH₃ | H | H | A | CH₃ | — |
| 442 | CH₃OCH₂CH(C₂H₅)NH | H | CH₃ | CH₃ | H | H | A | CH₃ | — |
| 443 | (CH₃O(CH₂)₂)₂N | H | CH₃ | CH₃ | H | H | A | CH₃ | — |
| 444 | (CH₃)₂NCH₂CH(C₃H₇)NH | H | CH₃ | CH₃ | H | H | A | CH₃ | — |
| 445 | o-CF₃—C₆H₄ | H | CH₃ | CH₃ | H | H | A | CH₃ | — |
| 446 | (C₂H₅)₂CHNH | H | CH₃ | CH₃ | H | H | A | CH₃ | — |
| 447 | C₄H₉(C₂H₅)N | H | =O | — | CH₃ | CH₃ | A | CH₃ | — |
| 448 | CH₃OCH₂CH(C₂H₅)NH | H | =O | — | CH₃ | CH₃ | A | CH₃ | — |
| 449 | (CH₃O(CH₂)₂)₂N | H | =O | — | CH₃ | CH₃ | A | CH₃ | — |
| 450 | (CH₃)₂NCH₂CH(C₃H₇)NH | H | =O | — | CH₃ | CH₃ | A | CH₃ | — |
| 451 | o-CF₃—C₆H₄ | H | =O | — | CH₃ | CH₃ | A | CH₃ | — |
| 452 | (C₂H₅)₂CHNH | H | =O | — | CH₃ | CH₃ | A | CH₃ | — |
| 453 | C₄H₉(C₂H₅)N | H | H | H | CH₃ | CH₃ | A | CH₃ | — |
| 454 | CH₃OCH₂CH(C₂H₅)NH | H | H | H | CH₃ | CH₃ | A | CH₃ | — |
| 455 | (CH₃O(CH₂)₂)₂N | H | H | H | CH₃ | CH₃ | A | CH₃ | — |
| 456 | (CH₃)₂NCH₂CH(C₃H₇)NH | H | H | H | CH₃ | CH₃ | A | CH₃ | — |
| 457 | o-CF₃—C₆H₄ | H | H | H | CH₃ | CH₃ | A | CH₃ | — |
| 458 | (C₂H₅)₂CHNH | H | H | H | CH₃ | CH₃ | A | CH₃ | — |
| 459 | C₄H₉(C₂H₅)N | H | =O | — | H | H | A | H | — |
| 460 | CH₃OCH₂CH(C₂H₅)NH | H | =O | — | H | H | A | H | — |
| 461 | (CH₃O(CH₂)₂)₂N | H | =O | — | H | H | A | H | — |
| 462 | (CH₃)₂NCH₂CH)C₃H₇)NH | H | =O | — | H | H | A | H | — |
| 463 | o-CF₃—C₆H₄ | H | =O | — | H | H | A | H | — |
| 464 | (C₂H₅)₂CHNH | H | =O | — | H | H | A | H | — |
| 465 | C₄H₉(C₂H₅)N | H | H | H | H | H | A | H | — |
| 466 | CH₃OCH₂CH(C₂H₅)NH | H | H | H | H | H | A | H | — |

TABLE II-continued

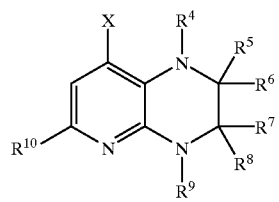

| Ex No | X | R⁴ | R⁵ | R⁶ | R⁷ | R⁸ | R⁹ ᵃ | R¹⁰ | mp, °C. |
|---|---|---|---|---|---|---|---|---|---|
| 467 | $(CH_3O)CH_2)_2)_2N$ | H | H | H | H | H | A | H | — |
| 468 | $(CH_3)_2NCH_2CH(C_3H_7)NH$ | H | H | H | H | H | A | H | — |
| 469 | $o\text{-}CF_3\text{—}C_6H_4$ | H | H | H | H | H | A | H | — |
| 470 | $(C_2H_5)_2CHNH$ | H | H | H | H | H | A | H | — |
| 471 | $C_4H_9(C_2H_5)N$ | H | =O | — | H | H | A | CN | — |
| 472 | $CH_3OCH_2CH(C_2H_5)NH$ | H | =O | — | H | H | A | CN | — |
| 473 | $(CH_3O(CH_2)_2)_2N$ | H | =O | — | H | H | A | CN | — |
| 474 | $(CH_3)_2NCH_2CH(C_3H_7)NH$ | H | =O | — | H | H | A | CN | — |
| 475 | $o\text{-}CF_3\text{—}C_6H_4$ | H | =O | — | H | H | A | CN | — |
| 476 | $(C_2H_5)_2CHNH$ | H | =O | — | H | H | A | CN | — |
| 477 | $C_4H_9(C_2H_5)N$ | H | H | H | H | H | A | CN | — |
| 478 | $CH_3OCH_2CH(C_2H_5)NH$ | H | H | H | H | H | A | CN | — |
| 479 | $(CH_3O(CH_2)_2)_2N$ | H | H | H | H | H | A | CN | — |
| 480 | $(CH_3)_2NCH_2CH(C_3H_7)NH$ | H | H | H | H | H | A | CN | — |
| 481 | $o\text{-}CF_3\text{—}C_6H_4$ | H | H | H | H | H | A | CN | — |
| 482 | $(C_2H_5)_2CHNH$ | H | H | H | H | H | A | CN | — |
| 483 | 2-morpholinyl | H | H | H | H | H | A | $CH_3$ | — |
| 484 | 2-morpholinyl | H | =O | — | H | H | B | $CH_3$ | — |
| 485 | 2-morpholinyl | H | =O | — | H | H | C | $CH_3$ | — |
| 486 | 2-morpholinyl | H | =O | — | H | H | D | $CH_3$ | — |
| 487 | 2-morpholinyl | H | =O | — | H | H | E | $CH_3$ | — |
| 488 | 2-morpholinyl | H | =O | — | H | H | F | $CH_3$ | — |
| 489 | 2-morpholinyl | H | =O | — | H | H | G | $CH_3$ | — |
| 490 | 2-morpholinyl | H | =O | — | H | H | J | $CH_3$ | — |
| 491 | 2-morpholinyl | H | H | H | H | H | B | $CH_3$ | — |
| 492 | 2-morpholinyl | H | H | H | H | H | C | $CH_3$ | — |
| 493 | 2-morpholinyl | H | H | H | H | H | D | $CH_3$ | — |
| 494 | 2-morpholinyl | H | H | H | H | H | E | $CH_3$ | — |
| 495 | 2-morpholinyl | H | H | H | H | H | F | $CH_3$ | — |
| 496 | 2-morpholinyl | H | H | H | H | H | G | $CH_3$ | — |
| 497 | 2-morpholinyl | H | H | H | H | H | J | $CH_3$ | — |
| 498 | $C_4H_9(C_2H_5)N$ | H | =NH | — | H | H | A | $CH_3$ | — |
| 499 | $C_4H_9(C_2H_5)N$ | H | =NH | — | H | H | C | $CH_3$ | — |
| 500 | $C_4H_9(C_2H_5)N$ | H | $=NC_4H_9$ | — | H | H | A | $CH_3$ | — |

Key:
(a) R⁹ group codes:

A = 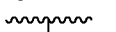

B = 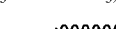

TABLE II-continued
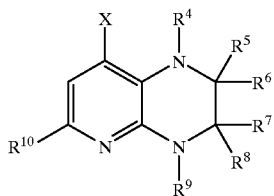
| Ex No | X | R⁴ | R⁵ | R⁶ | R⁷ | R⁸ | R⁹ ᵃ | R¹⁰ | mp, °C. |
|---|---|---|---|---|---|---|---|---|---|
C = 2,4,6-trimethylphenyl (H₃C, CH₃, CH₃);
D = 2-bromo-4-iodophenyl (Br, I);
E = 2-bromo-4-(methylthio)phenyl (Br, SCH₃);
F = 2-bromo-4-cyanophenyl (Br, CN);
G = 2-bromo-3,5-dimethoxyphenyl (H₃CO, Br, OCH₃);
J = 2,4,6-trimethylpyridin-3-yl (H₃C, CH₃, CH₃).

TABLE III

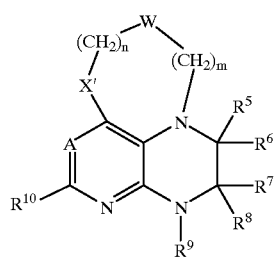

| Ex. No. | A | X' | n | W | m | R⁵ | R⁶ | R⁷ | R⁸ | R⁹ᵃ | R¹⁰ | m.p. |
|---|---|---|---|---|---|---|---|---|---|---|---|---|
| 501 | N | C₄H₉N | 0 | C=O | 1 | =O | — | H | H | A | CH₃ | 207–208 |
| 502 | N | C₄H₉N | 0 | C=O | 1 | =O | — | H | H | B | CH₃ | — |
| 503 | N | C₄H₉N | 0 | C=O | 1 | =O | — | H | H | C | CH₃ | — |
| 504 | N | C₄H₉N | 0 | C=O | 1 | =O | — | H | H | D | CH₃ | — |
| 505 | N | C₄H₉N | 0 | C=O | 1 | =O | — | H | H | E | CH₃ | — |
| 506 | N | C₄H₉N | 0 | C=O | 1 | =O | — | H | H | F | CH₃ | — |
| 507 | N | C₄H₉N | 0 | C=O | 1 | =O | — | H | H | G | CH₃ | — |
| 508 | N | C₄H₉N | 0 | C=O | 1 | =O | — | H | H | J | CH₃ | — |
| 509 | N | (C₂H₅)₂CHN | 0 | C=O | 1 | =O | — | H | H | A | CH₃ | — |
| 510 | N | (C₂H₅)₂CHN | 0 | C=O | 1 | =O | — | H | H | B | CH₃ | — |
| 511 | N | (C₂H₅)₂CHN | 0 | C=O | 1 | =O | — | H | H | C | CH₃ | — |
| 512 | N | CH₃OCH₂CH(C₂H₅)N | 0 | C=O | 1 | =O | — | H | H | A | CH₃ | — |
| 513 | N | CH₃OCH₂CH(C₂H₅)N | 0 | C=O | 1 | =O | — | H | H | B | CH₃ | — |
| 514 | N | CH₃OCH₂CH(C₂H₅)N | 0 | C=O | 1 | =O | — | H | H | C | CH₃ | — |
| 515 | N | C₄H₉CH(C₂H₅)N | 0 | C=O | 1 | =O | — | H | H | A | CH₃ | — |
| 516 | N | C₄H₉CH(C₂H₅)N | 0 | C=O | 1 | =O | — | H | H | B | CH₃ | — |
| 517 | N | C₄H₉CH(C₂H₅)N | 0 | C=O | 1 | =O | — | H | H | C | CH₃ | — |
| 518 | N | C₄H₉N | 0 | CH₂ | 1 | H | H | H | H | A | CH₃ | — |
| 519 | N | C₄H₉N | 0 | CH₂ | 1 | H | H | H | H | B | CH₃ | — |
| 520 | N | C₄H₉N | 0 | CH₂ | 1 | H | H | H | H | C | CH₃ | — |
| 521 | N | (C₂H₅)₂CHN | 0 | CH₂ | 1 | H | H | H | H | A | CH₃ | — |
| 522 | N | (C₂H₅)₂CHN | 0 | CH₂ | 1 | H | H | H | H | B | CH₃ | — |
| 523 | N | (C₂H₅)₂CHN | 0 | CH₂ | 1 | H | H | H | H | C | CH₃ | — |
| 524 | N | CH₃OCH₂CH(C₂H₅)N | 0 | CH₂ | 1 | H | H | H | H | A | CH₃ | — |
| 525 | N | CH₃OCH₂CH(C₂H₅)N | 0 | CH₂ | 1 | H | H | H | H | B | CH₃ | — |
| 526 | N | CH₃OCH₂CH(C₂H₅)N | 0 | CH₂ | 1 | H | H | H | H | C | CH₃ | — |
| 527 | N | C₄H₉CH(C₂H₅)N | 0 | CH₂ | 1 | H | H | H | H | A | CH₃ | — |
| 528 | N | C₄H₉CH(C₂H₅)N | 0 | CH₂ | 1 | H | H | H | H | B | CH₃ | — |
| 529 | N | C₄H₉CH(C₂H₅)N | 0 | CH₂ | 1 | H | H | H | H | C | CH₃ | — |
| 530 | N | C₄H₉N | 1 | CH₂ | 1 | =O | — | H | H | A | CH₃ | — |
| 531 | N | C₄H₉N | 1 | CH₂ | 1 | =O | — | H | H | B | CH₃ | — |
| 532 | N | C₄H₉N | 1 | CH₂ | 1 | =O | — | H | H | C | CH₃ | — |
| 533 | N | (C₂H₅)₂CHN | 1 | CH₂ | 1 | =O | — | H | H | A | CH₃ | — |
| 534 | N | (C₂H₅)₂CHN | 1 | CH₂ | 1 | =O | — | H | H | B | CH₃ | — |
| 535 | N | (C₂H₅)₂CHN | 1 | CH₂ | 1 | =O | — | H | H | C | CH₃ | — |
| 536 | N | CH₃OCH₂CH(C₂H₅)N | 1 | CH₂ | 1 | =O | — | H | H | A | CH₃ | — |
| 537 | N | CH₃OCH₂CH(C₂H₅)N | 1 | CH₂ | 1 | =O | — | H | H | B | CH₃ | — |
| 538 | N | CH₃OCH₂CH(C₂H₅)N | 1 | CH₂ | 1 | =O | — | H | H | C | CH₃ | — |
| 539 | N | C₄H₉CH(C₂H₅)N | 1 | CH₂ | 1 | =O | — | H | H | A | CH₃ | — |
| 540 | N | C₄H₉CH(C₂H₅)N | 1 | CH₂ | 1 | =O | — | H | H | B | CH₃ | — |
| 541 | N | C₄H₉CH(C₂H₅)N | 1 | CH₂ | 1 | =O | — | H | H | C | CH₃ | — |
| 542 | N | C₄H₉N | 1 | CH₂ | 1 | H | H | H | H | A | CH₃ | — |
| 543 | N | C₄H₉N | 1 | CH₂ | 1 | H | H | H | H | B | CH₃ | — |
| 544 | N | C₄H₉N | 1 | CH₂ | 1 | H | H | H | H | C | CH₃ | — |
| 545 | N | (C₅H₅)₂CHN | 1 | CH₂ | 1 | H | H | H | H | A | CH₃ | — |
| 546 | N | (C₅H₅)₂CHN | 1 | CH₂ | 1 | H | H | H | H | B | CH₃ | — |
| 547 | N | (C₅H₅)₂CHN | 1 | CH₂ | 1 | H | H | H | H | C | CH₃ | — |
| 548 | N | CH₃OCH₂CH(C₂H₅)N | 1 | CH₂ | 1 | H | H | H | H | A | CH₃ | — |
| 549 | N | CH₃OCH₂CH(C₂H₅)N | 1 | CH₂ | 1 | H | H | H | H | B | CH₃ | — |
| 550 | N | CH₃OCH₂CH(C₂H₅)N | 1 | CH₂ | 1 | H | H | H | H | C | CH₃ | — |
| 551 | N | C₄H₉CH(C₂H₅)N | 1 | CH₂ | 1 | H | H | H | H | A | CH₃ | — |
| 552 | N | C₄H₉CH(C₂H₅)N | 1 | CH₂ | 1 | H | H | H | H | B | CH₃ | — |
| 553 | N | C₄H₉CH(C₂H₅)N | 1 | CH₂ | 1 | H | H | H | H | C | CH₃ | — |
| 554 | N | C₄H₉N | 0 | CH₂ | 1 | =O | — | H | H | A | CH₃ | — |
| 555 | N | C₄H₉N | 0 | CH₂ | 1 | =O | — | H | H | B | CH₃ | — |
| 556 | N | C₄H₉N | 0 | CH₂ | 1 | =O | — | H | H | C | CH₃ | — |
| 557 | N | (C₂H₅)₂CHN | 0 | CH₂ | 1 | =O | — | H | H | A | CH₃ | — |
| 558 | N | (C₂H₅)₂CHN | 0 | CH₂ | 1 | =O | — | H | H | B | CH₃ | — |
| 559 | N | (C₂H₅)₂CHN | 0 | CH₂ | 1 | =O | — | H | H | C | CH₃ | — |
| 560 | N | CH₃OCH₂CH(C₂H₅)N | 0 | CH₂ | 1 | =O | — | H | H | A | CH₃ | — |
| 561 | N | CH₃OCH₂CH(C₂H₅)N | 0 | CH₂ | 1 | =O | — | H | H | B | CH₃ | — |
| 562 | N | CH₃OCH₂CH(C₂H₅)N | 0 | CH₂ | 1 | =O | — | H | H | C | CH₃ | — |
| 563 | N | C₄CH(C₂H₅)N | 0 | CH₂ | 1 | =O | — | H | H | A | CH₃ | — |

TABLE III-continued

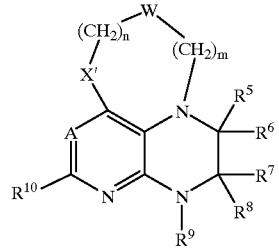

| Ex. No. | A | X' | n | W | m | R⁵ | R⁶ | R⁷ | R⁸ | R⁹ᵃ | R¹⁰ | m.p. |
|---|---|---|---|---|---|---|---|---|---|---|---|---|
| 564 | N | C₄CH(C₂H₅)N | 0 | CH₂ | 1 | =O | — | H | H | B | CH₃ | — |
| 565 | N | C₄CH(C₂H₅)N | 0 | CH₂ | 1 | =O | — | H | H | C | CH₃ | — |
| 566 | N | C₄H₉N | 1 | C=O | 1 | =O | — | H | H | A | CH₃ | — |
| 567 | N | C₄H₉N | 1 | C=O | 1 | =O | — | H | H | B | CH₃ | — |
| 568 | N | C₄H₉N | 1 | C=O | 1 | =O | — | H | H | C | CH₃ | — |
| 569 | N | (C₂H₅)₂CHN | 1 | C=O | 1 | =O | — | H | H | A | CH₃ | — |
| 570 | N | (C₂H₅)₂CHN | 1 | C=O | 1 | =O | — | H | H | B | CH₃ | — |
| 571 | N | (C₂H₅)₂CHN | 1 | C=O | 1 | =O | — | H | H | C | CH₃ | — |
| 572 | N | CH₃OCH₂CH(C₂H₅)N | 1 | C=O | 1 | =O | — | H | H | A | CH₃ | — |
| 573 | N | CH₃OCH₂CH(C₂H₅)N | 1 | C=O | 1 | =O | — | H | H | B | CH₃ | — |
| 574 | N | CH₃OCH₂CH(C₂H₅)N | 1 | C=O | 1 | =O | — | H | H | C | CH₃ | — |
| 575 | N | C₄H₉CH(C₂H₅)N | 1 | C=O | 1 | =O | — | H | H | A | CH₃ | — |
| 576 | N | C₄H₉CH(C₂H₅)N | 1 | C=O | 1 | =O | — | H | H | B | CH₃ | — |
| 577 | N | C₄H₉CH(C₂H₅)N | 1 | C=O | 1 | =O | — | H | H | C | CH₃ | — |
| 578 | N | C₄H₉N | 1 | C=O | 0 | H | H | H | H | A | CH₃ | — |
| 579 | N | C₄H₉N | 1 | C=O | 0 | H | H | H | H | B | CH₃ | — |
| 580 | N | C₄H₉N | 1 | C=O | 0 | H | H | H | H | C | CH₃ | — |
| 581 | N | (C₂H₅)₂CHN | 1 | C=O | 0 | H | H | H | H | A | CH₃ | — |
| 582 | N | (C₂H₅)₂CHN | 1 | C=O | 0 | H | H | H | H | B | CH₃ | — |
| 583 | N | (C₂H₅)₂CHN | 1 | C=O | 0 | H | H | H | H | C | CH₃ | — |
| 584 | N | CH₃OCH₂CH(C₂H₅)N | 1 | C=O | 0 | H | H | H | H | A | CH₃ | — |
| 585 | N | CH₃OCH₂CH(C₂H₅)N | 1 | C=O | 0 | H | H | H | H | B | CH₃ | — |
| 586 | N | CH₃OCH₂CH(C₂H₅)N | 1 | C=O | 0 | H | H | H | H | C | CH₃ | — |
| 587 | N | C₄H₉CH(C₂H₅)N | 1 | C=O | 0 | H | H | H | H | A | CH₃ | — |
| 588 | N | C₄H₉CH(C₂H₅)N | 1 | C=O | 0 | H | H | H | H | B | CH₃ | — |
| 589 | N | C₄H₉CH(C₂H₅)N | 1 | C=O | 0 | H | H | H | H | C | CH₃ | — |
| 590 | N | C₄H₉N | 0 | C=O | 0 | H | H | H | H | A | CH₃ | — |
| 591 | N | C₄H₉N | 0 | C=O | 0 | H | H | H | H | B | CH₃ | — |
| 592 | N | C₄H₉N | 0 | C=O | 0 | H | H | H | H | C | CH₃ | — |
| 593 | N | (C₂H₅)₂CHN | 0 | C=O | 0 | H | H | H | H | A | CH₃ | — |
| 594 | N | (C₂H₅)₂CHN | 0 | C=O | 0 | H | H | H | H | B | CH₃ | — |
| 595 | N | (C₂H₅)₂CHN | 0 | C=O | 0 | H | H | H | H | C | CH₃ | — |
| 596 | N | CH₃OCH₂CH(C₂H₅)N | 0 | C=O | 0 | H | H | H | H | A | CH₃ | — |
| 597 | N | CH₃OCH₂CH(C₂H₅)N | 0 | C=O | 0 | H | H | H | H | B | CH₃ | — |
| 598 | N | CH₃OCH₂CH(C₂H₅)N | 0 | C=O | 0 | H | H | H | H | C | CH₃ | — |
| 599 | N | C₄H₉CH(C₂H₅)N | 0 | C=O | 0 | H | H | H | H | A | CH₃ | — |
| 600 | N | C₄H₉CH(C₂H₅)N | 0 | C=O | 0 | H | H | H | H | B | CH₃ | — |
| 601 | N | C₄H₉CH(C₂H₅)N | 0 | C=O | 0 | H | H | H | H | C | CH₃ | — |
| 602 | CH | C₄H₉N | 0 | C=O | 1 | =O | — | H | H | A | CH₃ | — |
| 603 | CH | C₄H₉N | 0 | C=O | 1 | =O | — | H | H | B | CH₃ | — |
| 604 | CH | C₄H₉N | 0 | C=O | 1 | =O | — | H | H | C | CH₃ | — |
| 605 | CH | (C₂H₅)₂CHN | 0 | C=O | 1 | =O | — | H | H | A | CH₃ | — |
| 606 | CH | (C₂H₅)₂CHN | 0 | C=O | 1 | =O | — | H | H | B | CH₃ | — |
| 607 | CH | (C₂H₅)₂CHN | 0 | C=O | 1 | =O | — | H | H | C | CH₃ | — |
| 608 | CH | CH₃OCH₂CH(C₂H₅)N | 0 | C=O | 1 | =O | — | H | H | A | CH₃ | — |
| 609 | CH | CH₃OCH₂CH(C₂H₅)N | 0 | C=O | 1 | =O | — | H | H | B | CH₃ | — |
| 610 | CH | CH₃OCH₂CH(C₂H₅)N | 0 | C=O | 1 | =O | — | H | H | C | CH₃ | — |
| 611 | CH | C₄H₉CH(C₂H₅)N | 0 | C=O | 1 | =O | — | H | H | A | CH₃ | — |
| 612 | CH | C₄H₉CH(C₂H₅)N | 0 | C=O | 1 | =O | — | H | H | B | CH₃ | — |
| 613 | CH | C₄H₉CH(C₂H₅)N | 0 | C=O | 1 | =O | — | H | H | C | CH₃ | — |
| 614 | CH | C₄H₉N | 0 | CH₂ | 1 | H | H | H | H | A | CH₃ | — |
| 615 | CH | C₄H₉N | 0 | CH₂ | 1 | H | H | H | H | B | CH₃ | — |
| 616 | CH | C₄H₉N | 0 | CH₂ | 1 | H | H | H | H | C | CH₃ | — |
| 617 | CH | (C₂H₅)₂CHN | 0 | CH₂ | 1 | H | H | H | H | A | CH₃ | — |
| 618 | CH | (C₂H₅)₂CHN | 0 | CH₂ | 1 | H | H | H | H | B | CH₃ | — |
| 619 | CH | (C₂H₅)₂CHN | 0 | CH₂ | 1 | H | H | H | H | C | CH₃ | — |
| 620 | CH | CH₃OCH₂CH(C₂H₅)N | 0 | CH₂ | 1 | H | H | H | H | A | CH₃ | — |
| 621 | CH | CH₃OCH₂CH(C₂H₅)N | 0 | CH₂ | 1 | H | H | H | H | B | CH₃ | — |
| 622 | CH | CH₃OCH₂CH(C₂H₅)N | 0 | CH₂ | 1 | H | H | H | H | C | CH₃ | — |
| 623 | CH | C₄H₉CH(C₂H₅)N | 0 | CH₂ | 1 | H | H | H | H | A | CH₃ | — |
| 624 | CH | C₄H₉CH(C₂H₅)N | 0 | CH₂ | 1 | H | H | H | H | B | CH₃ | — |
| 625 | CH | C₄H₉CH(C₂H₅)N | 0 | CH₂ | 1 | H | H | H | H | C | CH₃ | — |
| 626 | CH | C₄H₉N | 1 | CH₂ | 1 | =O | — | H | H | A | CH₃ | — |

TABLE III-continued

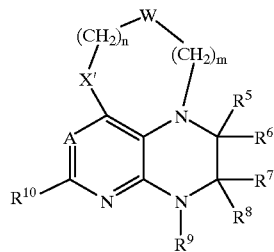

| Ex. No. | A | X' | n | W | m | R⁵ | R⁶ | R⁷ | R⁸ | R⁹ᵃ | R¹⁰ | m.p. |
|---|---|---|---|---|---|---|---|---|---|---|---|---|
| 627 | CH | C₄H₉N | 1 | CH₂ | 1 | =O | — | H | H | B | CH₃ | — |
| 628 | CH | C₄H₉N | 1 | CH₂ | 1 | =O | — | H | H | C | CH₃ | — |
| 629 | CH | (C₂H₅)₂CHN | 1 | CH₂ | 1 | =O | — | H | H | A | CH₃ | — |
| 630 | CH | (C₂H₅)₂CHN | 1 | CH₂ | 1 | =O | — | H | H | B | CH₃ | — |
| 631 | CH | (C₂H₅)₂CHN | 1 | CH₂ | 1 | =O | — | H | H | C | CH₃ | — |
| 632 | CH | CH₃OCH₂CH(C₂H₅)N | 1 | CH₂ | 1 | =O | — | H | H | A | CH₃ | — |
| 633 | CH | CH₃OCH₂CH(C₂H₅)N | 1 | CH₂ | 1 | =O | — | H | H | B | CH₃ | — |
| 634 | CH | CH₃OCH₂CH(C₂H₅)N | 1 | CH₂ | 1 | =O | — | H | H | C | CH₃ | — |
| 635 | CH | C₄H₉CH(C₂H₅)N | 1 | CH₂ | 1 | =O | — | H | H | A | CH₃ | — |
| 636 | CH | C₄H₉CH(C₂H₅)N | 1 | CH₂ | 1 | =O | — | H | H | B | CH₃ | — |
| 637 | CH | C₄H₉CH(C₂H₅)N | 1 | CH₂ | 1 | =O | — | H | H | C | CH₃ | — |
| 638 | CH | C₄H₉N | 1 | CH₂ | 1 | H | H | H | H | A | CH₃ | — |
| 639 | CH | C₄H₉N | 1 | CH₂ | 1 | H | H | H | H | B | CH₃ | — |
| 640 | CH | C₄H₉N | 1 | CH₂ | 1 | H | H | H | H | C | CH₃ | — |
| 641 | CH | (C₂H₅)₂CHN | 1 | CH₂ | 1 | H | H | H | H | A | CH₃ | — |
| 642 | CH | (C₂H₅)₂CHN | 1 | CH₂ | 1 | H | H | H | H | B | CH₃ | — |
| 643 | CH | (C₂H₅)₂CHN | 1 | CH₂ | 1 | H | H | H | H | C | CH₃ | — |
| 644 | CH | CH₃OCH₂CH(C₂H₅)N | 1 | CH₂ | 1 | H | H | H | H | A | CH₃ | — |
| 645 | CH | CH₃OCH₂CH(C₂H₅)N | 1 | CH₂ | 1 | H | H | H | H | B | CH₃ | — |
| 646 | CH | CH₃OCH₂CH(C₂H₅)N | 1 | CH₂ | 1 | H | H | H | H | C | CH₃ | — |
| 647 | CH | C₄H₉CH(C₂H₅)N | 1 | CH₂ | 1 | H | H | H | H | A | CH₃ | — |
| 648 | CH | C₄H₉CH(C₂H₅)N | 1 | CH₂ | 1 | H | H | H | H | B | CH₃ | — |
| 649 | CH | C₄H₉CH(C₂H₅)N | 1 | CH₂ | 1 | H | H | H | H | C | CH₃ | — |
| 650 | CH | C₄H₉N | 0 | CH₂ | 1 | =O | — | H | H | A | CH₃ | — |
| 651 | CH | C₄H₉N | 0 | CH₂ | 1 | =O | — | H | H | B | CH₃ | — |
| 652 | CH | C₄H₉N | 0 | CH₂ | 1 | =O | — | H | H | C | CH₃ | — |
| 653 | CH | (C₂H₅)₂CHN | 0 | CH₂ | 1 | =O | — | H | H | A | CH₃ | — |
| 654 | CH | (C₂H₅)₂CHN | 0 | CH₂ | 1 | =O | — | H | H | B | CH₃ | — |
| 655 | CH | (C₂H₅)₂CHN | 0 | CH₂ | 1 | =O | — | H | H | C | CH₃ | — |
| 656 | CH | CH₃OCH₂CH(C₂H₅)N | 0 | CH₂ | 1 | =O | — | H | H | A | CH₃ | — |
| 657 | CH | CH₃OCH₂CH(C₂H₅)N | 0 | CH₂ | 1 | =O | — | H | H | B | CH₃ | — |
| 658 | CH | CH₃OCH₂CH(C₂H₅)N | 0 | CH₂ | 1 | =O | — | H | H | C | CH₃ | — |
| 659 | CH | C₄H₉CH(C₂H₅)N | 0 | CH₂ | 1 | =O | — | H | H | A | CH₃ | — |
| 660 | CH | C₄H₉CH(C₂H₅)N | 0 | CH₂ | 1 | =O | — | H | H | B | CH₃ | — |
| 661 | CH | C₄H₉CH(C₂H₅)N | 0 | CH₂ | 1 | =O | — | H | H | C | CH₃ | — |
| 662 | CH | C₄H₉N | 1 | C=O | 1 | =O | — | H | H | A | CH₃ | — |
| 663 | CH | C₄H₉N | 1 | C=O | 1 | =O | — | H | H | B | CH₃ | — |
| 664 | CH | C₄H₉N | 1 | C=O | 1 | =O | — | H | H | C | CH₃ | — |
| 665 | CH | (C₂H₅)₂CHN | 1 | C=O | 1 | =O | — | H | H | A | CH₃ | — |
| 666 | CH | (C₂H₅)₂CHN | 1 | C=O | 1 | =O | — | H | H | B | CH₃ | — |
| 667 | CH | (C₂H₅)₂CHN | 1 | C=O | 1 | =O | — | H | H | C | CH₃ | — |
| 668 | CH | CH₃OCH₂CH(C₂H₅)N | 1 | C=O | 1 | =O | — | H | H | A | CH₃ | — |
| 669 | CH | CH₃OCH₂CH(C₂H₅)N | 1 | C=O | 1 | =O | — | H | H | B | CH₃ | — |
| 670 | CH | CH₃OCH₂CH(C₂H₅)N | 1 | C=O | 1 | =O | — | H | H | C | CH₃ | — |
| 671 | CH | C₄H₉CH(C₂H₅)N | 1 | C=O | 1 | =O | — | H | H | A | CH₃ | — |
| 672 | CH | C₄H₉CH(C₂H₅)N | 1 | C=O | 1 | =O | — | H | H | B | CH₃ | — |
| 673 | CH | C₄H₉CH(C₂H₅)N | 1 | C=O | 1 | =O | — | H | H | C | CH₃ | — |
| 674 | CH | C₄H₉N | 1 | C=O | 0 | H | H | H | H | A | CH₃ | — |
| 675 | CH | C₄H₉N | 1 | C=O | 0 | H | H | H | H | B | CH₃ | — |
| 676 | CH | C₄H₉N | 1 | C=O | 0 | H | H | H | H | C | CH₃ | — |
| 677 | CH | (C₂H₅)₂CHN | 1 | C=O | 0 | H | H | H | H | A | CH₃ | — |
| 678 | CH | (C₂H₅)₂CHN | 1 | C=O | 0 | H | H | H | H | B | CH₃ | — |
| 679 | CH | (C₂H₅)₂CHN | 1 | C=O | 0 | H | H | H | H | C | CH₃ | — |
| 680 | CH | CH₃OCH₂CH(C₂H₅)N | 1 | C=O | 0 | H | H | H | H | A | CH₃ | — |
| 681 | CH | CH₃OCH₂CH(C₂H₅)N | 1 | C=O | 0 | H | H | H | H | B | CH₃ | — |
| 682 | CH | CH₃OCH₂CH(C₂H₅)N | 1 | C=O | 0 | H | H | H | H | C | CH₃ | — |
| 683 | CH | C₄H₉CH(C₂H₅)N | 1 | C=O | 0 | H | H | H | H | A | CH₃ | — |
| 684 | CH | C₄H₉CH(C₂H₅)N | 1 | C=O | 0 | H | H | H | H | B | CH₃ | — |
| 685 | CH | C₄H₉CH(C₂H₅)N | 1 | C=O | 0 | H | H | H | H | C | CH₃ | — |
| 686 | CH | C₄H₉N | 0 | C=O | 0 | H | H | H | H | A | CH₃ | — |
| 687 | CH | C₄H₉N | 0 | C=O | 0 | H | H | H | H | B | CH₃ | — |
| 688 | CH | C₄H₉N | 0 | C=O | 0 | H | H | H | H | C | CH₃ | — |
| 689 | CH | (C₂H₅)₂CHN | 0 | C=O | 0 | H | H | H | H | A | CH₃ | — |

TABLE III-continued

![structure]

| Ex. No. | A | X' | n | W | m | R⁵ | R⁶ | R⁷ | R⁸ | R⁹ᵃ | R¹⁰ | m.p. |
|---|---|---|---|---|---|---|---|---|---|---|---|---|
| 690 | CH | $(C_2H_5)_2CHN$ | 0 | C=O | 0 | H | H | H | H | B | $CH_3$ | — |
| 691 | CH | $(C_2H_5)_2CHN$ | 0 | C=O | 0 | H | H | H | H | C | $CH_3$ | — |
| 692 | CH | $CH_3OCH_2CH(C_2H_5)N$ | 0 | C=O | 0 | H | H | H | H | A | $CH_3$ | — |
| 693 | CH | $CH_3OCH_2CH(C_2H_5)N$ | 0 | C=O | 0 | H | H | H | H | B | $CH_3$ | — |
| 694 | CH | $CH_3OCH_2CH(C_2H_5)N$ | 0 | C=O | 0 | H | H | H | H | C | $CH_3$ | — |
| 695 | CH | $C_4H_9(C_2H_5)N$ | 0 | C=O | 0 | H | H | H | H | A | $CH_3$ | — |
| 696 | CH | $C_4H_9(C_2H_5)N$ | 0 | C=O | 0 | H | H | H | H | B | $CH_3$ | — |
| 697 | CH | $C_4H_9(C_2H_5)N$ | 0 | C=O | 0 | H | H | H | H | C | $CH_3$ | — |
| 698 | N | $[C_2H_5OC(=O)]_2C$ | 0 | $CH_2$ | 1 | =O | — | H | H | A | $CH_3$ | — |
| 699 | N | $[C_2H_5OC(=O)]_2C$ | 0 | $CH_2$ | 1 | =O | — | H | H | B | $CH_3$ | — |
| 700 | N | $[C_2H_5OC(=O)]_2C$ | 0 | $CH_2$ | 1 | =O | — | H | H | C | $CH_3$ | — |
| 701 | N | $[C_2H_5OC(=O)]_2C$ | 0 | $CH_2$ | 1 | H | H | H | H | A | $CH_3$ | — |
| 702 | N | $[C_2H_5OC(=O)]_2C$ | 0 | $CH_2$ | 1 | H | H | H | H | B | $CH_3$ | — |
| 703 | N | $[C_2H_5OC(=O)]_2C$ | 0 | $CH_2$ | 1 | H | H | H | H | C | $CH_3$ | — |
| 704 | N | $(CH_3OCH_2)_2C$ | 0 | $CH_2$ | 1 | H | H | H | H | A | $CH_3$ | — |
| 705 | N | $(CH_3OCH_2)_2C$ | 0 | $CH_2$ | 1 | H | H | H | H | B | $CH_3$ | — |
| 706 | N | $(CH_3OCH_2)_2C$ | 0 | $CH_2$ | 1 | H | H | H | H | C | $CH_3$ | — |
| 707 | N | $(NC)_2C$ | 0 | $CH_2$ | 1 | =O | — | H | H | A | $CH_3$ | — |
| 708 | N | $(NC)_2C$ | 0 | $CH_2$ | 1 | =O | — | H | H | B | $CH_3$ | — |
| 709 | N | $(NC)_2C$ | 0 | $CH_2$ | 1 | =O | — | H | H | C | $CH_3$ | — |
| 710 | N | $[C_2H_5OC(=O)]_2C$ | 1 | $CH_2$ | 1 | =O | — | H | H | A | $CH_3$ | — |
| 711 | N | $[C_2H_5OC(=O)]_2C$ | 1 | $CH_2$ | 1 | =O | — | H | H | B | $CH_3$ | — |
| 712 | N | $[C_2H_5OC(=O)]_2C$ | 1 | $CH_2$ | 1 | =O | — | H | H | C | $CH_3$ | — |
| 713 | N | $[C_2H_5OC(=O)]_2C$ | 1 | $CH_2$ | 1 | H | H | H | H | A | $CH_3$ | — |
| 714 | N | $[C_2H_5OC(=O)]_2C$ | 1 | $CH_2$ | 1 | H | H | H | H | B | $CH_3$ | — |
| 715 | N | $[C_2H_5OC(=O)]_2C$ | 1 | $CH_2$ | 1 | H | H | H | H | C | $CH_3$ | — |
| 716 | N | $(CH_3OCH_2)_2C$ | 1 | $CH_2$ | 1 | H | H | H | H | A | $CH_3$ | — |
| 717 | N | $(CH_3OCH_2)_2C$ | 1 | $CH_2$ | 1 | H | H | H | H | B | $CH_3$ | — |
| 718 | N | $(CH_3OCH_2)_2C$ | 1 | $CH_2$ | 1 | H | H | H | H | C | $CH_3$ | — |

Key: (a) R⁹ group codes:

A = 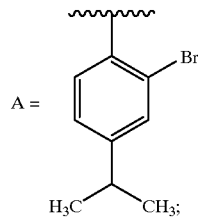

B = 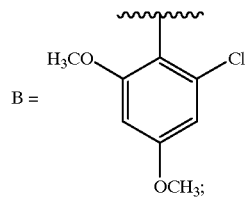

C = 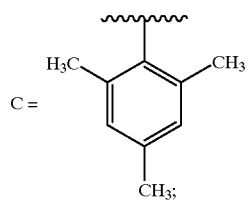

TABLE III-continued
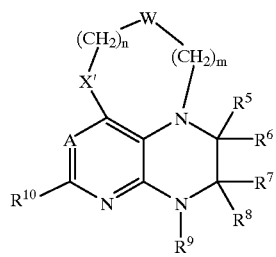
| Ex. No. | A | X' | n | W | m | R⁵ | R⁶ | R⁷ | R⁸ | R⁹ᵃ | R¹⁰ | m.p. |
|---------|---|----|----|---|---|----|----|----|----|-----|-----|------|
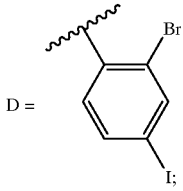
D =
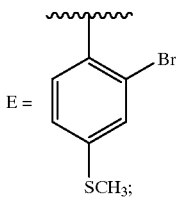
E =
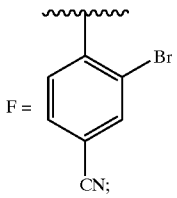
F =
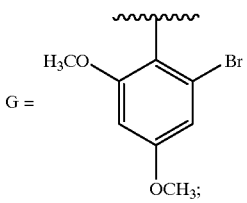
G =
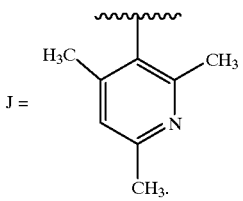
J =

TABLE IV

| Ex. No. | A | X | M | P | Q | R[7] | R[8] | R[9a] | R[10] | m.p. |
|---|---|---|---|---|---|---|---|---|---|---|
| 719 | N | C$_4$H$_9$(C$_2$H$_5$)N | N | N | N | H | H | A | CH$_3$ | b |
| 720 | N | C$_4$H$_9$(C$_2$H$_5$)N | N | N | N | H | H | B | CH$_3$ | — |
| 721 | N | C$_4$H$_9$(C$_2$H$_5$)N | N | N | N | H | H | C | CH$_3$ | — |
| 722 | N | C$_4$H$_9$(C$_2$H$_5$)N | N | N | N | H | H | D | CH$_3$ | — |
| 723 | N | C$_4$H$_9$(C$_2$H$_5$)N | N | N | N | H | H | E | CH$_3$ | — |
| 724 | N | C$_4$H$_9$(C$_2$H$_5$)N | N | N | N | H | H | F | CH$_3$ | — |
| 725 | N | C$_4$H$_9$(C$_2$H$_5$)N | N | N | N | H | H | G | CH$_3$ | — |
| 726 | N | C$_4$H$_9$(C$_2$H$_5$)N | N | N | N | H | H | J | CH$_3$ | — |
| 727 | N | (C$_2$H$_5$)$_2$N | N | N | N | H | H | A | CH$_3$ | — |
| 728 | N | (C$_2$H$_5$)$_2$N | N | N | N | H | H | B | CH$_3$ | — |
| 729 | N | (C$_2$H$_5$)$_2$N | N | N | N | H | H | C | CH$_3$ | — |
| 730 | N | (C$_2$H$_5$)$_2$N | N | N | N | H | H | D | CH$_3$ | — |
| 731 | N | (C$_2$H$_5$)$_2$N | N | N | N | H | H | E | CH$_3$ | — |
| 732 | N | (C$_2$H$_5$)$_2$N | N | N | N | H | H | F | CH$_3$ | — |
| 733 | N | (C$_2$H$_5$)$_2$N | N | N | N | H | H | G | CH$_3$ | — |
| 734 | N | (C$_2$H$_5$)$_2$N | N | N | N | H | H | J | CH$_3$ | — |
| 735 | N | CH$_3$OCH$_2$CH(C$_2$H$_5$)NH | N | N | N | H | H | A | CH$_3$ | — |
| 736 | N | CH$_3$OCH$_2$CH(C$_2$H$_5$)NH | N | N | N | H | H | B | CH$_3$ | — |
| 737 | N | CH$_3$OCH$_2$CH(C$_2$H$_5$)NH | N | N | N | H | H | C | CH$_3$ | — |
| 738 | N | CH$_3$OCH$_2$CH(C$_2$H$_5$)NH | N | N | N | H | H | D | CH$_3$ | — |
| 739 | N | CH$_3$OCH$_2$CH(C$_2$H$_5$)NH | N | N | N | H | H | E | CH$_3$ | — |
| 740 | N | CH$_3$OCH$_2$CH(C$_2$H$_5$)NH | N | N | N | H | H | F | CH$_3$ | — |
| 741 | N | CH$_3$OCH$_2$CH(C$_2$H$_5$)NH | N | N | N | H | H | G | CH$_3$ | — |
| 742 | N | CH$_3$OCH$_2$CH(C$_2$H$_5$)NH | N | N | N | H | H | J | CH$_3$ | — |
| 743 | N | [CH$_3$O(CH$_2$)$_2$]$_2$N | N | N | N | H | H | A | CH$_3$ | — |
| 744 | N | [CH$_3$O(CH$_2$)$_2$]$_2$N | N | N | N | H | H | B | CH$_3$ | — |
| 745 | N | [CH$_3$O(CH$_2$)$_2$]$_2$N | N | N | N | H | H | C | CH$_3$ | — |
| 746 | N | [CH$_3$O(CH$_2$)$_2$]$_2$N | N | N | N | H | H | D | CH$_3$ | — |
| 747 | N | [CH$_3$O(CH$_2$)$_2$]$_2$N | N | N | N | H | H | E | CH$_3$ | — |
| 748 | N | [CH$_3$O(CH$_2$)$_2$]$_2$N | N | N | N | H | H | F | CH$_3$ | — |
| 749 | N | [CH$_3$O(CH$_2$)$_2$]$_2$N | N | N | N | H | H | G | CH$_3$ | — |
| 750 | N | [CH$_3$O(CH$_2$)$_2$]$_2$N | N | N | N | H | H | J | CH$_3$ | — |
| 751 | N | (C$_2$H$_5$)$_2$CHNH | N | N | N | H | H | A | CH$_3$ | — |
| 752 | N | (C$_2$H$_5$)$_2$CHNH | N | N | N | H | H | B | CH$_3$ | — |
| 753 | N | (C$_2$H$_5$)$_2$CHNH | N | N | N | H | H | C | CH$_3$ | — |
| 754 | N | (C$_2$H$_5$)$_2$CHNH | N | N | N | H | H | D | CH$_3$ | — |
| 755 | N | (C$_2$H$_5$)$_2$CHNH | N | N | N | H | H | E | CH$_3$ | — |
| 756 | N | (C$_2$H$_5$)$_2$CHNH | N | N | N | H | H | F | CH$_3$ | — |
| 757 | N | (C$_2$H$_5$)$_2$CHNH | N | N | N | H | H | G | CH$_3$ | — |
| 758 | N | (C$_2$H$_5$)$_2$CHNH | N | N | N | H | H | J | CH$_3$ | — |
| 759 | N | C$_4$H$_9$(C$_2$H$_5$)N | CH | CH | N | H | H | A | CH$_3$ | — |
| 760 | N | C$_4$H$_9$(C$_2$H$_5$)N | CH | CH | N | H | H | B | CH$_3$ | — |
| 761 | N | C$_4$H$_9$(C$_2$H$_5$)N | CH | CH | N | H | H | C | CH$_3$ | — |
| 762 | N | C$_4$H$_9$(C$_2$H$_5$)N | CH | CH | N | H | H | D | CH$_3$ | — |
| 763 | N | C$_4$H$_9$(C$_2$H$_5$)N | CH | CH | N | H | H | E | CH$_3$ | — |
| 764 | N | C$_4$H$_9$(C$_2$H$_5$)N | CH | CH | N | H | H | F | CH$_3$ | — |
| 765 | N | C$_4$H$_9$(C$_2$H$_5$)N | CH | CH | N | H | H | G | CH$_3$ | — |
| 766 | N | C$_4$H$_9$(C$_2$H$_5$)N | CH | CH | N | H | H | J | CH$_3$ | — |
| 767 | N | (C$_2$H$_5$)$_2$N | CH | CH | N | H | H | A | CH$_3$ | — |
| 768 | N | (C$_2$H$_5$)$_2$N | CH | CH | N | H | H | B | CH$_3$ | — |
| 769 | N | (C$_2$H$_5$)$_2$N | CH | CH | N | H | H | C | CH$_3$ | — |
| 770 | N | (C$_2$H$_5$)$_2$N | CH | CH | N | H | H | D | CH$_3$ | — |
| 771 | N | (C$_2$H$_5$)$_2$N | CH | CH | N | H | H | E | CH$_3$ | — |
| 772 | N | (C$_2$H$_5$)$_2$N | CH | CH | N | H | H | F | CH$_3$ | — |
| 773 | N | (C$_2$H$_5$)$_2$N | CH | CH | N | H | H | G | CH$_3$ | — |
| 774 | N | (C$_2$H$_5$)$_2$N | CH | CH | N | H | H | J | CH$_3$ | — |
| 775 | N | CH$_3$OCH$_2$CH(C$_2$H$_5$)NH | CH | CH | N | H | H | A | CH$_3$ | — |
| 776 | N | CH$_3$OCH$_2$CH(C$_2$H$_5$)NH | CH | CH | N | H | H | B | CH$_3$ | — |
| 777 | N | CH$_3$OCH$_2$CH(C$_2$H$_5$)NH | CH | CH | N | H | H | C | CH$_3$ | — |
| 778 | N | CH$_3$OCH$_2$CH(C$_2$H$_5$)NH | CH | CH | N | H | H | D | CH$_3$ | — |
| 779 | N | CH$_3$OCH$_2$CH(C$_2$H$_5$)NH | CH | CH | N | H | H | E | CH$_3$ | — |
| 780 | N | CH$_3$OCH$_2$CH(C$_2$H$_5$)NH | CH | CH | N | H | H | F | CH$_3$ | — |
| 781 | N | CH$_3$OCH$_2$CH(C$_2$H$_5$)NH | CH | CH | N | H | H | G | CH$_3$ | — |
| 782 | N | CH$_3$OCH$_2$CH(C$_2$H$_5$)NH | CH | CH | N | H | H | J | CH$_3$ | — |
| 783 | N | [CH$_3$O(CH$_2$)$_2$]$_2$N | CH | CH | N | H | H | A | CH$_3$ | — |
| 784 | N | [CH$_3$O(CH$_2$)$_2$]$_2$N | CH | CH | N | H | H | B | CH$_3$ | — |

TABLE IV-continued

| Ex. No. | A | X | M | P | Q | R⁷ | R⁸ | R⁹ᵃ | R¹⁰ | m.p. |
|---|---|---|---|---|---|---|---|---|---|---|
| 785 | N | [CH₃O(CH₂)₂]₂N | CH | CH | N | H | H | C | CH₃ | — |
| 786 | N | [CH₃O(CH₂)₂]₂N | CH | CH | N | H | H | D | CH₃ | — |
| 787 | N | [CH₃O(CH₂)₂]₂N | CH | CH | N | H | H | E | CH₃ | — |
| 788 | N | [CH₃O(CH₂)₂]₂N | CH | CH | N | H | H | F | CH₃ | — |
| 789 | N | [CH₃O(CH₂)₂]₂N | CH | CH | N | H | H | G | CH₃ | — |
| 790 | N | [CH₃O(CH₂)₂]₂N | CH | CH | N | H | H | J | CH₃ | — |
| 791 | N | (C₂H₅)₂CHNH | CH | CH | N | H | H | A | CH₃ | — |
| 792 | N | (C₂H₅)₂CHNH | CH | CH | N | H | H | B | CH₃ | — |
| 793 | N | (C₂H₅)₂CHNH | CH | CH | N | H | H | C | CH₃ | — |
| 794 | N | (C₂H₅)₂CHNH | CH | CH | N | H | H | D | CH₃ | — |
| 795 | N | (C₂H₅)₂CHNH | CH | CH | N | H | H | E | CH₃ | — |
| 796 | N | (C₂H₅)₂CHNH | CH | CH | N | H | H | F | CH₃ | — |
| 797 | N | (C₂H₅)₂CHNH | CH | CH | N | H | H | G | CH₃ | — |
| 798 | N | (C₂H₅)₂CHNH | CH | CH | N | H | H | J | CH₃ | — |
| 799 | N | C₄H₉(C₂H₅)N | CCH₃ | CCH₃ | N | H | H | A | CH₃ | — |
| 800 | N | C₄H₉(C₂H₅)N | CCH₃ | CCH₃ | N | H | H | B | CH₃ | — |
| 801 | N | C₄H₉(C₂H₅)N | CCH₃ | CCH₃ | N | H | H | C | CH₃ | — |
| 802 | N | C₄H₉(C₂H₅)N | CCH₃ | CCH₃ | N | H | H | D | CH₃ | — |
| 803 | N | C₄H₉(C₂H₅)N | CCH₃ | CCH₃ | N | H | H | E | CH₃ | — |
| 804 | N | C₄H₉(C₂H₅)N | CCH₃ | CCH₃ | N | H | H | F | CH₃ | — |
| 805 | N | C₄H₉(C₂H₅)N | CCH₃ | CCH₃ | N | H | H | G | CH₃ | — |
| 806 | N | C₄H₉(C₂H₅)N | CCH₃ | CCH₃ | N | H | H | J | CH₃ | — |
| 807 | N | (C₂H₅)₂N | CCH₃ | CCH₃ | N | H | H | A | CH₃ | — |
| 808 | N | (C₂H₅)₂N | CCH₃ | CCH₃ | N | H | H | B | CH₃ | — |
| 809 | N | (C₂H₅)₂N | CCH₃ | CCH₃ | N | H | H | C | CH₃ | — |
| 810 | N | (C₂H₅)₂N | CCH₃ | CCH₃ | N | H | H | D | CH₃ | — |
| 811 | N | (C₂H₅)₂N | CCH₃ | CCH₃ | N | H | H | E | CH₃ | — |
| 812 | N | (C₂H₅)₂N | CCH₃ | CCH₃ | N | H | H | F | CH₃ | — |
| 813 | N | (C₂H₅)₂N | CCH₃ | CCH₃ | N | H | H | G | CH₃ | — |
| 814 | N | (C₂H₅)₂N | CCH₃ | CCH₃ | N | H | H | J | CH₃ | — |
| 815 | N | CH₃OCH₂CH(C₂H₅)NH | CCH₃ | CCH₃ | N | H | H | A | CH₃ | — |
| 816 | N | CH₃OCH₂CH(C₂H₅)NH | CCH₃ | CCH₃ | N | H | H | B | CH₃ | — |
| 817 | N | CH₃OCH₂CH(C₂H₅)NH | CCH₃ | CCH₃ | N | H | H | C | CH₃ | — |
| 818 | N | CH₃OCH₂CH(C₂H₅)NH | CCH₃ | CCH₃ | N | H | H | D | CH₃ | — |
| 819 | N | CH₃OCH₂CH(C₂H₅)NH | CCH₃ | CCH₃ | N | H | H | E | CH₃ | — |
| 820 | N | CH₃OCH₂CH(C₂H₅)NH | CCH₃ | CCH₃ | N | H | H | F | CH₃ | — |
| 821 | N | CH₃OCH₂CH(C₂H₅)NH | CCH₃ | CCH₃ | N | H | H | G | CH₃ | — |
| 822 | N | CH₃OCH₂CH(C₂H₅)NH | CCH₃ | CCH₃ | N | H | H | J | CH₃ | — |
| 823 | N | [CH₃O(CH₂)₂]₂N | CCH₃ | CCH₃ | N | H | H | A | CH₃ | — |
| 824 | N | [CH₃O(CH₂)₂]₂N | CCH₃ | CCH₃ | N | H | H | B | CH₃ | — |
| 825 | N | [CH₃O(CH₂)₂]₂N | CCH₃ | CCH₃ | N | H | H | C | CH₃ | — |
| 826 | N | [CH₃O(CH₂)₂]₂N | CCH₃ | CCH₃ | N | H | H | D | CH₃ | — |
| 827 | N | [CH₃O(CH₂)₂]₂N | CCH₃ | CCH₃ | N | H | H | E | CH₃ | — |
| 828 | N | [CH₃O(CH₂)₂]₂N | CCH₃ | CCH₃ | N | H | H | F | CH₃ | — |
| 829 | N | [CH₃O(CH₂)₂]₂N | CCH₃ | CCH₃ | N | H | H | G | CH₃ | — |
| 830 | N | [CH₃O(CH₂)₂]₂N | CCH₃ | CCH₃ | N | H | H | J | CH₃ | — |
| 831 | N | (C₂H₅)₂CHNH | CCH₃ | CCH₃ | N | H | H | A | CH₃ | — |
| 832 | N | (C₂H₅)₂CHNH | CCH₃ | CCH₃ | N | H | H | B | CH₃ | — |
| 833 | N | (C₂H₅)₂CHNH | CCH₃ | CCH₃ | N | H | H | C | CH₃ | — |
| 834 | N | (C₂H₅)₂CHNH | CCH₃ | CCH₃ | N | H | H | D | CH₃ | — |
| 835 | N | (C₂H₅)₂CHNH | CCH₃ | CCH₃ | N | H | H | E | CH₃ | — |
| 836 | N | (C₂H₅)₂CHNH | CCH₃ | CCH₃ | N | H | H | F | CH₃ | — |
| 837 | N | (C₂H₅)₂CHNH | CCH₃ | CCH₃ | N | H | H | G | CH₃ | — |
| 838 | N | (C₂H₅)₂CHNH | CCH₃ | CCH₃ | N | H | H | J | CH₃ | — |
| 839 | CH | C₄H₉(C₂H₅)N | N | N | N | H | H | A | CH₃ | — |
| 840 | CH | C₄H₉(C₂H₅)N | N | N | N | H | H | B | CH₃ | — |
| 841 | CH | C₄H₉(C₂H₅)N | N | N | N | H | H | C | CH₃ | — |
| 842 | CH | C₄H₉(C₂H₅)N | N | N | N | H | H | D | CH₃ | — |
| 843 | CH | C₄H₉(C₂H₅)N | N | N | N | H | H | E | CH₃ | — |
| 844 | CH | C₄H₉(C₂H₅)N | N | N | N | H | H | F | CH₃ | — |
| 845 | CH | C₄H₉(C₂H₅)N | N | N | N | H | H | G | CH₃ | — |
| 846 | CH | C₄H₉(C₂H₅)N | N | N | N | H | H | J | CH₃ | — |
| 847 | CH | (C₂H₅)₂N | N | N | N | H | H | A | CH₃ | — |
| 848 | CH | (C₂H₅)₂N | N | N | N | H | H | B | CH₃ | — |
| 849 | CH | (C₂H₅)₂N | N | N | N | H | H | C | CH₃ | — |
| 850 | CH | (C₂H₅)₂N | N | N | N | H | H | D | CH₃ | — |

TABLE IV-continued

| Ex. No. | A | X | M | P | Q | R$^7$ | R$^8$ | R$^{9a}$ | R$^{10}$ | m.p. |
|---|---|---|---|---|---|---|---|---|---|---|
| 851 | CH | (C$_2$H$_5$)$_2$N | N | N | N | H | H | E | CH$_3$ | — |
| 852 | CH | (C$_2$H$_5$)$_2$N | N | N | N | H | H | F | CH$_3$ | — |
| 853 | CH | (C$_2$H$_5$)$_2$N | N | N | N | H | H | G | CH$_3$ | — |
| 854 | CH | (C$_2$H$_5$)$_2$N | N | N | N | H | H | J | CH$_3$ | — |
| 855 | CH | CH$_3$OCH$_2$CH(C$_2$H$_5$)NH | N | N | N | H | H | A | CH$_3$ | — |
| 856 | CH | CH$_3$OCH$_2$CH(C$_2$H$_5$)NH | N | N | N | H | H | B | CH$_3$ | — |
| 857 | CH | CH$_3$OCH$_2$CH(C$_2$H$_5$)NH | N | N | N | H | H | C | CH$_3$ | — |
| 858 | CH | CH$_3$OCH$_2$CH(C$_2$H$_5$)NH | N | N | N | H | H | D | CH$_3$ | — |
| 859 | CH | CH$_3$OCH$_2$CH(C$_2$H$_5$)NH | N | N | N | H | H | E | CH$_3$ | — |
| 860 | CH | CH$_3$OCH$_2$CH(C$_2$H$_5$)NH | N | N | N | H | H | F | CH$_3$ | — |
| 861 | CH | CH$_3$OCH$_2$CH(C$_2$H$_5$)NH | N | N | N | H | H | G | CH$_3$ | — |
| 862 | CH | CH$_3$OCH$_2$CH(C$_2$H$_5$)NH | N | N | N | H | H | J | CH$_3$ | — |
| 863 | CH | [CH$_3$O(CH$_2$)$_2$]$_2$N | N | N | N | H | H | A | CH$_3$ | — |
| 864 | CH | [CH$_3$O(CH$_2$)$_2$]$_2$N | N | N | N | H | H | B | CH$_3$ | — |
| 865 | CH | [CH$_3$O(CH$_2$)$_2$]$_2$N | N | N | N | H | H | C | CH$_3$ | — |
| 866 | CH | [CH$_3$O(CH$_2$)$_2$]$_2$N | N | N | N | H | H | D | CH$_3$ | — |
| 867 | CH | [CH$_3$O(CH$_2$)$_2$]$_2$N | N | N | N | H | H | E | CH$_3$ | — |
| 868 | CH | [CH$_3$O(CH$_2$)$_2$]$_2$N | N | N | N | H | H | F | CH$_3$ | — |
| 869 | CH | [CH$_3$O(CH$_2$)$_2$]$_2$N | N | N | N | H | H | G | CH$_3$ | — |
| 870 | CH | [CH$_3$O(CH$_2$)$_2$]$_2$N | N | N | N | H | H | J | CH$_3$ | — |
| 871 | CH | (C$_2$H$_5$)$_2$CHNH | N | N | N | H | H | A | CH$_3$ | — |
| 872 | CH | (C$_2$H$_5$)$_2$CHNH | N | N | N | H | H | B | CH$_3$ | — |
| 873 | CH | (C$_2$H$_5$)$_2$CHNH | N | N | N | H | H | C | CH$_3$ | — |
| 874 | CH | (C$_2$H$_5$)$_2$CHNH | N | N | N | H | H | D | CH$_3$ | — |
| 875 | CH | (C$_2$H$_5$)$_2$CHNH | N | N | N | H | H | E | CH$_3$ | — |
| 876 | CH | (C$_2$H$_5$)$_2$CHNH | N | N | N | H | H | F | CH$_3$ | — |
| 877 | CH | (C$_2$H$_5$)$_2$CHNH | N | N | N | H | H | G | CH$_3$ | — |
| 878 | CH | (C$_2$H$_5$)$_2$CHNH | N | N | N | H | H | J | CH$_3$ | — |
| 879 | CH | C$_4$H$_9$(C$_2$H$_5$)N | CH | CH | N | H | H | A | CH$_3$ | — |
| 880 | CH | C$_4$H$_9$(C$_2$H$_5$)N | CH | CH | N | H | H | B | CH$_3$ | — |
| 881 | CH | C$_4$H$_9$(C$_2$H$_5$)N | CH | CH | N | H | H | C | CH$_3$ | — |
| 882 | CH | C$_4$H$_9$(C$_2$H$_5$)N | CH | CH | N | H | H | D | CH$_3$ | — |
| 883 | CH | C$_4$H$_9$(C$_2$H$_5$)N | CH | CH | N | H | H | E | CH$_3$ | — |
| 884 | CH | C$_4$H$_9$(C$_2$H$_5$)N | CH | CH | N | H | H | F | CH$_3$ | — |
| 885 | CH | C$_4$H$_9$(C$_2$H$_5$)N | CH | CH | N | H | H | G | CH$_3$ | — |
| 886 | CH | C$_4$H$_9$(C$_2$H$_5$)N | CH | CH | N | H | H | J | CH$_3$ | — |
| 887 | CH | (C$_2$H$_5$)$_2$N | CH | CH | N | H | H | A | CH$_3$ | — |
| 888 | CH | (C$_2$H$_5$)$_2$N | CH | CH | N | H | H | B | CH$_3$ | — |
| 889 | CH | (C$_2$H$_5$)$_2$N | CH | CH | N | H | H | C | CH$_3$ | — |
| 890 | CH | (C$_2$H$_5$)$_2$N | CH | CH | N | H | H | D | CH$_3$ | — |
| 891 | CH | (C$_2$H$_5$)$_2$N | CH | CH | N | H | H | E | CH$_3$ | — |
| 892 | CH | (C$_2$H$_5$)$_2$N | CH | CH | N | H | H | F | CH$_3$ | — |
| 893 | CH | (C$_2$H$_5$)$_2$N | CH | CH | N | H | H | G | CH$_3$ | — |
| 894 | CH | (C$_2$H$_5$)$_2$N | CH | CH | N | H | H | J | CH$_3$ | — |
| 895 | CH | CH$_3$OCH$_2$CH(C$_2$H$_5$)NH | CH | CH | N | H | H | A | CH$_3$ | — |
| 896 | CH | CH$_3$OCH$_2$CH(C$_2$H$_5$)NH | CH | CH | N | H | H | B | CH$_3$ | — |
| 897 | CH | CH$_3$OCH$_2$CH(C$_2$H$_5$)NH | CH | CH | N | H | H | C | CH$_3$ | — |
| 898 | CH | CH$_3$OCH$_2$CH(C$_2$H$_5$)NH | CH | CH | N | H | H | D | CH$_3$ | — |
| 899 | CH | CH$_3$OCH$_2$CH(C$_2$H$_5$)NH | CH | CH | N | H | H | E | CH$_3$ | — |
| 900 | CH | CH$_3$OCH$_2$CH(C$_2$H$_5$)NH | CH | CH | N | H | H | F | CH$_3$ | — |
| 901 | CH | CH$_3$OCH$_2$CH(C$_2$H$_5$)NH | CH | CH | N | H | H | G | CH$_3$ | — |
| 902 | CH | CH$_3$OCH$_2$CH(C$_2$H$_5$)NH | CH | CH | N | H | H | J | CH$_3$ | — |
| 903 | CH | [CH$_3$O(CH$_2$)$_2$]$_2$N | CH | CH | N | H | H | A | CH$_3$ | — |
| 904 | CH | [CH$_3$O(CH$_2$)$_2$]$_2$N | CH | CH | N | H | H | B | CH$_3$ | — |
| 905 | CH | [CH$_3$O(CH$_2$)$_2$]$_2$N | CH | CH | N | H | H | C | CH$_3$ | — |
| 906 | CH | [CH$_3$O(CH$_2$)$_2$]$_2$N | CH | CH | N | H | H | D | CH$_3$ | — |
| 907 | CH | [CH$_3$O(CH$_2$)$_2$]$_2$N | CH | CH | N | H | H | E | CH$_3$ | — |
| 908 | CH | [CH$_3$O(CH$_2$)$_2$]$_2$N | CH | CH | N | H | H | F | CH$_3$ | — |
| 909 | CH | [CH$_3$O(CH$_2$)$_2$]$_2$N | CH | CH | N | H | H | G | CH$_3$ | — |
| 910 | CH | [CH$_3$O(CH$_2$)$_2$]$_2$N | CH | CH | N | H | H | J | CH$_3$ | — |
| 911 | CH | (C$_2$H$_5$)$_2$CHNH | CH | CH | N | H | H | A | CH$_3$ | — |
| 912 | CH | (C$_2$H$_5$)$_2$CHNH | CH | CH | N | H | H | B | CH$_3$ | — |
| 913 | CH | (C$_2$H$_5$)$_2$CHNH | CH | CH | N | H | H | C | CH$_3$ | — |
| 914 | CH | (C$_2$H$_5$)$_2$CHNH | CH | CH | N | H | H | D | CH$_3$ | — |
| 915 | CH | (C$_2$H$_5$)$_2$CHNH | CH | CH | N | H | H | E | CH$_3$ | — |
| 916 | CH | (C$_2$H$_5$)$_2$CHNH | CH | CH | N | H | H | F | CH$_3$ | — |

TABLE IV-continued

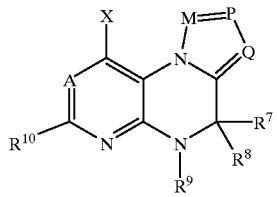

| Ex. No. | A | X | M | P | Q | R⁷ | R⁸ | R⁹ᵃ | R¹⁰ | m.p. |
|---|---|---|---|---|---|---|---|---|---|---|
| 917 | CH | $(C_2H_5)_2$CHNH | CH | CH | N | H | H | G | $CH_3$ | — |
| 918 | CH | $(C_2H_5)_2$CHNH | CH | CH | N | H | H | J | $CH_3$ | — |
| 919 | CH | $C_4H_9(C_2H_5)N$ | $CCH_3$ | $CCH_3$ | N | H | H | A | $CH_3$ | — |
| 920 | CH | $C_4H_9(C_2H_5)N$ | $CCH_3$ | $CCH_3$ | N | H | H | B | $CH_3$ | — |
| 921 | CH | $C_4H_9(C_2H_5)N$ | $CCH_3$ | $CCH_3$ | N | H | H | C | $CH_3$ | — |
| 922 | CH | $C_4H_9(C_2H_5)N$ | $CCH_3$ | $CCH_3$ | N | H | H | D | $CH_3$ | — |
| 923 | CH | $C_4H_9(C_2H_5)N$ | $CCH_3$ | $CCH_3$ | N | H | H | E | $CH_3$ | — |
| 924 | CH | $C_4H_9(C_2H_5)N$ | $CCH_3$ | $CCH_3$ | N | H | H | F | $CH_3$ | — |
| 925 | CH | $C_4H_9(C_2H_5)N$ | $CCH_3$ | $CCH_3$ | N | H | H | G | $CH_3$ | — |
| 926 | CH | $C_4H_9(C_2H_5)N$ | $CCH_3$ | $CCH_3$ | N | H | H | J | $CH_3$ | — |
| 927 | CH | $(C_2H_5)_2N$ | $CCH_3$ | $CCH_3$ | N | H | H | A | $CH_3$ | — |
| 928 | CH | $(C_2H_5)_2N$ | $CCH_3$ | $CCH_3$ | N | H | H | B | $CH_3$ | — |
| 929 | CH | $(C_2H_5)_2N$ | $CCH_3$ | $CCH_3$ | N | H | H | C | $CH_3$ | — |
| 930 | CH | $(C_2H_5)_2N$ | $CCH_3$ | $CCH_3$ | N | H | H | D | $CH_3$ | — |
| 931 | CH | $(C_2H_5)_2N$ | $CCH_3$ | $CCH_3$ | N | H | H | E | $CH_3$ | — |
| 932 | CH | $(C_2H_5)_2N$ | $CCH_3$ | $CCH_3$ | N | H | H | F | $CH_3$ | — |
| 933 | CH | $(C_2H_5)_2N$ | $CCH_3$ | $CCH_3$ | N | H | H | G | $CH_3$ | — |
| 934 | CH | $(C_2H_5)_2N$ | $CCH_3$ | $CCH_3$ | N | H | H | J | $CH_3$ | — |
| 935 | CH | $CH_3OCH_2CH(C_2H_5)NH$ | $CCH_3$ | $CCH_3$ | N | H | H | A | $CH_3$ | — |
| 936 | CH | $CH_3OCH_2CH(C_2H_5)NH$ | $CCH_3$ | $CCH_3$ | N | H | H | B | $CH_3$ | — |
| 937 | CH | $CH_3OCH_2CH(C_2H_5)NH$ | $CCH_3$ | $CCH_3$ | N | H | H | C | $CH_3$ | — |
| 938 | CH | $CH_3OCH_2CH(C_2H_5)NH$ | $CCH_3$ | $CCH_3$ | N | H | H | D | $CH_3$ | — |
| 939 | CH | $CH_3OCH_2CH(C_2H_5)NH$ | $CCH_3$ | $CCH_3$ | N | H | H | E | $CH_3$ | — |
| 940 | CH | $CH_3OCH_2CH(C_2H_5)NH$ | $CCH_3$ | $CCH_3$ | N | H | H | F | $CH_3$ | — |
| 941 | CH | $CH_3OCH_2CH(C_2H_5)NH$ | $CCH_3$ | $CCH_3$ | N | H | H | G | $CH_3$ | — |
| 942 | CH | $CH_3OCH_2CH(C_2H_5)NH$ | $CCH_3$ | $CCH_3$ | N | H | H | J | $CH_3$ | — |
| 943 | CH | $[CH_3O(CH_2)_2]_2N$ | $CCH_3$ | $CCH_3$ | N | H | H | A | $CH_3$ | — |
| 944 | CH | $[CH_3O(CH_2)_2]_2N$ | $CCH_3$ | $CCH_3$ | N | H | H | B | $CH_3$ | — |
| 945 | CH | $[CH_3O(CH_2)_2]_2N$ | $CCH_3$ | $CCH_3$ | N | H | H | C | $CH_3$ | — |
| 946 | CH | $[CH_3O(CH_2)_2]_2N$ | $CCH_3$ | $CCH_3$ | N | H | H | D | $CH_3$ | — |
| 947 | CH | $[CH_3O(CH_2)_2]_2N$ | $CCH_3$ | $CCH_3$ | N | H | H | E | $CH_3$ | — |
| 948 | CH | $[CH_3O(CH_2)_2]_2N$ | $CCH_3$ | $CCH_3$ | N | H | H | F | $CH_3$ | — |
| 949 | CH | $[CH_3O(CH_2)_2]_2N$ | $CCH_3$ | $CCH_3$ | N | H | H | G | $CH_3$ | — |
| 950 | CH | $[CH_3O(CH_2)_2]_2N$ | $CCH_3$ | $CCH_3$ | N | H | H | J | $CH_3$ | — |
| 951 | CH | $(C_2H_5)_2$CHNH | $CCH_3$ | $CCH_3$ | N | H | H | A | $CH_3$ | — |
| 952 | CH | $(C_2H_5)_2$CHNH | $CCH_3$ | $CCH_3$ | N | H | H | B | $CH_3$ | — |
| 953 | CH | $(C_2H_5)_2$CHNH | $CCH_3$ | $CCH_3$ | N | H | H | C | $CH_3$ | — |
| 954 | CH | $(C_2H_5)_2$CHNH | $CCH_3$ | $CCH_3$ | N | H | H | D | $CH_3$ | — |
| 955 | CH | $(C_2H_5)_2$CHNH | $CCH_3$ | $CCH_3$ | N | H | H | E | $CH_3$ | — |
| 956 | CH | $(C_2H_5)_2$CHNH | $CCH_3$ | $CCH_3$ | N | H | H | F | $CH_3$ | — |
| 957 | CH | $(C_2H_5)_2$CHNH | $CCH_3$ | $CCH_3$ | N | H | H | G | $CH_3$ | — |
| 958 | CH | $(C_2H_5)_2$CHNH | $CCH_3$ | $CCH_3$ | N | H | H | J | $CH_3$ | — |
| 959 | N | $C_4H_9(C_2H_5)N$ | N | N | N | $CH_3$ | $CH_3$ | A | $CH_3$ | — |
| 960 | N | $C_4H_9(C_2H_5)N$ | N | N | N | H | H | A | H | — |
| 961 | N | $C_4H_9(C_2H_5)N$ | N | N | N | H | H | A | CN | — |
| 962 | N | $C_4H_9(C_2H_5)N$ | CH | CH | N | $CH_3$ | $CH_3$ | A | $CH_3$ | — |
| 963 | N | $C_4H_9(C_2H_5)N$ | CH | CH | N | H | H | A | H | — |
| 964 | N | $C_4H_9(C_2H_5)N$ | CH | CH | N | H | H | A | CN | — |
| 965 | N | $C_4H_9(C_2H_5)N$ | $CCH_3$ | $CCH_3$ | N | $CH_3$ | $CH_3$ | A | $CH_3$ | — |
| 966 | N | $C_4H_9(C_2H_5)N$ | $CCH_3$ | $CCH_3$ | N | H | H | A | H | — |
| 967 | N | $C_4H_9(C_2H_5)N$ | $CCH_3$ | $CCH_3$ | N | H | H | A | CN | — |

Utility

CRF-R1 Receptor Binding Assay for the Evaluation of Biological Activity

The following is a description of the isolation of cell membranes containing cloned human CRF-R1 receptors for use in the standard binding assay as well as a description of the assay itself.

Messenger RNA was isolated from human hippocampus. The mRNA was reverse transcribed using oligo (dt) 12–18 and the coding region was amplified by PCR from start to stop codons The resulting PCR fragment was cloned into the EcoRV site of pGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were 'selected in the presence of 400 μM hygromycin. Cells surviving 4 weeks of selection in hygromycin were pooled, adapted to growth in suspension and used to generate membranes for the binding assay described below.

Individual aliquots containing approximately 1×108 of the suspended cells were then centrifuged to form a pellet and frozen.

For the binding assay a frozen pellet described above containing 293EBNA cells transfected with hCRFR1 receptors is homogenized in 10 ml of ice cold tissue buffer (50 mM HEPES buffer pH 7.0, containing 10 mM $MgCl_2$, 2 mM EGTA, 1 µg/l aprotinin, 1 µg/ml leupeptin and 1 µg/ml pepstatin). The homogenate is centrifuged at 40,000×g for 12 min and the resulting pellet rehomogenized in 10 ml of tissue buffer. After another centrifugation at 40,000×g for 12 min, the pellet is resuspended to a protein concentration of 360 µg/ml to be used in the assay.

Binding assays are performed in 96 well plates; each well having a 300 µl capacity. To each well is added 50 µl of test drug dilutions (final concentration of drugs range from $10^{-10}$–$10^{-5}$ M), 100 µl of $^{125}$I-ovine-CRF ($^{125}$I-o-CRF) (final concentration 150 pM) and 150 µl of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, *Anal. Biochem.* 107:220 (1980), which provides Ki values for inhibition which are then used to assess biological activity.

A compound is considered to be active if it has a $K_i$ value of less than about 10000 nM for the inhibition of CRF.

Inhibition of CRF-Stimulated Adenylate Cyclase Activity

Inhibition of CRF-stimulated adenylate cyclase activity was performed as described by G. Battaglia et al. *Synapse* 1:572 (1987). Briefly, assays were carried out at 37° C. for 10 min in 200 ml of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM oCRF, antagonist peptides (concentration range $10^{-9}$ to $10^{-6m}$) and 0.8 mg original wet weight tissue (approximately 40–60 mg protein). Reactions were initiated by the addition of 1 mM ATP/$^{32}$P] ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 µl of [$^3$H]cAMP (approximately 40,000 dpm) was added to each tube prior to separation. The separation of [$^{32}$P]cAMP from [$^{32}$P]ATP was performed by sequential elution over Dowex and alumina columns. Recovery was consistently greater than 80%.

Some compounds of this invention were tested in this assay and found to be active.

In vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn Brain *Research Reviews* 15:71 (1990) Compounds may be tested in any species of rodent or small mammal. Disclosure of the assays herein is not intended to limit the enablement of the invention.

Compounds of this invention have utility in the treatment of inbalances associated with abnormal levels of corticotropin releasing factor in patients suffering from depression, affective disorders, and/or anxiety.

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

What is claimed is:

1. A method of treating an affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, or inflammatory disorder in a mammal comprising administering to the mammal a therapeutically effective amount of a CRF antagonist compound of formula I:

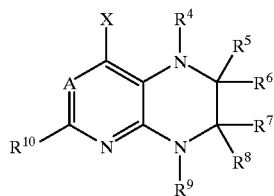

(I)

or a pharmaceutically accetable salt or prodrug thereof, wherein:

A is N or C—$R^{11}$;

X is H, $OR^1$, $S(O)_nR^1$, $NR^1R^2$, $CR^1R^2R^3$, phenyl (optionally substituted with 1–4 groups independently chosen from halogen, $C_1$–$C_4$ haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl) or heteroaryl (optionally substituted at one to all valence-allowed positions with groups independently chosen from halogen, $C_1$–$C_4$ haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl);

n is 0, 1 or 2;

$R^1$ is $C_1$–$C_{12}$ alkyl, $C_2$–$C_{12}$ alkoxyalkyl, $C_3$–$C_{12}$ cycloalkyl, $C_4$–$C_{12}$ cycloalkylalkyl, $C_2$–$C_{12}$ alkenyl, $C_2$–$C_{12}$ alkynyl, aryl-($C_1$–$C_{12}$ alkyl), $C_3$–$C_{12}$ dialkylaminoalkyl, $C_2$–$C_{13}$ cyanoalkyl, $C_2$–$C_5$ carboalkoxy-($C_1$–$C_{12}$ alkyl), phenyl (optionally substituted with 1–4 groups independently chosen from halogen, $C_1$–$C_4$ haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl), or heteroaryl (optionally substituted at one to all valence-allowed positions with groups independently chosen from halogen, $C_1$–$C_4$ haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl);

$R^2$ and $R^3$ are independently chosen from H, $C_1$–$C_{12}$ alkyl, $C_2$–$C_{12}$ alkoxyalkyl, $C_3$–$C_{12}$ cycloalkyl, $C_4$–$C_{12}$ cycloalkylalkyl, $C_2$–$C_{12}$ alkenyl, $C_2$–$C_{12}$ alkynyl, aryl-($C_1$–$C_{12}$ alkyl), $C_3$–$C_{12}$ dialkylaminoalkyl, $C_2$–$C_{13}$ cyanoalkyl, $C_1$–$C_4$ carboalkoxy, $C_2$–$C_{12}$ carboalkoxyalkyl, C(=O) $CH_3$, phenyl (optionally substituted with 1–4 groups independently chosen from halogen, $C_1$–$C_4$ haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl), or heteroaryl (optionally substituted at one to all valence-allowed positions with groups independently chosen from halogen, $C_1$–$C_4$ haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl);

$R^4$ is H, $C_1$–$C_{12}$ alkyl, allyl, propargyl or benzyl (optionally substituted with 1–4 groups independently chosen from halogen, $C_1$–$C_4$ haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl);

$R^1$ and $R^4$ may also optionally be taken together, along with the other four interconnected atoms, to form a ring of 5–9 total atoms, the structural sequence between the X group and the ring nitrogen atom consisting of the group $(CH_2)_pW(CH_2)_q$;

p and q are independently 0, 1 or 2;

W is $CH_2$, $C(CH_3)_2$, C(=O), O, S or $NCH_3$;

$R^5$, $R^6$, $R^7$ and $R^8$ are independently chosen from H, $C_1$–$C_4$ alkyl, allyl, propargyl, phenyl (optionally substituted with 1–4 groups independently chosen from halogen, $C_1$–$C_4$ haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl) or benzyl (optionally substituted with 1–4 groups independently chosen from halogen, $C_1$–$C_4$ haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl);

$R^4$, $R^5$ and $R^6$ may also be taken together, along with the two interconnecting atoms, to constitute either an imidazole or tetrazole ring, the imidazole ring being optionally substituted with 1–2 groups chosen independently from $C_1$–$C_4$ alkyl or phenyl;

$R^5$ and $R^6$ may also be taken together to be O, S or $NR^{12}$;

$R^9$ is phenyl (optionally substituted with 1–4 groups chosen from halogen, $C_1$–$C_4$ haloalkyl, $C_1$–$C_4$ alkyl, $C_2$–$C_6$ alkenyl, $C_1$–$C_4$ alkoxy, $C_1$–$C_4$ alkylthio, $C_1$–$C_4$ alkylsulfonyl, $C_2$–$C_6$ dialkylamino, nitro, $C_2$–$C_5$ carboalkoxy or cyano), pyridyl (optionally substituted with 1–4 groups chosen from halogen, $C_1$–$C_4$ haloalkyl, $C_1$–$C_4$ alkyl, $C_2$–$C_6$ alkenyl, $C_1$–$C_4$ alkoxy, $C_1$–$C_4$ alkylthio, $C_1$–$C_4$ alkylsulfonyl, $C_2$–$C_6$ dialkylamino, nitro, $C_2$–$C_5$ carboalkoxy or cyano), or pyrimidyl (optionally substituted with 1–4 groups chosen from halogen, $C_1$–$C_4$ haloalkyl, $C_1$–$C_4$ alkyl, $C_2$–$C_6$ alkenyl, $C_1$–$C_4$ alkoxy, $C_1$–$C_4$ alkylthio, $C_1$–$C_4$ alkylsulfonyl, $C_2$–$C_6$ dialkylamino, nitro, $C_2$–$C_5$ carboalkoxy or cyano);

$R^{10}$ is H, $C_1$–$C_4$ alkyl or cyano;

$R^{11}$ is H, $C_1$–$C_4$ alkyl or halogen;

$R^{12}$ is H, $C_1$–$C_4$ alkyl or phenyl;

aryl is phenyl, biphenyl or naphthyl; and heteroaryl is pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl or pyrazolyl.

2. Method of claim 1 wherein, in the compound of formula I,

X is $OR^1$, $NR^1R^2$, $CR^1R^2R^3$, or phenyl (optionally substituted at the 2-position with $CF_3$, nitro, halogen or cyano);

$R^1$ is $C_1$–$C_{12}$ alkyl, $C_2$–$C_{12}$ alkoxyalkyl, $C_3$–$C_{12}$ cycloalkyl, $C_4$–$C_{12}$ cycloalkylalkyl, aryl-($C_1$–$C_{12}$ alkyl), $C_3$–$C_{12}$ dialkylaminoalkyl, or phenyl (optionally substituted with 1–4 groups independently chosen from halogen, haloalkyl, nitro, $C_1$–$C_4$ alkyl, $C_2$–$C_5$ carboalkoxy, cyano, OH, $C_1$–$C_4$ alkoxy, SH, $C_1$–$C_4$ alkylthio, $NH_2$, $C_1$–$C_4$ alkylamino, $C_2$–$C_8$ dialkylamino, or phenyl);

$R^4$ is H or $C_1$–$C_4$ alkyl;

$R^5$ and $R^6$ are either H or $C_1$–$C_4$ alkyl;

$R^4$, $R^5$ and $R^6$ may also be taken together, along with the two interconnecting atoms, to constitute a tetrazole ring;

$R^9$ is phenyl (optionally substituted with 1–4 groups chosen from halogen, $C_1$–$C_4$ haloalkyl, $C_1$–$C_4$ alkyl, $C_2$–$C_6$ alkenyl, $C_1$–$C_4$ alkoxy, $C_1$–$C_4$ alkylthio, $C_1$–$C_4$ alkylsulfonyl, $C_2$–$C_6$ dialkylamino, nitro, $C_2$–$C_5$ carboalkoxy or cyano), 3-pyridyl (optionally substituted with 1–4 groups chosen from halogen, $C_1$–$C_4$ haloalkyl, $C_1$–$C_4$ alkyl, $C_2$–$C_6$ alkenyl, $C_1$–$C_4$ alkoxy, $C_1$–$C_4$ alkylthio, $C_1$–$C_4$ alkylsulfonyl, $C_2$–$C_6$ dialkylamino, nitro, $C_2$–$C_5$ carboalkoxy or cyano), or 5-pyrimidyl (optionally substituted with 1–4 groups chosen from halogen, $C_1$–$C_4$ haloalkyl, $C_1$–$C_4$ alkyl, $C_2$–$C_6$ alkenyl, $C_1$–$C_4$ alkoxy, $C_1$–$C_4$ alkylthio, $C_1$–$C_4$ alkylsulfonyl, $C_2$–$C_6$ dialkylamino, nitro, $C_2$–$C_5$ carboalkoxy or cyano);

$R^{10}$ is $CH_3$;

and $R^{11}$ is H.

3. Method of claim 2 wherein, in the compound of formula (I):

A is N;

X is $NR^1R^2$ or $CR^1R^2R^3$;

$R^1$ is $C_1$–$C_6$ alkyl or $C_2$–$C_8$ alkoxyalkyl;

$R^2$ and $R^3$ are independently H, $C_1$–$C_6$ alkyl or $C_2$–$C_8$ alkoxyalkyl;

$R^4$ is H;

$R^5$ and $R^6$ are H;

$R^7$ and $R^8$ are independently H or $CH_3$; and $R^9$ is phenyl (optionally substituted with 1–4 groups chosen from halogen, $C_1$–$C_4$ haloalkyl, $C_1$–$C_4$ alkyl, $C_2$–$C_6$ alkenyl, $C_1$–$C_4$ alkoxy, $C_1$–$C_4$ alkylthio, $C_1$–$C_4$ alkylsulfonyl, $C_2$–$C_6$ dialkylamino, nitro, $C_2$–$C_5$ carboalkoxy or cyano).

4. Method of claim 1 wherein the compound of formula I is selected from:

8-(2-bromo-4-isopropylphenyl)-4-(ethylbutylamino)-2-methyl-5,6,7,8-tetrahydropteridine;

8-(2-chloro-4,6-dimethoxyphenyl)-4-(ethylbutylamino)-2-methyl-5,6,7,8-tetrahydropteridine;

4-(ethylbutylamino)-2-methyl-8-(2,4,6-trimethylphenyl)-5,6,7,8-tetrahydropteridine; and 4-(1-methoxy-2-butyl)amino-2-methyl-8-(2,4,6-trimethylphenyl)-5,6,7,8-tetrahydropteridine.

* * * * *